US009150834B2

(12) United States Patent
Brennan et al.

(10) Patent No.: US 9,150,834 B2
(45) Date of Patent: Oct. 6, 2015

(54) HUMAN IMMUNODEFICIENCY VIRUS AND USES THEREOF

(75) Inventors: Catherine A. Brennan, Libertyville, IL (US); Vera Holzmayer, Green Oaks, IL (US); Anadruzela S. Vallari, Libertyville, IL (US); Julie Yamaguchi, Chicago, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 614 days.

(21) Appl. No.: 13/028,816

(22) Filed: Feb. 16, 2011

(65) Prior Publication Data

US 2011/0281258 A1    Nov. 17, 2011

Related U.S. Application Data

(60) Provisional application No. 61/304,918, filed on Feb. 16, 2010, provisional application No. 61/376,151, filed on Aug. 23, 2010.

(51) Int. Cl.
| | |
|---|---|
| *C12N 15/49* | (2006.01) |
| *C12N 7/00* | (2006.01) |
| *C07K 14/16* | (2006.01) |
| *C07K 14/005* | (2006.01) |
| *C12Q 1/70* | (2006.01) |

(52) U.S. Cl.
CPC ............... *C12N 7/00* (2013.01); *C07K 14/005* (2013.01); *C07K 14/16* (2013.01); *C12N 2740/15022* (2013.01); *C12N 2740/16021* (2013.01); *C12N 2740/16122* (2013.01); *C12N 2740/16222* (2013.01); *C12N 2740/16322* (2013.01); *C12Q 1/703* (2013.01)

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 4,510,245 | A | 4/1985 | Cousens et al. |
| 4,634,665 | A | 1/1987 | Axel et al. |
| 4,968,615 | A | 11/1990 | Koszinowski et al. |
| 5,168,062 | A | 12/1992 | Stinski |
| 5,179,017 | A | 1/1993 | Axel et al. |
| 7,615,614 | B2 | 11/2009 | Hackett, Jr. et al. |

OTHER PUBLICATIONS

Ausubel F.M., et al. "A Compendium of Methods from Current Protocols in Molecular Biology" in: Short Protocols in Molecular Biology, Ausubel F.M., et al., John Wiely & Sons, 1989, Table of Contents.
Goeddel D.V., "Systems for Heterologous Gene Expression," Methods in Enzymology, 1990, vol. 185, Table of Contents.
Gouy M., et al., "Codon Usage in Bacteria: Correlation with Gene Expressivity," Nucleic acids Research, 1982, vol. 10 (22), pp. 7055-7074.
Haugland., et al., "Handbook of Fluorescent Probes and Research Chemicals," Molecular Probes, 1996, Table of Contents.
Hickman R., et al., "Detection and differentiation of HIV-1 group 0 sera from HIV-1 group M and HIV-2 using recombinant antigens and peptides.," Journal of Virological Methods, 1988, 72, 1, 43-49.
International Search Report for Application No. PCT/US2011/025077, mailed on Jun. 10, 2011, 4 pages.
Paul W.E., Ed., Fundamental Immunology, Chapter 12, Raven Press, New York, 1989, pp. 332-336.
Plantier J.C., et al., "A New Human Immunodeficiency Virus Derived From Gorillas," Nature Medicine, 2009, vol. 15 (8), pp. 871-872.
Polak J.M., et al., Introduction to Immunocytochemistry, 2nd Edition, Springer-Verlag, 1997, Table of Contents.
Robinson J.R., Sustained and Controlled Release Drug Delivery Systems, Marcel Dekker, Inc., 1978, Table of Contents.
Sambrook J., et al., eds., Molecular Cloning: A Laboratory Manual, 3rd Edition, Cold Spring Harbor Laboratory, 2001, Table of Contents.
Sambrook J., et al., "Molecular Cloning: A Laboratory Manual," 1989, 2nd Ed., Cold Spring Harbor Laboratory Press, Table of Contents.
Takehisa J., et al., "Origin and Biology of Simian Immunodeficiency Virus in Wild-living Western Gorillas," Journal of Virology, 2009, vol. 83 (4), pp. 1635-1648.
Yamaguchi J., et al., "HIV Infections in Northwestern Cameroon: Identification of HIV Type 1 group O and Dual HIV Type 1 Group M and Group O Infections," AIDS Research and Human Retroviruses, 2004, vol. 20 (9), pp. 944-957.
International Preliminary Report on Patentability and Written Opinion for Application No. PCT/US2011/025077, mailed on Aug. 21, 2012, 9 pages.
European Patent Office Action for Application No. 11706105.1 dated Feb. 5, 2015 (8 pages).

*Primary Examiner* — Mary E Mosher
*Assistant Examiner* — Myron Hill
(74) *Attorney, Agent, or Firm* — Irene M. Reininger

(57) ABSTRACT

The present invention relates to Human Immunodeficiency Virus-1 (HIV-1) Group P of the strain designated 06CMU14788 and fragments thereof, primers which are derived from HIV-1 Group P, immunogenic regions thereof, immunoassays and nucleic acid based assays for the detection of Human Immunodeficiency Virus (HIV) that employ said HIV-1 Group P or fragments thereof and therapeutic compositions containing said HIV-1 Group P or fragments thereof.

2 Claims, 46 Drawing Sheets

FIGURE 4

```
         tip
                          10        20        30
                    ---------+---------+---------+----
U14788 cg           CIRPGNNTRGQVQLGVMTWYNMKHYVGDIRAAHC
env_clone1          ..............AS.................
env_clone2          ...............I........I........
env_clone3          ...............I........I........
```

. indicates identity to U14788 genome sequence

FIGURE 5 A

```
5'  TAAAGCTTGC CTTGAGTGAG TAAAGCAGTG TGTGCTCATC TGTTCAGACT
                                                              50

5'  CTGGTATCTA GAGATCCCTC AGAGCACTTT TAGCCGAGTG AAAAATCTCT
                                                              100

5'  AGCAGTGGCG CCCGAACAGG GACCTGAAAG TGAAACCAGT TTCTGAAACC
                                                              150

5'  TCCGACGCAC GGGCTCGGCT CAGCGGAGTG CACCTGCTGA GAGGCGAGAG
                                                              200

5'  GAACTCACGG CGGTGAGTAC ATTTTGTCAG TGGTGACTGA CCCTAGGGGA
                                                              250

5'  AGAGGCGAAG TCTCTAGGGG AGGAGATGGG TGCGAGAGCG TCAGTGTTGA
                                                              300
                                        gag
                                Met Gly Ala Arg Ala Ser Val Leu
                                 1   2   3   4   5   6   7   8

5'  CAGGGGGCCG ATTGGATGCA TGGGAAAGAA TTAGGCTTAG ACCAGGAGGT
                                                              350
                              gag
    Thr Gly Gly Arg Leu Asp Ala Trp Glu Arg  Ie Arg Leu Arg Pro Gly Gly
     9  10  11  12  13  14  15  16  17  18  19  20  21  22  23  24  25

5'  AAGAAAAAAT ATAAGCTAAA ACATGTAGTA TGGGCAAGCA GAGAGCTGGA
                                                              400
                              gag
    Lys Lys Lys Tyr Lys Leu Lys His Val Val Trp Ala Ser Arg Glu Leu Glu
     26  27  28  29  30  31  32  33  34  35  36  37  38  39  40  41  42

5'  AAGATTTGCA TGTAATCCTG GGCTTATGGA AACAGCGGAA GGCTGCGAAA
                                                              450
                              gag
    Arg Phe Ala Cys Asn Pro Gly Leu Met Glu Thr Ala Glu Gly Cys Glu
     43  44  45  46  47  48  49  50  51  52  53  54  55  56  57  58

5'  AATTATTAGA GCAGTTAGAA CCAGCTCTCA GAACAGGCTC YGATGGCCTG
                                                              500
                              gag
    Lys Leu Leu Glu Gln Leu Glu Pro Ala Leu Arg Thr Gly Ser Asp Gly Leu
     59  60  61  62  63  64  65  66  67  68  69  70  71  72  73  74  75
```

FIGURE 5 B

```
5'  CAGTCTCTTT GGAACACCCT AGTAGTTYTA TGGTGTGTTC ACAAAAGAAT
    +++++|+++++|+++++|+++++|+++++|+++++|+++++|+++++|+++++|+++++|   550
    ................................ gag ................................
    Gln Ser Leu Trp Asn Thr Leu Val Val Leu Trp Cys Val His Lys Arg Ile
    76  77  78  79  80  81  82  83  84  85  86  87  88  89  90  91  92

5'  AGAGATAAGT GACACACAGC AGGCCATTAC AAAATGGAAG GAGGAAATGC
    +++++|+++++|+++++|+++++|+++++|+++++|+++++|+++++|+++++|+++++|   600
    ................................ gag ................................
    Glu Ile Ser Asp Thr Gln Gln Ala Ile Thr Lys Trp Lys Glu Glu Met
    93  94  95  96  97  98  99  100 101 102 103 104 105 106 107 108

5'  AGAAAAGAAA GAAAACATCA GAGGGCAGCA CTGGAACAAG TCAAAACTAT
    +++++|+++++|+++++|+++++|+++++|+++++|+++++|+++++|+++++|+++++|   650
    ................................ gag ................................
    Gln Lys Arg Lys Lys Thr Ser Glu Gly Ser Thr Gly Thr Ser Gln Asn Tyr
    109 110 111 112 113 114 115 116 117 118 119 120 121 122 123 124 125

5'  CCTATCGTGC AGAATGCCCA GGGGCAAATG ACCCATATGC CGCTGTCCCC
    +++++|+++++|+++++|+++++|+++++|+++++|+++++|+++++|+++++|+++++|   700
    ................................ gag ................................
    Pro Ile Val Gln Asn Ala Gln Gly Gln Met Thr His Met Pro Leu Ser Pro
    126 127 128 129 130 131 132 133 134 135 136 137 138 139 140 141 142

5'  CAGGACGCTG AATGCCTGGG TGAAGGCAGT AGAAGAAAAA GCCTTCAACC
    +++++|+++++|+++++|+++++|+++++|+++++|+++++|+++++|+++++|+++++|   750
    ................................ gag ................................
    Arg Thr Leu Asn Ala Trp Val Lys Ala Val Glu Glu Lys Ala Phe Asn
    143 144 145 146 147 148 149 150 151 152 153 154 155 156 157 158

5'  CTGAAATTAT CCCTATGTTT ATGGCCTTGT CAGAAGGGGC TATACCTGAT
    +++++|+++++|+++++|+++++|+++++|+++++|+++++|+++++|+++++|+++++|   800
    ................................ gag ................................
    Pro Glu Ile Ile Pro Met Phe Met Ala Leu Ser Glu Gly Ala Ile Pro Asp
    159 160 161 162 163 164 165 166 167 168 169 170 171 172 173 174 175

5'  GACATCAATA CCATGCTTAA TGCAGTAGGC GGACATCAGG GAGCGTTGCA
    +++++|+++++|+++++|+++++|+++++|+++++|+++++|+++++|+++++|+++++|   850
    ................................ gag ................................
    Asp Ile Asn Thr Met Leu Asn Ala Val Gly Gly His Gln Gly Ala Leu Gln
    176 177 178 179 180 181 182 183 184 185 186 187 188 189 190 191 192
```

FIGURE 5 C

```
5'  GGTGTTGAAA GAGGTAATTA ATGAAGAGGC TGCAGAATGG GATAGAACAC
                                                              900
                              gag
    Val Leu Lys Glu Val Ile Asn Glu Glu Ala Ala Glu Trp Asp Arg Thr
    193 194 195 196 197 198 199 200 201 202 203 204 205 206 207 208

5'  ATCCCGTTCC AGTAGGACCA TTACCACCAG GGCAGCTTAG AGAACCAACA
                                                              950
                              gag
    His Pro Val Pro Val Gly Pro Leu Pro Pro Gly Gln Leu Arg Glu Pro Thr
    209 210 211 212 213 214 215 216 217 218 219 220 221 222 223 224 225

5'  GGAGGGGATA TTGCAGGAAC CACTAGTACC AAACAGGAAC AGATAACCTG
                                                              1000
                              gag
    Gly Gly Asp Ile Ala Gly Thr Thr Ser Thr Lys Gln Glu Gln Ile Thr Trp
    226 227 228 229 230 231 232 233 234 235 236 237 238 239 240 241 242

5'  GATGACAAGG AACAATCCTG TACCAGTAGG GGACATCTAT AGAAARTGGA
                                                              1050
                              gag
    Met Thr Arg Asn Asn Pro Val Pro Val Gly Asp Ile Tyr Arg Lys Trp
    243 244 245 246 247 248 249 250 251 252 253 254 255 256 257 258

5'  TAGTGTTGGG GCTCAATAAA GTGGTAAAAA TGTACTGCCC CGTTAGCATT
                                                              1100
                              gag
    Ile Val Leu Gly Leu Asn Lys Val Val Lys Met Tyr Cys Pro Val Ser Ile
    259 260 261 262 263 264 265 266 267 268 269 270 271 272 273 274 275

5'  CTGGACATAA AGCAGGGACC TAAGGAACCA TTTAGAGATT ATGTAGAYAG
                                                              1150
                              gag
    Leu Asp Ile Lys Gln Gly Pro Lys Glu Pro Phe Arg Asp Tyr Val Asp Arg
    276 277 278 279 280 281 282 283 284 285 286 287 288 289 290 291 292

5'  ATTCTACAAA ACCCTCAGAG CAGAGCAAGC CAGTCAGGAA GTAAAAAGTT
                                                              1200
                              gag
    Phe Tyr Lys Thr Leu Arg Ala Glu Gln Ala Ser Gln Glu Val Lys Ser
    293 294 295 296 297 298 299 300 301 302 303 304 305 306 307 308
```

FIGURE 5 D

```
5'  GGATGACAGA CACCTTACTA GTACAAAATG CTAATCCAGA TTGYAAGCAG    1250
                         gag
    Trp  Met  Thr  Asp   Thr  Leu  Leu   Val  Gln  Asn  Ala   Asn  Pro  Asp   Cys  Lys  Gln
    309  310  311  312   313  314  315   316  317  318  319   320  321  322   323  324  325

5'  ATTTTGAAAG CTCTGGGACC AGGTGCCACC TTAGAAGAAA TGATGAATGC    1300
                         gag
    Ile  Leu  Lys  Ala   Leu  Gly  Pro   Gly  Ala  Thr   Leu  Glu  Glu  Met   Met  Asn  Ala
    326  327  328  329   330  331  332   333  334  335   336  337  338  339   340  341  342

5'  CTGTCAAGGA GTAGGGGGAC CAACACATAA GGCCAGGGTC TTGGCAGAAG    1350
                         gag
    Cys  Gln  Gly   Val  Gly  Gly  Pro   Thr  His  Lys   Ala  Arg  Val   Leu  Ala  Glu
    343  344  345   346  347  348  349   350  351  352   353  354  355   356  357  358

5'  CTATGGCAGC AGCTAATCAA GCTAGCCAAG AATTAAAAGG AGGGTATACA    1400
                         gag
    Ala  Met  Ala  Ala   Ala  Asn  Gln   Ala  Ser  Gln  Glu   Leu  Lys  Gly   Gly  Tyr  Thr
    359  360  361  362   363  364  365   366  367  368  369   370  371  372   373  374  375

5'  ACAGTTTTTA TGCAGAGTGG ACAGAGAAAG CCAGTTAAGT GCTTTAACTG    1450
                         gag
    Thr  Val  Phe  Met   Gln  Ser  Gly   Gln  Arg  Lys   Pro  Val  Lys  Cys   Phe  Asn  Cys
    376  377  378  379   380  381  382   383  384  385   386  387  388  389   390  391  392

5'  TGGAAAAGTA GGACACATAG CAAAGAACTG CAAGGCACCT AGAAGAAGGG    1500
                         gag
    Gly  Lys  Val   Gly  His  Ile  Ala   Lys  Asn  Cys   Lys  Ala  Pro   Arg  Arg  Arg
    393  394  395   396  397  398  399   400  401  402   403  404  405   406  407  408

5'  GRTGTTGGAA GTGTGGACAG GAAGGTCATC AAATGAAAGA CTGCAAATCA    1550
                         gag
    Gly  Cys  Trp  Lys   Cys  Gly  Gln   Glu  Gly  His  Gln   Met  Lys  Asp   Cys  Lys  Ser
    409  410  411  412   413  414  415   416  417  418  419   420  421  422   423  424  425
```

FIGURE 5 E

```
5'  GGAAGACAGG CAAATTTTTT AGGGAAGATC TGGCCTCCGG GGGGCAAGAG
                                                              1600
                              gag
                                        pol
    Gly Arg Gln Ala Asn Phe Leu Gly Lys Ile Trp Pro Pro Gly Gly Lys Arg
    426 427 428 429 430 431 432 433 434 435 436 437 438 439 440 441 442
                    Phe Phe Arg Glu Asp Leu Ala Ser Gly Gly Gln Glu
                     1   2   3   4   5   6   7   8   9  10  11  12

5'  GCCAGGCAAC TATGTACAGA AACAAGTACA ACCGACAGCC CCACCTATGG
                                                              1650
                              gag
                              pol
    Pro Gly Asn Tyr Val Gln Lys Gln Val Gln Pro Thr Ala Pro Pro Met
    443 444 445 446 447 448 449 450 451 452 453 454 455 456 457 458
    Ala Arg Gln Leu Cys Thr Glu Thr Ser Thr Thr Asp Ser Pro Thr Tyr Gly
     13  14  15  16  17  18  19  20  21  22  23  24  25  26  27  28  29

5'  AGGAGGAGGA GATGACTCAG AACAAGCAGA RGGAGGAAAA GGAGGACGAG
                                                              1700
                              gag
                              pol
    Glu Glu Glu Glu Met Thr Gln Asn Lys Gln ??? Glu Glu Lys Glu Asp Glu
    459 460 461 462 463 464 465 466 467 468 469 470 471 472 473 474 475
    Gly Gly Gly Asp Asp Ser Glu Gln Ala Glu Gly Gly Lys Gly Gly Arg
     30  31  32  33  34  35  36  37  38  39  40  41  42  43  44  45

5'  AAAGAGTTGT ACCCTTTAGC CTCCCTCAAA TCACTCTTTG GGACAGACCA
                                                              1750
                              gag
                              pol
    Lys Glu Leu Tyr Pro Leu Ala Ser Leu Lys Ser Leu Phe Gly Thr Asp Gln
    476 477 478 479 480 481 482 483 484 485 486 487 488 489 490 491 492
    Glu Arg Val Val Pro Phe Ser Leu Pro Gln Ile Thr Leu Trp Asp Arg Pro
     46  47  48  49  50  51  52  53  54  55  56  57  58  59  60  61  62
```

FIGURE 5 G

```
5'  AAATTAAAAG CAGGAATGGA TGGGCCTAGG GTGAAGCAAT GGCCCTTGTC
                                                                    2100
                              pol
    Lys Leu Lys Ala  Gly Met Asp  Gly Pro Arg  Val Lys Gln  Trp Pro Leu Ser
    163 164 165 166  167 168 169  170 171 172  173 174 175  176 177 178 179

5'  AAAGGAAAAA ATAGAAGCTT TAAGAGCCAT CTGTCAAGAG ATGGAACAGG
                                                                    2150
                              pol
    Lys Glu Lys  Ie Glu Ala Leu  Arg Ala Ile  Cys Gln Glu  Met Glu Gln
    180 181 182  183 184 185 186 187 188 189  190 191 192  193 194 195

5'  AAGGAAAAAT AACAAAAATT GGGCCTGAAA ATCCATATAA CACCCCCATT
                                                                    2200
                              pol
    Glu Gly Lys Ile  Thr Lys Ile  Gly Pro Glu  Asn Pro Tyr  Asn Thr Pro Ie
    196 197 198 199  200 201 202  203 204 205  206 207 208 209 210 211 212

5'  TTTGCAATAA AAAAGAAAGA TGGCAGCAAG TGGAGGAAAT TAGTAGACTT
                                                                    2250
                              pol
    Phe Ala Ile Lys  Lys Lys Asp  Gly Ser Lys  Trp Arg Lys  Leu Val Asp Phe
    213 214 215 216  217 218 219  220 221 222  223 224 225  226 227 228 229

5'  CAGAGAACTA AATAAAAGAA CACAAGATTT CTGGGAAGTC CAATTGGGRA
                                                                    2300
                              pol
    Arg Glu Leu  Asn Lys Arg  Thr Gln Asp Phe  Trp Glu Val  Gln Leu Gly
    230 231 232  233 234 235  236 237 238 239  240 241 242  243 244 245

5'  TCCCTCATCC AGGAGGTCTT CAGAAAAGRA AATCAGTGAC CATATTAGAT
                                                                    2350
                              pol
    Ie Pro His Pro  Gly Gly Leu  Gln Lys Arg Lys  Ser Val Thr  Ile Leu Asp
    246 247 248 249 250 251 252  253 254 255 256 257 258 259  260 261 262

5'  GTAGGRGATG CTTATTTCTC CTGYCCTTTA GATCCAGATT TTAGAAAATA
                                                                    2400
                              pol
    Val Gly Asp Ala  Tyr Phe Ser  Cys Pro Leu  Asp Pro Asp Phe  Arg Lys Tyr
    263 264 265 266  267 268 269  270 271 272  273 274 275 276  277 278 279
```

FIGURE 5 H

```
5'  TACAGCTTTC ACTATACCTA GTGTAAATAA TGACACACCA GGACTTAGRT   2450
              pol
     Thr Ala Phe Thr Ile Pro Ser Val Asn Asn Asp Thr Pro Gly Leu Arg
     280 281 282 283 284 285 286 287 288 289 290 291 292 293 294 295

5'  ATGTGTAYAA TGTTCTGCCT CAGGGATGGA AGGGATCACC AGCCATTTTY   2500
              pol
     Tyr Val Tyr Asn Val Leu Pro Gln Gly Trp Lys Gly Ser Pro Ala Ile Phe
     296 297 298 299 300 301 302 303 304 305 306 307 308 309 310 311 312

5'  CAGCATTCAA TGACTAAGAT CTTAGAACCC TTTAGRAAGA GTAATCCAGA   2550
              pol
     Gln His Ser Met Thr Lys Ile Leu Glu Pro Phe Arg Lys Ser Asn Pro Glu
     313 314 315 316 317 318 319 320 321 322 323 324 325 326 327 328 329

5'  AGTAGAAATC TAYCAATACA TGGATGATYT ATATGTAGGG TCAGATYTGC   2600
              pol
     Val Glu Ile Tyr Gln Tyr Met Asp Asp Leu Tyr Val Gly Ser Asp Leu
     330 331 332 333 334 335 336 337 338 339 340 341 342 343 344 345

5'  CTTTGTCTGA ACATAGACAG CGGGTAGAGA AACTYAGGGA RCACCTCTAT   2650
              pol
     Pro Leu Ser Glu His Arg Gln Arg Val Glu Lys Leu Arg Glu His Leu Tyr
     346 347 348 349 350 351 352 353 354 355 356 357 358 359 360 361 362

5'  GTATGGGGGT TCACAACTCC TGACAAAAAR CATCAAAAGG AGCCTCCTTT   2700
              pol
     Val Trp Gly Phe Thr Thr Pro Asp Lys Lys His Gln Lys Glu Pro Pro Phe
     363 364 365 366 367 368 369 370 371 372 373 374 375 376 377 378 379

5'  CCTCTGGATG GGATATGAGC TCCATCCTGA CAAGTGGACK GTGCAACCCA   2750
              pol
     Leu Trp Met Gly Tyr Glu Leu His Pro Asp Lys Trp Thr Val Gln Pro
     380 381 382 383 384 385 386 387 388 389 390 391 392 393 394 395
```

FIGURE 5 I

```
5'  TCAAATTACC AGAAAAGGAA AGTTGGACAG TAAATGACAT TCAGAAGCTA                2800
                                    pol
    Ie  Lys Leu Pro  Glu Lys Glu  Ser Trp Thr Val  Asn Asp Ile  Gln Lys Leu
    396 397 398 399  400 401 402  403 404 405 406  407 408 409  410 411 412

5'  GTAGGAAAGT TAAATTGGGC TAGTCAAATT TATCCAGGAA TTACGGTAAA                 2850
                                    pol
    Val Gly Lys Leu  Asn Trp Ala  Ser Gln Ile  Tyr Pro Gly Ile  Arg Val Lys
    413 414 415 416  417 418 419  420 421 422  423 424 425 426  427 428 429

5'  AGAGTTATGY AAACTAATTA GAGGAACTAA RTCCTTAACA GAAGTAGTTG                 2900
                                    pol
    Glu Leu Cys  Lys Leu Ile Arg  Gly Thr Lys  Ser Leu Thr  Glu Val Val
    430 431 432  433 434 435 436  437 438 439  440 441 442  443 444 445

5'  CYTTTACTAG AGAAGCAGAA TTAGAACTAG AGGAAAATAA AGAAATTTTA                 2950
                                    pol
    Ala Phe Thr Arg  Glu Ala Glu  Leu Glu Leu Glu  Glu Asn Lys  Glu Ile Leu
    446 447 448 449  450 451 452  453 454 455 456  457 458 459  460 461 462

5'  AAAGAACCAG TGCATGGAGT TTATTACCAA CCAGAAAAGG AATTAATAGT                 3000
                                    pol
    Lys Glu Pro Val  His Gly Val  Tyr Tyr Gln  Pro Glu Lys Glu  Leu Ile Val
    463 464 465 466  467 468 469  470 471 472  473 474 475 476  477 478 479

5'  AGACATACAG AAACAGGGGG CGGGACAATG GACTTATCAG GTATTCCAGG                 3050
                                    pol
    Asp Ile Gln  Lys Gln Gly Ala  Gly Gln Trp  Thr Tyr Gln  Val Phe Gln
    480 481 482  483 484 485 486  487 488 489  490 491 492  493 494 495

5'  AAGAACATAA AAACTTGAAA ACAGGGAAAT ATGCCAGGCA AAAGGCTACC                 3100
                                    pol
    Glu Glu His Lys  Asn Leu Lys  Thr Gly Lys Tyr  Ala Arg Gln  Lys Ala Thr
    496 497 498 499  500 501 502  503 504 505 506  507 508 509  510 511 512
```

FIGURE 5 J

```
5'  CACACCAATG ATATAAGGCA ACTGGCAGAR GTAATACAGA AGGTATCACA
                                    pol
    His Thr Asn Asp Ile Arg Gln Leu Ala Glu Val Ile Gln Lys Val Ser Gln
    513 514 515 516 517 518 519 520 521 522 523 524 525 526 527 528 529
                                                                            3150

5'  AGAAAGCATA GTGATATGGG GAAAACTACC CAAGTTTAGA CTACCAGTAA
                                    pol
    Glu Ser Ile Val Ile Trp Gly Lys Leu Pro Lys Phe Arg Leu Pro Val
    530 531 532 533 534 535 536 537 538 539 540 541 542 543 544 545
                                                                            3200

5'  ATAGAAATGT GTGGGAGACT TGGTGGTCAG ACTATTGGCA AGCCACCTGG
                                    pol
    Asn Arg Asn Val Trp Glu Thr Trp Trp Ser Asp Tyr Trp Gln Ala Thr Trp
    546 547 548 549 550 551 552 553 554 555 556 557 558 559 560 561 562
                                                                            3250

5'  ATACCTGAGT GGGAATTTGT TAGCACACCC CCTCTTATTA AGCTCTGGTA
                                    pol
    Ile Pro Glu Trp Glu Phe Val Ser Thr Pro Pro Leu Ile Lys Leu Trp Tyr
    563 564 565 566 567 568 569 570 571 572 573 574 575 576 577 578 579
                                                                            3300

5'  TCAGCTAGAA AAAGACCCCA TACCAGGAAC AGAAACCTTT TATGTAGATG
                                    pol
    Gln Leu Glu Lys Asp Pro Ile Pro Gly Thr Glu Thr Phe Tyr Val Asp
    580 581 582 583 584 585 586 587 588 589 590 591 592 593 594 595
                                                                            3350

5'  GGGCAGCAAA CAGAGAGACC AAGTTAGGYA AAGCTGGATA TGTAACAGAT
                                    pol
    Gly Ala Ala Asn Arg Glu Thr Lys Leu Gly Lys Ala Gly Tyr Val Thr Asp
    596 597 598 599 600 601 602 603 604 605 606 607 608 609 610 611 612
                                                                            3400

5'  AGGGGTAGGC AGAAGATAAT CAAACTAGAA GARACAACTA ATCAAAARGC
                                    pol
    Arg Gly Arg Gln Lys Ile Ile Lys Leu Glu Glu Thr Thr Asn Gln Lys Ala
    613 614 615 616 617 618 619 620 621 622 623 624 625 626 627 628 629
                                                                            3450
```

FIGURE 5 K

```
5' AGAATTAGAA GCAGTGTTGT TAGCCTTAAA AGAATCAGGA GAACAGGCTA
                                     pol                              3500
    Glu Leu Glu  Ala Val Leu Leu  Ala Leu Lys  Glu Ser Gly  Glu Gln Ala
    630 631 632  633 634 635 636  637 638 639  640 641 642  643 644 645

5' ACATAGTAAC AGACTCCCAA TATGTGTTAG GRATTATCTC AGCAACTCCA
                                     pol                              3550
    Asn Ile Val Thr  Asp Ser Gln  Tyr Val Leu Gly  Ile Ile Ser  Ala Thr Pro
    646 647 648 649  650 651 652  653 654 655 656  657 658 659  660 661 662

5' GATCAAAGTG ACTCCCCCYT AGTGCAAAAA ATAATAGAAG AAATGACAAA
                                     pol                              3600
    Asp Gln Ser Asp  Ser Pro Leu  Val Gln Lys  Ile Ile Glu Glu  Met Thr Lys
    663 664 665 666  667 668 669  670 671 672  673 674 675 676  677 678 679

5' AAAGGAAAAG GTATACCTRT CATGGGTACC AGCACACAAA GGCATAGGGG
                                     pol                              3650
    Lys Glu Lys  Val Tyr Leu Ser  Trp Val Pro  Ala His Lys  Gly Ile Gly
    680 681 682  683 684 685 686  687 688 689  690 691 692  693 694 695

5' GTAATGARAA YATAGAYAAA TTAGTCAGYA ARGACATTAG AAGAGTGTTA
                                     pol                              3700
    Gly Asn Glu Asn  Ile Asp Lys  Leu Val Ser Lys  Asp Ile Arg  Arg Val Leu
    696 697 698 699  700 701 702  703 704 705 706  707 708 709  710 711 712

5' TTCTTGGAAG GCATAGACCA AGCACAGGAG GATCATGAAA AATATCACAG
                                     pol                              3750
    Phe Leu Glu Gly  Ile Asp Gln  Ala Gln Glu  Asp His Glu Lys  Tyr His Ser
    713 714 715 716  717 718 719  720 721 722  723 724 725 726  727 728 729

5' TAATTGGAGA GCCCTAGCTA GTGARTTTGG CCTTCCACCA ATAGTGGCAA
                                     pol                              3800
    Asn Trp Arg  Ala Leu Ala Ser  Glu Phe Gly  Leu Pro Pro  Ile Val Ala
    730 731 732  733 734 735 736  737 738 739  740 741 742  743 744 745
```

FIGURE 5 L

```
5'  AAGAGATTAT YAACAATTGC CCTAAATGTC ATGTAAAAGG GGAAGCCATG   3850
                                      pol
    Lys Glu Ile Ile  Asn Asn Cys  Pro Lys Cys  His  Val Lys Gly  Glu Ala Met
    746 747 748 749  750 751 752  753 754 755  756  757 758 759  760 761 762

5'  CATGGACAGG TAGACTGCAG TCCAGGAATT TGGCAACTGG ACTGTACCCA   3900
                                      pol
    His Gly Gln Val  Asp Cys Ser  Pro Gly Ile  Trp Gln Leu  Asp Cys Thr His
    763 764 765 766  767 768 769  770 771 772  773 774 775  776 777 778 779

5'  CATGGARGGA AAAATTATCC TCGTGGCAGT CCATGTRGCC AGTGGCTTCA   3950
                                      pol
    Met Glu Gly  Lys Ile Ile  Leu Val Ala Val  His Val Ala  Ser Gly Phe
    780 781 782  783 784 785  786 787 788 789  790 791 792  793 794 795

5'  TGGAAGCAGA AGTAATTCCA GTAGAAACAG GACAAGAAGC TGCATACTTT   4000
                                      pol
    Met Glu Ala Glu  Val Ie Pro  Val Glu Thr  Gly Gln Glu Ala  Ala Tyr Phe
    796 797 798 799  800 801 802  803 804 805  806 807 808 809  810 811 812

5'  GTGCTCAAAT TGGCATCAAG ATGGCCTGTA AAAGTAATAC ACACAGACAA   4050
                                      pol
    Val Leu Lys Leu  Ala Ser Arg  Trp Pro Val  Lys Val Ie  His  Thr Asp Asn
    813 814 815 816  817 818 819  820 821 822  823 824 825  826  827 828 829

5'  TGGGCCTAAC TTTACTAGCG CTGCAGTAAA AGCAGCCTGT TGGTGGCTTA   4100
                                      pol
    Gly Pro Asn  Phe Thr Ser Ala  Ala Val Lys  Ala Ala Cys  Trp Trp Leu
    830 831 832  833 834 835 836  837 838 839  840 841 842  843 844 845

5'  ATATAACTCA TGAGTTTGGG ATACCCTACA ATCCCCAAAG TCAGGGAGTA   4150
                                      pol
    Asn Ile Thr His  Glu Phe Gly  Ile Pro Tyr  Asn Pro Gln Ser  Gln Gly Val
    846 847 848 849  850 851 852  853 854 855  856 857 858 859  860 861 862
```

FIGURE 5 M

```
5'  GTGGAATCAA TGAATAAAGA ATTAAAGAAA ATTATACATC AGGTACGAGA
    ├┼┼┼┼┼┼┼┼┼┤├┼┼┼┼┼┼┼┼┼┤├┼┼┼┼┼┼┼┼┼┤├┼┼┼┼┼┼┼┼┼┤├┼┼┼┼┼┼┼┼┼┤   4200
                                pol
    Val Glu Ser Met Asn Lys Glu Leu Lys Lys  Ile Ile His Gln Val Arg Asp
    863 864 865 866 867 868 869 870 871 872  873 874 875 876 877 878 879

5'  TCAAGCTGAG CACTTAAAGA CAGCAGTTCA AATGGCAGTA TTTGTCCACA
    ├┼┼┼┼┼┼┼┼┼┤├┼┼┼┼┼┼┼┼┼┤├┼┼┼┼┼┼┼┼┼┤├┼┼┼┼┼┼┼┼┼┤├┼┼┼┼┼┼┼┼┼┤   4250
                                pol
    Gln Ala Glu His Leu Lys Thr Ala Val Gln  Met Ala Val Phe Val His
    880 881 882 883 884 885 886 887 888 889  890 891 892 893 894 895

5'  ATTTTAAAAG AAAAGGGGGG ATTGGGGGGT ACACTGCTGG AGACAGGATC
    ├┼┼┼┼┼┼┼┼┼┤├┼┼┼┼┼┼┼┼┼┤├┼┼┼┼┼┼┼┼┼┤├┼┼┼┼┼┼┼┼┼┤├┼┼┼┼┼┼┼┼┼┤   4300
                                pol
    Asn Phe Lys Arg Lys Gly Gly Ile Gly Gly Tyr Thr Ala Gly Asp Arg Ile
    896 897 898 899 900 901 902 903 904 905 906 907 908 909 910 911 912

5'  ATAGATATTC TGGCTACACA RATACAAACA ACAGAATTAC AAAAACAAAT
    ├┼┼┼┼┼┼┼┼┼┤├┼┼┼┼┼┼┼┼┼┤├┼┼┼┼┼┼┼┼┼┤├┼┼┼┼┼┼┼┼┼┤├┼┼┼┼┼┼┼┼┼┤   4350
                                pol
    Ile Asp Ile Leu Ala Thr Gln Ile Gln Thr  Thr Glu Leu Gln Lys Gln Ile
    913 914 915 916 917 918 919 920 921 922  923 924 925 926 927 928 929

5'  TTTAAAAATT CAAAATTTTC AGGTCTATTA CAGAGACAGC AGAGACCCTA
    ├┼┼┼┼┼┼┼┼┼┤├┼┼┼┼┼┼┼┼┼┤├┼┼┼┼┼┼┼┼┼┤├┼┼┼┼┼┼┼┼┼┤├┼┼┼┼┼┼┼┼┼┤   4400
                                pol
    Leu Lys Ile Gln Asn Phe Gln Val Tyr Tyr  Arg Asp Ser Arg Asp Pro
    930 931 932 933 934 935 936 937 938 939  940 941 942 943 944 945

5'  TTTGGAAAGG ACCAGCGACA CTCCTGTGGA AAGGTGAAGG GGCAGTAGTC
    ├┼┼┼┼┼┼┼┼┼┤├┼┼┼┼┼┼┼┼┼┤├┼┼┼┼┼┼┼┼┼┤├┼┼┼┼┼┼┼┼┼┤├┼┼┼┼┼┼┼┼┼┤   4450
                                pol
    Ile Trp Lys Gly Pro Ala Thr Leu Leu Trp  Lys Gly Glu Gly Ala Val Val
    946 947 948 949 950 951 952 953 954 955  956 957 958 959 960 961 962

5'  ATACAAGACA AAGGAGATAT TAAGGTAGTC CCTAGGAGAA AAGCAAAAAT
    ├┼┼┼┼┼┼┼┼┼┤├┼┼┼┼┼┼┼┼┼┤├┼┼┼┼┼┼┼┼┼┤├┼┼┼┼┼┼┼┼┼┤├┼┼┼┼┼┼┼┼┼┤   4500
                                pol
    Ile Gln Asp Lys Gly Asp Ile Lys Val Val  Pro Arg Arg Lys Ala Lys Ile
    963 964 965 966 967 968 969 970 971 972  973 974 975 976 977 978 979
```

FIGURE 5 N

```
5'  AATTAGAAAT TATGGAAAAC AGATGGCAGG TGATGATTGT GTGGCAGATA
                                                                      4550
                             pol
                                    vif
     Ile  Arg  Asn  Tyr  Gly  Lys  Gln  Met  Ala  Gly  Asp  Asp  Cys  Val  Ala  Asp
     980  981  982  983  984  985  986  987  988  989  990  991  992  993  994  995
                    Met  Glu  Asn  Arg  Trp  Gln  Val  Met  Ile  Val  Trp  Gln  Ile
                     1    2    3    4    5    6    7    8    9   10   11   12   13

5'  CCCAGAGAGA AAGTGAAAGC CTGGAACAGT CTGGTTAAAT ATCACAAATA
                                                                      4600
                          pol
                              vif
    Thr  Gln  Arg  Glu  Ser  Glu  Ser  Leu  Glu  Gln  Ser  Gly
    996  997  998  999  1000 1001 1002 1003 1004 1005 1006 1007 1008
    Pro  Arg  Glu  Lys  Val  Lys  Ala  Trp  Asn  Ser  Leu  Val  Lys  Tyr  His  Lys  Tyr
     14   15   16   17   18   19   20   21   22   23   24   25   26   27   28   29   30

5'  TAGGTCTAAA AAGACAAGAA AGTGGTTTTA TAGGCATCAT TATGAGACAA
                                                                      4650
                              vif
    Arg  Ser  Lys  Lys  Thr  Arg  Lys  Trp  Phe  Tyr  Arg  His  His  Tyr  Glu  Thr
     31   32   33   34   35   36   37   38   39   40   41   42   43   44   45   46

5'  CCCATCCTAG GATTAGTTCA GCAGTTTATA TTCCAGTAGG AACAGCAACC
                                                                      4700
                              vif
    Thr  His  Pro  Arg  Ile  Ser  Ser  Ala  Val  Tyr  Ile  Pro  Val  Gly  Thr  Ala  Thr
     47   48   49   50   51   52   53   54   55   56   57   58   59   60   61   62   63

5'  ATTATTGTGA CTACYTATTG GGGGCTCATG CCTGGGGAAA GAGAAGAACA
                                                                      4750
                              vif
    Ile  Ile  Val  Thr  Thr  Tyr  Trp  Gly  Leu  Met  Pro  Gly  Glu  Arg  Glu  Glu  Gln
     64   65   66   67   68   69   70   71   72   73   74   75   76   77   78   79   80

5'  ATTAGGACAT GGAGCAAGTG TGGAGTGGAG ACAAGGTAAA TACACCACAC
                                                                      4800
                              vif
    Leu  Gly  His  Gly  Ala  Ser  Val  Glu  Trp  Arg  Gln  Gly  Lys  Tyr  Thr  Thr
     81   82   83   84   85   86   87   88   89   90   91   92   93   94   95   96
```

FIGURE 5 O

```
5'  AGATAGATCC AGAAACAGCA GATAGGCTAA TTCATCTCCA CTACTTTCAA
                                                                    4850
                              vif
    Gln Ile Asp Pro Glu Thr Ala Asp Arg Leu Ie  His Leu His Tyr Phe Gln
     97  98  99 100 101 102 103 104 105 106 107 108 109 110 111 112 113

5'  TGTTTTTCAG ATTCGGCTGT GAGGAGGGCA ATACTAGGGG ACAGGGTATT
                                                                    4900
                              vif
    Cys Phe Ser Asp Ser Ala Val Arg Arg Ala Ile Leu Gly Asp Arg Val Leu
    114 115 116 117 118 119 120 121 122 123 124 125 126 127 128 129 130

5'  GAAYAMATGT GAATACTCAG CAGGACATAG TCAGGTAGGC TCCTTGCAGT
                                                                    4950
                              vif
    Asn ??? Cys Glu Tyr Ser Ala Gly His Ser Gln Val Gly Ser Leu Gln
    131 132 133 134 135 136 137 138 139 140 141 142 143 144 145 146

5'  ATTTAGCCTT AAAAGTGGTA GTAGGGAAGG TAAARAGGAA GCCACCCCTC
                                                                    5000
                              vif
    Tyr Leu Ala Leu Lys Val Val Val Gly Lys Val Lys Arg Lys Pro Pro Leu
    147 148 149 150 151 152 153 154 155 156 157 158 159 160 161 162 163

5'  CCTAGTGTCC AGATATTGAC ACAAGACATA TGGAGCAACC CCCAGAGGAC
                                                                    5050
                              vif
                                              vpr
    Pro Ser Val Gln Ile Leu Thr Gln Asp Ile Trp Ser Asn Pro Gln Arg Thr
    164 165 166 167 168 169 170 171 172 173 174 175 176 177 178 179 180
                                         Met Glu Gln Pro Pro Glu Asp
                                          1   2   3   4   5   6   7

5'  CAAGGGCCRC CAAGACAGCC ATTCAATGAG TGGATGCTAC AAACCTTAGA
                                                                    5100
                              vif
                              vpr
    Lys Gly ??? Gln Glu Ser His Ser Met Ser Gly Cys Tyr Lys Pro .
    181 182 183 184 185 186 187 188 189 190 191 192 193 194 195 196
    Gln Gly Pro Pro Arg Glu Pro Phe Asn Glu Trp Met Leu Gln Thr Leu Glu
     8   9  10  11  12  13  14  15  16  17  18  19  20  21  22  23  24
```

FIGURE 5 P

```
5' GGAACTCAAG GAGGAAGCAG TAAGACACTT CCCTAGGCCT TGGTTACACT        5150
                                   vpr
   Glu Leu Lys  Glu Glu Ala Val  Arg His Phe  Pro Arg Pro  Trp Leu His
    25  26  27   28  29  30  31   32  33  34   35  36  37   38  39  40

5' CATTAGGACA GTATATCTAT AATACCTATG GGCACACCTG GGAGGCAGTA        5200
                                   vpr
   Ser Leu Gly Gln  Tyr Ile Tyr  Asn Thr Tyr  Gly Asp Thr Trp  Glu Gly Val
    41  42  43  44   45  46  47   48  49  50   51  52  53  54   55  56  57

5' ACTGCAATTA TTAGGATCCT ACAACAATTA ATYTTTATCC ATTATAGAAT        5250
                                   vpr
   Thr Ala Ile Ile  Arg Ile Leu  Gln Gln Leu  Ile Phe Ile His  Tyr Arg Ile
    58  59  60  61   62  63  64   65  66  67   68  69  70  71   72  73  74

5' TGGATGCCAA CATAGTAGAA TAGGTATCTT GACACCCTCT CGAAGAGGAA        5300
                                   vpr
   Gly Cys Gln  His Ser Arg Ile  Gly Ile Leu  Thr Pro Ser  Arg Arg Gly
    75  76  77   78  79  80  81   82  83  84   85  86  87   88  89  90

5' GGAGACATGG ACCCAGTAGA TCCTGATCTG CCTCCATGGC AACAGCCAGG        5350
               vpr
                                    tat
   Arg Arg His Gly  Pro Ser Arg  Ser
    91  92  93  94   95  96  97   98  99
                    Met Asp  Pro Val Asp  Pro Asp Leu  Pro Pro Trp  Gln Gln Pro Gly
                      1   2    3   4   5    6   7   8    9  10  11   12  13  14  15

5' GAGTCAGCCC TCAAGCCCAT GTAACAATTG CTACTGCAAA GCCTGCTGCT        5400
                                   tat
   Ser Gln Pro  Ser Ser Pro Cys  Asn Asn Cys  Tyr Cys Lys  Ala Cys Cys
    16  17  18   19  20  21  22   23  24  25   26  27  28   29  30  31
```

FIGURE 5 R

```
5'  CTGTATAGTA GYTTGGGGGA AGGTCCTYCT ATTAGTGCTA AAAGAAAGAG
    ++++|++++| ++++|++++| ++++|++++| ++++|++++| ++++|++++|  5650
                            vpu
                            rev
                            tat
    Cys  Ile  Val  ???  Trp  Gly  Lys  Val  Leu  Leu  Leu  Val  Leu  Lys  Glu  Arg
     19   20   21   22   23   24   25   26   27   28   29   30   31   32   33   34

5'  AAAGRGATAA GTTTGTRCAA AGGCTAGCAA GGTGGAGAGA AGGGCAAGAA
    ++++|++++| ++++|++++| ++++|++++| ++++|++++| ++++|++++|  5700
                            vpu
                            rev
                            tat
    Glu  Arg  Asp  Lys  Phe  Val  Gln  Arg  Leu  Ala  Arg  Trp  Arg  Glu  Gly  Gln  Glu
     35   36   37   38   39   40   41   42   43   44   45   46   47   48   49   50   51

5'  GATGAGGGGT ATGAAAGTAA TGAAGAAGAA GAAGAACAGC TTAGGGAACT
    ++++|++++| ++++|++++| ++++|++++| ++++|++++| ++++|++++|  5750
                            env
                            vpu
                            rev
                            tat
    Asp  Glu  Gly  Tyr  Glu  Ser  Asn  Glu  Glu  Glu  Glu  Glu  Gln  Leu  Arg  Glu  Leu
     52   53   54   55   56   57   58   59   60   61   62   63   64   65   66   67   68
    Met  Arg  Gly  Met  Lys  Val  Met  Lys  Lys  Lys  Lys  Asn  Ser  Leu  Gly  Asn
      1    2    3    4    5    6    7    8    9   10   11   12   13   14   15   16
```

FIGURE 5 T

```
5'  AGCAGCATAA TATTTGGGCC ACCCAGGCCT GTGTGCCCAC AGACCCTAGA
                                                                    5950
                              env
                              rev
                              tat
    Glu Gln His Asn Ile Trp Ala Thr Gln Ala Cys Val Pro Thr Asp Pro Arg
    67  68  69  70  71  72  73  74  75  76  77  78  79  80  81  82  83

5'  CCAATAGAGG TCAGGATAGA TAATGTAACA GAGTCTTTTA ATATTTGGGA
                                                                    6000
                              env
                              rev
                              tat
    Pro Ile Glu Val Arg Ile Asp Asn Val Thr Glu Ser Phe Asn Ile Trp Asp
    84  85  86  87  88  89  90  91  92  93  94  95  96  97  98  99  100

5'  CAATTATATG GTGACACAAA TGCAGGAAGA CATCATTAGC TTATGGGATC
                                                                    6050
                              env
                              rev
                              tat
    Asn Tyr Met Val Thr Gln Met Gln Glu Asp Ile Ile Ser Leu Trp Asp
    101 102 103 104 105 106 107 108 109 110 111 112 113 114 115 116
```

FIGURE 5 U

```
5'  AGAGCCTTAA ACCTTGTGTA AAATTGACAG TTCTATGTGT TACTATGRAT
    +++++++++|++++++++++|++++++++++|++++++++++|++++++++++|  6100
                             env
                             rev
                             tat
    Gln  Ser  Leu  Lys  Pro  Cys  Val  Lys  Leu  Thr  Val  Leu  Cys  Val  Thr  Met  ???
    117  118  119  120  121  122  123  124  125  126  127  128  129  130  131  132  133

5'  TGTAGCGACT GCAGCACGGT TCACTGTACT AATAACTCCT CCAGGGTTAA
    +++++++++|++++++++++|++++++++++|++++++++++|++++++++++|  6150
                             env
                             rev
                             tat
    Cys  Ser  Asp  Cys  Ser  Thr  Val  Asp  Cys  Thr  Asn  Asn  Ser  Ser  Arg  Val  Asn
    134  135  136  137  138  139  140  141  142  143  144  145  146  147  148  149  150

5'  TAACAGCACC GACAGCACCA ACACCAGCAA AACCAATCCA TTAGAATTAT
    +++++++++|++++++++++|++++++++++|++++++++++|++++++++++|  6200
                             env
                             rev
                             tat
         Asn  Ser  Thr  Asp  Ser  Thr  Asn  Thr  Ser  Lys  Thr  Asn  Pro  Leu  Glu  Leu
         151  152  153  154  155  156  157  158  159  160  161  162  163  164  165  166
```

FIGURE 5 V

```
5'  TTCAGTGCAG TTTTAATACA ACCACAATAG TAAAAGATAA ACAGCAGACA
    +--+--+--+--+--+--+--+--+--+--+--+--+--+--+--+--+--+--+--+--+  6250
    ─────────────────────────── env ───────────────────────────
    ─────────────────────────── rev ───────────────────────────
    ─────────────────────────── tat ───────────────────────────
    Phe  Gln  Cys  Ser  Phe  Asn  Thr  Thr  Thr  Ile  Val  Lys  Asp  Lys  Gln  Gln  Thr
    167  168  169  170  171  172  173  174  175  176  177  178  179  180  181  182  183
```

```
5'  CAGCAAGCAC TCTTTTATAG AGCAGACCTA ACAAAATTGG ATAATGACAA
    +--+--+--+--+--+--+--+--+--+--+--+--+--+--+--+--+--+--+--+--+  6300
    ─────────────────────────── env ───────────────────────────
    ─────────────────────────── rev ───────────────────────────
    ─────────────────────────── tat ───────────────────────────
    Gln  Gln  Ala  Leu  Phe  Tyr  Arg  Ala  Asp  Leu  Thr  Lys  Leu  Asp  Asn  Asp  Asn
    184  185  186  187  188  189  190  191  192  193  194  195  196  197  198  199  200
```

```
5'  TAGTACATAT AGATTAATTA ATTGCAACAC CACTACCATT ACACAGGCAT
    +--+--+--+--+--+--+--+--+--+--+--+--+--+--+--+--+--+--+--+--+  6350
    ─────────────────────────── env ───────────────────────────
    ─────────────────────────── rev ───────────────────────────
    ─────────────────────────── tat ───────────────────────────
    Ser  Thr  Tyr  Arg  Leu  Ile  Asn  Cys  Asn  Thr  Thr  Thr  Ile  Thr  Gln  Ala
    201  202  203  204  205  206  207  208  209  210  211  212  213  214  215  216
```

FIGURE 5 W

```
5'  GCCCAAAAGT GAACTTTGAG CCGCTACCCA TACAGTATTG TGCACCAGCA
                                                              6400
                              env
                              rev
                              tat
    Cys Pro Lys Val  Asn Phe Glu  Pro Leu Pro  Ile Gln Tyr Cys  Ala Pro Ala
    217 218 219 220  221 222 223  224 225 226  227 228 229 230  231 232 233

5'  GGGTATGCAC TAATGAAATG CAATCAGACA GGATTTAATG GTACAGGACC
                                                              6450
                              env
                              rev
                              tat
    Gly Tyr Ala Leu  Met Lys Cys  Asn Gln Thr  Gly Phe Asn Gly  Thr Gly Pro
    234 235 236 237  238 239 240  241 242 243  244 245 246     247 248 249 250

5'  TTGTAATAAG ACAGTTATAA CACACTGTAC ACATGGAATT AAGCCAACAG
                                                              6500
                              env
                              rev
                              tat
    Cys Asn Lys  Thr Val Ile  Thr His Cys  Thr His Gly Ile  Lys Pro Thr
    251 252 253  254 255 256  257 258 259  260 261 262 263  264 265 266
```

FIGURE 5 X

```
5'  TGTCAACACA ATTAATACTC AATGGAACTC TAGCAAAGGG AGAGCCCTTA
                                                            6550
                         env
                         rev
                         tat
    Val Ser Thr Gln Leu Ie  Leu Asn Gly Thr Leu Ala Lys Gly Glu Pro Leu
    267 268 269 270 271 272 273 274 275 276 277 278 279 280 281 282 283

5'  GTAATTACTC AGAATGTGTC AGATACAGGA AAAGTCATCA TAGTAAAATT
                                                            6600
                         env
                         rev
                         tat
    Val Ie  Thr Gln Asn Val Ser Asp Thr Gly Lys Val Ie  Ile Val Lys Leu
    284 285 286 287 288 289 290 291 292 293 294 295 296 297 298 299 300

5'  AAATGAGAGT GTGTCACTCA CCTGTATAAG ACCAGGTAAT AACACAAGAG
                                                            6650
                         env
                         rev
                         tat
    Asn Glu Ser Val Ser Leu Thr Cys Ie  Arg Pro Gly Asn Asn Thr Arg
    301 302 303 304 305 306 307 308 309 310 311 312 313 314 315 316
```

FIGURE 5 Z

```
5'  CCAACcATAC ATCCAAACAc AACCATACAT TTgTTTTTAA AAACAGTACA
    +++++++++|+++++++++|+++++++++|+++++++++|+++++++++|  6850
                            env
                            rev
                            tat
    Ser  Asn  His  Thr  Ser  Lys  His  Asn  His  Thr  Phe  Val  Phe  Lys  Asn  Ser  Thr
    367  368  369  370  371  372  373  374  375  376  377  378  379  380  381  382  383

5'  GGGGGAGACC CAGAGGTTTC TTCGCTGCAC TTCAGTTGTC ATGGGGAATT
    +++++++++|+++++++++|+++++++++|+++++++++|+++++++++|  6900
                            env
                            rev
                            tat
    Gly  Gly  Asp  Pro  Glu  Val  Ser  Ser  Leu  His  Phe  Ser  Cys  His  Gly  Glu  Phe
    384  385  386  387  388  389  390  391  392  393  394  395  396  397  398  399  400

5'  CTTTTATTGT AACACCAGCA GCCTGTTTAA CTTTAGTTAT ACTTGGAATG
    +++++++++|+++++++++|+++++++++|+++++++++|+++++++++|  6950
                            env
                            rev
                            tat
    Phe  Tyr  Cys  Asn  Thr  Ser  Ser  Leu  Phe  Asn  Phe  Ser  Tyr  Thr  Trp  Asn
    401  402  403  404  405  406  407  408  409  410  411  412  413  414  415  416
```

FIGURE 5 BB

```
5'  TTACAGGTTT AATGTTAGAA AGAGAACTAC CTTACAATGA CAGCAGCAAG
    +++++|+++++|+++++|+++++|+++++|+++++|+++++|+++++|+++++|+++++|  7150
                          ······ env ······
    ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
                          ······ rev ······
                          ······ tat ······
    Ile Thr Gly Leu  Met Leu Glu  Arg Glu Leu Pro  Tyr Asn Asp  Ser Ser Lys
    467 468 469 470  471 472 473  474 475 476      477 478 479 480  481 482 483
```

```
5'  AACACCACTT TAAGTCCTAT AGGGGGAGAC ATGACAAATA TCTGGAGAAG
    +++++|+++++|+++++|+++++|+++++|+++++|+++++|+++++|+++++|+++++|  7200
                          ······ env ······
    ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
                          ······ rev ······
                          ······ tat ······
    Asn Thr Thr Leu  Ser Pro Ile  Gly Gly Asp  Met Thr Asn Ile  Trp Arg Ser
    484 485 486 487  488 489 490  491 492 493  494 495 496 497  498 499 500
```

```
5'  TGAGTTATAT CCCTACAAAG TAGTTCAAGT AAAAGCTCTG GCCGTGGCAC
    +++++|+++++|+++++|+++++|+++++|+++++|+++++|+++++|+++++|+++++|  7250
                          ······ env ······
    ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓
                          ······ rev ······
                          ······ tat ······
    Glu Leu Tyr  Pro Tyr Lys Val  Val Gln Val  Lys Ala Leu  Ala Val Ala
    501 502 503  504 505 506 507  508 509 510  511 512 513  514 515 516
```

FIGURE 5 EE

```
5'  TAGGACTGTG GGGATGCTCA GGACAAATAR TATGTTATAC TAATGTGCCA
    +++++|++++| +++++|++++| +++++|++++| +++++|++++| +++++|++++|  7600
                              env
                              rev
                              tat Leu  Gly  Leu  Trp  Gly  Cys  Ser  Gly  Gln  Ile  ???  Cys  Tyr  Thr  Asn  Val  Pro
    617  618  619  620  621  622  623  624  625  626  627  628  629  630  631  632  633
```

```
5'  TGGAATAGTA CCTGGACCAA CAAAAATGAA ACAGAATTAG ATGGCATTTG
    +++++|++++| +++++|++++| +++++|++++| +++++|++++| +++++|++++|  7650
                              env
                              rev
                              tat Trp  Asn  Ser  Thr  Trp  Thr  Asn  Lys  Asn  Glu  Thr  Glu  Leu  Asp  Gly  Ile  Trp
    634  635  636  637  638  639  640  641  642  643  644  645  646  647  648  649  650
```

```
5'  GGGTAATCTA ACATGGCAGG AGTGGGACAA ACTGGTGGAT AATTACACTG
    +++++|++++| +++++|++++| +++++|++++| +++++|++++| +++++|++++|  7700
                              env
                              rev
                              tat Gly  Asn  Leu  Thr  Trp  Gln  Glu  Trp  Asp  Lys  Leu  Val  Asp  Asn  Tyr  Thr
    651  652  653  654  655  656  657  658  659  660  661  662  663  664  665  666
```

FIGURE 5 FF

```
5'  ACACAATTTA CTTGGAAATA CAGAAAGCAC AAGAGCAGCA GAAGGAAAAT
    ++++|++++|  ++++|++++| ++++|++++| ++++|++++| ++++|++++|   7750
                              env
                              rev
                              tat Asp  Thr  Ile  Tyr  Leu  Glu  Ile  Gln  Lys  Ala  Gln  Glu  Gln  Gln  Lys  Glu  Asn
    667  668  669  670  671  672  673  674  675  676  677  678  679  680  681  682  683

5'  GAAAGAAAGC TATTAGAATT AGACAAATGG GCACAATTGT GGAGCTGGAT
    ++++|++++|  ++++|++++| ++++|++++| ++++|++++| ++++|++++|   7800
                              env
                              rev
                              tat Glu  Arg  Lys  Leu  Leu  Glu  Leu  Asp  Lys  Trp  Ala  Gln  Leu  Trp  Ser  Trp  Met
    684  685  686  687  688  689  690  691  692  693  694  695  696  697  698  699  700

5'  GGACATAACA AAATGGTTGT GGTACATAAA AATTTTCATT ATGATAGTAG
    ++++|++++|  ++++|++++| ++++|++++| ++++|++++| ++++|++++|   7850
                              env
                              rev
                              tat Asp  Ile  Thr  Lys  Trp  Leu  Trp  Tyr  Ile  Lys  Ile  Phe  Ile  Met  Ile  Val
    701  702  703  704  705  706  707  708  709  710  711  712  713  714  715  716
```

FIGURE 5 II

```
5'  TGCTATATCA GTTGCAAATT GGACTGATCA AGTAATAGCA GTAGGGCAAC  8300
                                    env
    Ala  Ile  Ser  Val  Ala  Asn  Trp  Thr  Asp  Gln  Val  Ile  Ala  Val  Gly  Gln
    851  852  853  854  855  856  857  858  859  860  861  862  863  864  865  866

5'  AAATAGGAAG AGGCTTCTTG AACATACCAA GAAGGTTAAG ACAAGGGCTA  8350
                                    env
    Gln  Ile  Gly  Arg  Gly  Phe  Leu  Asn  Ile  Pro  Arg  Arg  Leu  Arg  Gln  Gly  Leu
    867  868  869  870  871  872  873  874  875  876  877  878  879  880  881  882  883

5'  GAAAGAAGCT TACTGTAAAA TGGGGAATGC ATGGAAGAAA AGTAGCTTAG  8400
                    env                              nef
    Glu  Arg  Ser  Leu  Leu          Met  Gly  Asn  Ala  Trp  Lys  Lys  Ser  Ser  Leu
    884  885  886  887  888  889      1    2    3    4    5    6    7    8    9   10

5'  TGGGCTGGCC AGCAGTCAGG GAAAAAATAA AGCAGACTAC CCCGACTACC  8450
                                    nef
    Val  Gly  Trp  Pro  Ala  Val  Arg  Glu  Lys  Ile  Lys  Gln  Thr  Thr  Pro  Thr  Thr
     11   12   13   14   15   16   17   18   19   20   21   22   23   24   25   26   27

5'  CCTGACCCGA CTACCCCAGT AACACCTGCA CCCGGGGTTG GGGAAATTTC  8500
                                    nef
    Pro  Asp  Pro  Thr  Thr  Pro  Val  Thr  Pro  Ala  Pro  Gly  Val  Gly  Glu  Ile  Ser
     28   29   30   31   32   33   34   35   36   37   38   39   40   41   42   43   44

5'  CAAAGAATTA GCACAAGGAA AAGGAATACC CAGTAAATTT AGTTCAAAGA  8550
                                    nef
    Lys  Glu  Leu  Ala  Gln  Gly  Lys  Gly  Ile  Pro  Ser  Lys  Phe  Ser  Ser  Lys
     45   46   47   48   49   50   51   52   53   54   55   56   57   58   59   60

5'  ACAATGCAGC ATTGGCCTTC TTGGATGCTC ATGAGGAAGA AGAAGTAGGR  8600
                                    nef
    Asn  Asn  Ala  Ala  Leu  Ala  Phe  Leu  Asp  Ala  His  Glu  Glu  Glu  Val  Gly
     61   62   63   64   65   66   67   68   69   70   71   72   73   74   75   76   77
```

FIGURE 5 JJ

```
5'  TTCCCAGTCA GGCCTCAAGT ACCCTTAAGA TGCATGACAT ACAAGGCAGC   8650
                               nef
    Phe Pro Val Arg  Pro Gln Val  Pro Leu Arg  Cys Met Thr Tyr  Lys Ala Ala
    78  79  80  81   82  83  84   85  86  87   88  89  90  91   92  93  94

5'  ATTTGACCTC AGCTTCTTTT TAAAAGAAAA GGGAGGACTG GATGGGTTAG   8700
                               nef
    Phe Asp Leu  Ser Phe Phe Leu  Lys Glu Lys  Gly Gly Leu  Asp Gly Leu
    95  96  97   98  99  100 101  102 103 104  105 106 107  108 109 110

5'  TTTACTCACC TGAGAGAGCA GAGATCCTAG ATCTCTGGAT CTATCACACT   8750
                               nef
    Val Tyr Ser Pro  Glu Arg Ala  Glu Ile Leu  Asp Leu Trp Ile  Tyr His Thr
    111 112 113 114  115 116 117  118 119 120  121 122 123 124  125 126 127

5'  CAGGGATTCT TCCCTGACTG GCAGAATTAC ACTCCAGGGC CAGGAGAAAG   8800
                               nef
    Gln Gly Phe Phe  Pro Asp Trp  Gln Asn Tyr  Thr Pro Gly Pro  Gly Glu Arg
    128 129 130 131  132 133 134  135 136 137  138 139 140 141  142 143 144

5'  ATATCCCCTG ACCTTTGGGT GGCTGTTTAA ACTAGTACCA GTCTCTGAGG   8850
                               nef
    Tyr Pro Leu  Thr Phe Gly Trp  Leu Phe Lys  Leu Val Pro  Val Ser Glu
    145 146 147  148 149 150 151  152 153 154  155 156 157  158 159 160

5'  TAGAAGCTGA GGAAATGGGA GATAAGCAGG AGAAAGCTAA GCTGCTACAT   8900
                               nef
    Val Glu Ala Glu  Glu Met Gly  Asp Lys Gln  Glu Lys Ala Lys  Leu Leu His
    161 162 163 164  165 166 167  168 169 170  171 172 173 174  175 176 177

5'  CCAGCCTGCA CTTATGGGTT TTCAGATCCT CATAAGGAGA TCCTAGTGTG   8950
                               nef
    Pro Ala Cys Thr  Tyr Gly Phe  Ser Asp Pro  His Lys Glu Ile  Leu Val Trp
    178 179 180 181  182 183 184  185 186 187  188 189 190 191  192 193 194
```

FIGURE 5 KK

```
5'  GAAGTTTGAC AGCTCACTTG GAAGAGAACA TGTTGCCTTA CAAAAGCACC
                                                              9000
                           nef
    Lys Phe Asp  Ser Ser Leu Gly  Arg Glu His  Val Ala Leu  Gln Lys His
    195 196 197  198 199 200  201 202 203 204  205 206 207  208 209 210

5'  CGGAACTGTT TATTAAAGAC TAAATTGCTG ACGCCACGTA GCTGCTAAAG
                                                              9050
                     nef
    Pro Glu Leu Phe  Ile Lys Asp  .
    211 212 213 214  215 216 217  218

5'  CTGCTGACAC TGCAGGGACT TTCCGGGGAC GGAAAGTCCC GACGGCGGAA
                                                              9100

5'  CAAGGGGAGG AGCAGGGGAG TGGTTTCACC CTCAGAGCTG CATATAAGCA
                                                              9150

5'  GCTGCTTCAC GCTTGTACTG GGTCTCTGTG ACAGACCAGA TTAGAGCCTG
                                                              9200

5'  GGAGCTCTCT GGTCTAAGCA GAACCCACTG GTTAAAAA
                                                              9238
```

Figure 6.

```
                            10         20         30         40         50
U14788 (Native)      GAATTCCATG AAAGCCAAGC AATTATTGCA TGGTATAGTG CAGCAGCAGA
HLH-P rAg            ---------- -----A--A- -GC-TC---- ------C--T ----------
Translated protein          M   K  A  K  Q   L  L  H   G  I  V   Q  Q  Q  N 60         70         80         90        100
U14788 (Native)      ACAATATGCT AAGAGCTATA GAGGCACAGC AAGAATTGCT GAGACTCTCT
HLH-P rAg            ----C----- GC-T-----C --A--T---- -G---C---- -C-T--G---
Translated protein       N  M  L   R  A  I   E  A  Q  Q   E  L  L   R  L  S 110        120        130        140        150
U14788 (Native)      GTGTGGGGCA TAAGACAGCT CCGAGCTCGC CTGCTTGCCA TTGAAACCTA
HLH-P rAg            --T-----T- -CC-T----- T--T-----T -----G--T- -C--------
Translated protein    V  W  G  I   R  Q  L   R  A  R   L  L  A  I   E  T  Y 160        170        180        190        200
U14788 (Native)      TTTAAGGGAT CAGCAACTCC TAGGACTGTG GGGATGCTCA GGACAAATAG
HLH-P rAg            CC-GC-T--C -----G--G- -G--T----- ---T-----T --T--G--C-
Translated protein     L  R  D   Q  Q  L  L   G  L  W   G  C  S   G  Q  I  V 210        220        230        240        250
U14788 (Native)      TATGTTATAC TAATGTGCCA TGGAATAGTA CCTGGACCAA CAAAAATGAA
HLH-P rAg            -T--C--C-- ---C-T--G- -----CTC-- -T-----T-- ------C---
Translated protein     C  Y  T   N  V  P   W  N  S   T  W  T  N   K  N  E 260        270        280        290        300
U14788 (Native)      ACAGAATTAG ATGGCATTTG GGGTAATCTA ACATGGCAGG AGTGGGACAA
HLH-P rAg            --T---C-G- -C--T--C-- ------C--G --T------- -A--------
Translated protein     T  E  L  D   G  I  W   G  N  L   T  W  Q   E  W  D  K 310        320        330        340        350
U14788 (Native)      ACTGGTGGAT AATTACACTG ACACAATTTA CTTGGAAATA CAGAAAGCAC
HLH-P rAg            ---------C --C---A--- -------C-- ---------C --A-------
Translated protein     L  V  D   N  Y  T  D   T  I  Y   L  E  I   Q  K  A  Q 360        370        380        390        400
U14788 (Native)      AAGAGCAGCA GAAGGAAAAT GAAAGAAAGC TATTAGAATT AGACAAATGG
HLH-P rAg            -G--A----- ---A------C ---C-T--A- -TC-C---C- G---------
Translated protein     E  Q  Q   K  E  N   E  R  K  L   L  E  L   D  K  W 410        420        430
U14788 (Native)      GAGCACCACC ACCACCACCA CTAATAGGAT CC
HLH-P rAg            ---------- ---------- ---------- --
Translated protein     E  H  H  H   H  H  H    .  .
```

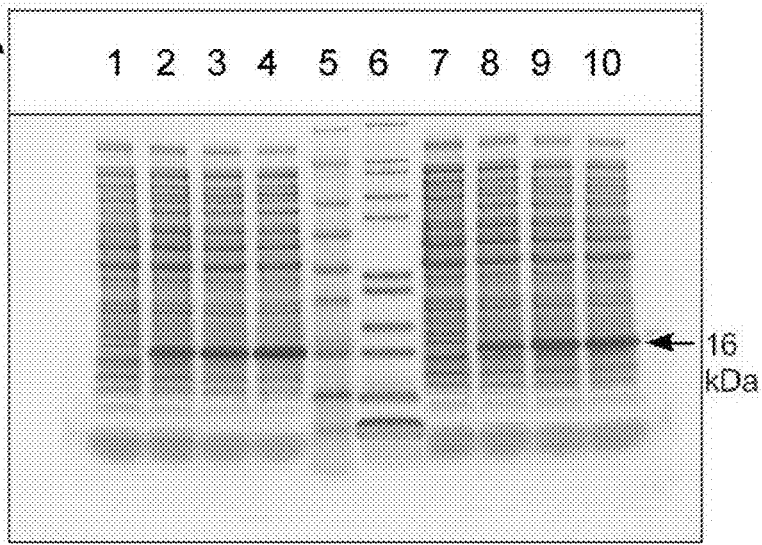
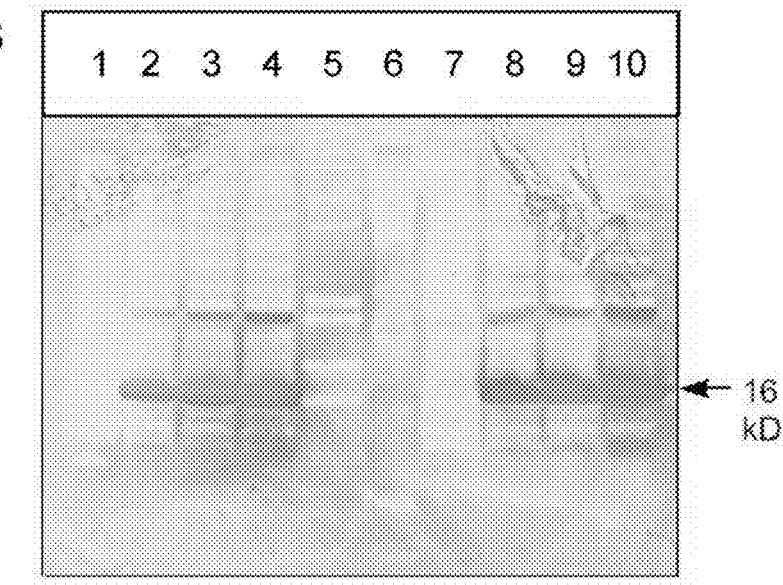

Figure 10.

| Antigens | Plasma Specimens | | | | | |
|---|---|---|---|---|---|---|
| | 1 | 2 | 3 | 4 | 5 | 6 |
| HLH-M, 10µg/ml | | ■ | ■ | | ■ | ■ |
| HLH-M, 25µg/ml | | ■ | ■ | | ■ | ■ |
| HLH-O, 10µg/ml | | ■ | ■ | | ■ | ■ |
| HLH-O, 25µg/ml | | ■ | ■ | | ■ | ■ |
| HLH-2, 10µg/ml | | | ■ | ■ | | ■ |
| HLH-2, 25µg/ml | | ■ | ■ | ■ | | ■ |
| HLH-P, 10µg/ml | | ■ | ■ | | ■ | ■ |
| HLH-P, 25µg/ml | | ■ | ■ | | ■ | ■ |

HUMAN IMMUNODEFICIENCY VIRUS AND USES THEREOF

This application claims priority to U.S. Provisional Application Nos. 61/304,918, filed on Feb. 16, 2010 and 61/376,151, filed on Aug. 23, 2010.

SEQUENCE LISTING

The instant application contains a Sequence Listing which has been submitted electronically in ASCII format and is hereby incorporated by reference in its entirety. Said ASCII copy, created on Apr. 15, 2015, is named 10364USO1_SL.txt and is 78,329 bytes in size.

FIELD OF THE INVENTION

The present invention relates to Human Immunodeficiency Virus-1 (HIV-1) Group P and fragments thereof, primers which are derived from HIV-1 Group P, immunogenic regions thereof, immunoassays and nucleic acid based assays for the detection of Human Immunodeficiency Virus (HIV) that employ said HIV-1 Group P or fragments thereof and therapeutic compositions containing said HIV-1 Group P or fragments thereof.

BACKGROUND OF THE INVENTION

The human acquired immunodeficiency viruses HIV-1 and HIV-2 are retrolentiviruses, which are viruses found in a large number of African primates. The origin of HIV-2 appears to be clear on account of its strong homology with the Sooty Mangabey (West Africa) virus. However, the origins of HIV-1 are less clear. Type 1 HIV viruses have been subdivided into three groups, i.e. the M (major) group, an O (outlier) group and N group (non-M, non-O). Each group appears to represent a separate transmission of a simian immunodeficiency virus (SIV) from nonhuman primates into humans; groups M and N appear to have originated in chimpanzees (Pan troglodytes troglodytes). The origin of group O is unknown; the closest known nonhuman virus to group O is an SIV identified in western gorillas (Gorilla gorilla gorilla) however, group O and SIVgor form genetically distinct lineages. In August 2009, Plantier, et al. reported the identification and partial genome sequence of HIV-1 group P (hereinafter "RBF168"), a virus that is most closely related to and that appears to have originated from SIVgor (Plantier J-C, Leoz M, Dickerson J E, et al. (2009) Nature Medicine 15:871-872). To date just this single group P virus has been reported. However, the genome of this new variant was not fully sequenced. The genetic diversity of HIV-1 has the potential to impact blood screening, diagnostics, therapeutic monitoring, resistance to antiretroviral agents, vaccine development, and pathogenesis of HIV. The demonstration of new variants is important for developing sufficiently sensitive and specific reagents for detecting HIV infections, that is to say reagents which do not lead to false-negative or false-positive results, and for developing compositions which are protective in regard to HIV-1 subtypes which do not belong either to the M group, the O group or to the N group.

BRIEF SUMMARY OF THE INVENTION

One embodiment of the present invention relates to the complete nucleotide sequence of a HIV-1 Group P designated as strain 06CMU14788 (SEQ ID NO: 1) as well as to nucleic acid fragments which are at least 10 nucleotides in size and which are derived from the said strain.

In one embodiment, the present invention relates to a HIV-1 Group P gag nucleic acid as described in SEQ ID NO: 2. In another embodiment, the present invention relates to a HIV-1 Group P pol nucleic acid as described in SEQ ID NO: 3. In another embodiment, the present invention relates to a HIV-1 Group P vif nucleic acid as described in SEQ ID NO: 4. In another embodiment, the present invention relates to a HIV-1 Group P vpr nucleic acid as described in SEQ ID NO: 5. In another embodiment, the present invention relates to a HIV-1 Group P tat nucleic acid as described in SEQ ID NO: 6. In another embodiment, the present invention relates to a HIV-1 Group P rev nucleic acid as described in SEQ ID NO: 7. In another embodiment, the present invention relates to a HIV-1 Group P vpu nucleic acid as described in SEQ ID NO: 8. In another embodiment, the present invention relates to a HIV-1 Group P env nucleic acid as described in SEQ ID NO: 9. In another embodiment, the present invention relates to a HIV-1 Group P nef nucleic acid as described in SEQ ID NO: 10.

Such sequences can be used in the specific identification of a HIV-1 Group P virus, and as diagnostic reagents, either alone or pooled with other reagents, for the differential identification of any HIV-1. The invention also relates to the use of the above described sequences for implementing a method of hybridization and/or gene amplification of nucleic acid sequences of HIV-1 Group P, with these methods being applicable to the in-vitro diagnosis of the potential infection of an individual with a HIV-1 Group P virus.

This in-vitro diagnostic method is carried out using a test sample and comprises: a step of extracting the nucleic acid which is to be detected and which belongs to the genome of the virus, which virus may possibly be present in the test sample, and, where appropriate, a step of treating the nucleic acid using a reverse transcriptase, if this nucleic acid is in RNA form, at least one cycle comprising the steps of denaturing the nucleic acid, of hybridizing with at least one sequence in accordance with the invention and, where appropriate, extending the hybrid, which has been formed, in the presence of suitable reagents (polymerizing agent, such as DNA polymerase and dNTP), and a step of detecting the possible presence of the nucleic acid belonging to the genome of a HIV-1 Group P. The detection of the viral nucleic acid may be either qualitative or quantitative.

The invention also relates to immunogenic compositions which comprise one or more translation products of the nucleotide sequences according to the invention and/or one of the peptides as defined above, obtained, in particular, by synthetic means.

Peptides of this type which may be mentioned are those which are derived from the 06CMU14788 strain, in particular, that which is expressed by the gag gene (SEQ ID No. 2), that which is expressed by the pol gene (SEQ ID No. 3), that which is expressed by the vif gene (SEQ ID No. 4), that which is expressed by the vpr gene (SEQ ID No. 5), that which is expressed by the tat gene (SEQ ID No. 6), that which is expressed by the rev gene (SEQ ID No. 7), that which is expressed by the vpu gene (SEQ ID No. 8), that which is expressed by the env gene (SEQ ID No. 9), or one of its fragments such as a fragment of the V3 loop region, i.e. CIRPGNNTRGQVQLGVMTWYNMKHYVGDIRAAHC (SEQ ID No. 19), or CIRPGNNTRGQVQLGASTWYN-MKHYVGDIRAAHC (SEQ ID No. 20), or CIR-PGNNTRGQVQLGVMTWYNMKHYIGDIRAAHC (SEQ ID No. 21), and fragments of gp41 such as AKQLLH-GIVQQQNNMLRAIEAQQELLRLSVW- GIRQLRARLLAIETYLRDQQL LGLWGCSGQIXCYT-
NVPWNSTWTNKNETELDGIWGNLTWQEWDKLVDNYT
DTIYLEIQKAQEQQKENERKLLELDKW (SEQ ID NO:
22), wherein X can be either I or V; or RLLAIETYL-
RDQQLLGLWGCSGQIXCYTNVPWN (SEQ ID NO: 23);
and that which is expressed by the nef gene (SEQ ID No. 10),
or a fragment of these peptides which are capable of recognizing the antibodies which are produced during an infection
with a HIV-1 Group P. In another embodiment, the present
invention relates to a HIV-1 Group P env amino acid gp 41
region helix-loop-helix region, i.e., AKQLLHGIVQQQN-
NMLRAIEAQQELLRLSVWGIRQLRARL-
LAIETYLRDQQL LGLWGCSGQIXCYTNVPWNSTWT-
NKNETELDGIWGNLTWQEWDKLVDNYT
DTIYLEIQKAQEQQKENERKLLELDKW as described in
SEQ ID NO: 22, wherein X can be either I or V. In one
embodiment, X is I. In another embodiment, X is V. In another
embodiment, the present invention relates to a fragment of the
HIV-1 Group P env amino acid gp 41 region helix-loop-helix
region, i.e., RLLAIETYLRDQQLLGLWGCSGQIXCYT-
NVPWN as described in SEQ ID NO: 23. In another embodiment, the present invention relates to a fragment of the HIV-1
Group P env amino acid gp 41 region helix-loop-helix region,
i.e., IYLEIQKAQEQQKENERKLLELDKW as described in
SEQ ID NO: 24.

In another embodiment, the present invention relates to a
HIV-1 Group P gag amino acid as described in SEQ ID NO:
11. In another embodiment, the present invention relates to a
HIV-1 Group P pol amino acid as described in SEQ ID NO:
12. In another embodiment, the present invention relates to a
HIV-1 Group P vif amino acid as described in SEQ ID NO:
13. In another embodiment, the present invention relates to a
HIV-1 Group P vpr amino acid as described in SEQ ID NO:
14. In another embodiment, the present invention relates to a
HIV-1 Group P tat amino acid as described in SEQ ID NO: 15.
In another embodiment, the present invention relates to a
HIV-1 Group P rev amino acid as described in SEQ ID NO:
16. In another embodiment, the present invention relates to a
HIV-1 Group P vpu amino acid as described in SEQ ID NO:
17. In another embodiment, the present invention relates to a
HIV-1 Group P env amino acid as described in SEQ ID NO:
18. In another embodiment, the present invention relates to a
HIV-1 Group P nef amino acid as described in SEQ ID NO 19.
In another embodiment, the present invention relates to a
HIV-1 Group P env amino acid as described in SEQ ID NO
20. In another embodiment, the present invention relates to a
HIV-1 Group P env amino acid as described in SEQ ID NO
21. In another embodiment, the present invention relates to a
HIV-1 Group P env amino acid as described in SEQ ID NO
22. In another embodiment, the present invention relates to a
HIV-1 Group P env amino acid as described in SEQ ID NO
24. In another embodiment, the present invention relates to a
HIV-1 Group P env amino acid as described in SEQ ID NO
24.

In another embodiment, the present invention relates to a
HIV-1 Group P nef amino acid as described in SEQ ID NO:
25.

The invention also relates to the antibodies which are
directed against one or more of the above-described peptides
and to their use for implementing methods for the in-vitro, in
particular differential, diagnosis of the infection of an individual with a virus of the HIV-1 type using methods which are
known to the skilled person.

The present invention encompasses all the peptides which
are capable of being recognized by antibodies which are
isolated from an infectious serum which is obtained after an
infection with HIV-1 Group P.

The invention furthermore relates to a method for the in-vitro diagnosis of a HIV-1 Group P, which method is characterized in that it comprises bringing a test sample into contact
with antibodies to HIV-1 Group P, and detecting the immunological complexes which are formed between the HIV-1
antigens, which may possibly be present in the biological
sample, and the said antibodies.

The invention also relates to a kit for diagnosing HIV-1,
which kit is characterized in that it includes at least one
reagent according to the invention. Antibodies which are
directed against one or more of the peptides of SEQ ID NOs:
20 to 24, or fragments of these peptides which exhibit said
antibody-recognition capacity. The invention furthermore
relates to antibodies which are directed against the peptide of
SEQ ID NO: 11, or fragments of these peptides which exhibit
said antibody-recognition capacity. The isolated antibody of
the present invention can be a monoclonal antibody, a multispecific antibody, a human antibody, a fully humanized antibody, a partially humanized antibody, an animal antibody, a
recombinant antibody, a chimeric antibody, a single-chain Fv,
a single chain antibody, a single domain antibody, a Fab
fragment, a F(ab')$_2$ fragment, a disulfide-linked Fv, an anti-idiotypic antibody, or a functionally active epitope-binding
fragment thereof.

In another aspect, the present invention relates to an immunoassay for HIV-1 Group P or HIV-1 Group P fragment,
wherein said immunoassay comprises any one of the hereinbefore described antibodies of the present invention In
another aspect, the present invention relates to a pharmaceutical composition comprising a therapeutically effective
amount of any of the hereinbefore described antibodies of the
present invention and a pharmaceutically acceptable carrier
or excipient.

BRIEF DESCRIPTION OF THE FIGURES

FIG. 3 discloses U14788 as SEQ ID NO: 22.
FIG. 4 is an alignment of the amino acid sequences of the
env gp120 V3 loop from 06CMU14788 and 3 clones of this
region of the genome.
FIG. 4 discloses SEQ ID NOS 19-21
and 21, respectively, in order of appearance.
FIG.
5 discloses the "qaq" protein as SEQ ID NO: 11, the "pol"
protein as SEQ ID NO: 12, the "vif" protein as SEQ ID NO:
13, the "vpr" protein as SEQ ID NO: 14, the "tat" protein as
SEQ ID NO: 15, the "rev" protein as SEQ ID NO: 16, the
"vpu" protein as SEQ ID NO: 17, the "env" protein as SEQ ID
NO: 18 and the "nef" protein as SEQ ID NO: 25.
FIG. 6 is a DNA alignment of the native (SEQ ID NO: 41)
and E. coli optimized constructs for the HIV-1 group P rAgs
(SEQ ID NO: 42). A dash indicates identity to the U14788
native construct at that position. Translated protein sequence of the rAgs (SEQ ID NO: 43) is shown beginning at the ATG start codon for methionine (M); a dot indicates translation stop.

FIG. 7A shows a SDS-PAG gel stained with SimplylyBlue Safestain (Invitrogen, Carlsbad, Calif.); the U14788 and HLH-P rAg constructs each express a protein with the expected molecular weight of 16 kilodaltons (kDa). The Mark 12 standard (lane 6) consists of 12 protein with molecular weights of 2.5, 3.5, 6.0, 14.4, 21.5, 31.0, 36.5, 55.4, 66.3, 97.4, 116.3, and 200 kDa (Invitrogen, Carlsbad, Calif.).

FIG. 7B is a Western blot of U14788 and HLH-P rAg using anti-His-tag antibody. Samples were collected at time of induction (T0) and 2, 4, and approximately 16 hours (T1, T2, and T16) post-induction, HLH-P rAg lanes 1-4 and U14788 rAg lanes 7-10. Mark 12 (lane 5) and SeeBlue (lane 6) molecular weight markers are as described in FIG. 7A.

FIG. 10 shows immuno-slot blot evaluation of HLH-P rAg. The HLH-M, HLH-O, HLH-2, and HLH-P rAg were applied onto nitrocellulose sheets at two concentrations, 10 µg/ml and 25 µg/ml. The slot blot strips were incubated with: lane 1: HIV negative human specimen; lane 2: HIV-1 group M specimen ABB218; lane 3: HIV-1 group O specimen ESP1; lane 4: Abbott HIV-2 positive control; lane 5: HIV-1 group N specimen 1131/03; lane 6: HIV-1 group P specimen U14788.

DETAILED DESCRIPTION OF THE INVENTION

I. Introduction

Figure 1:
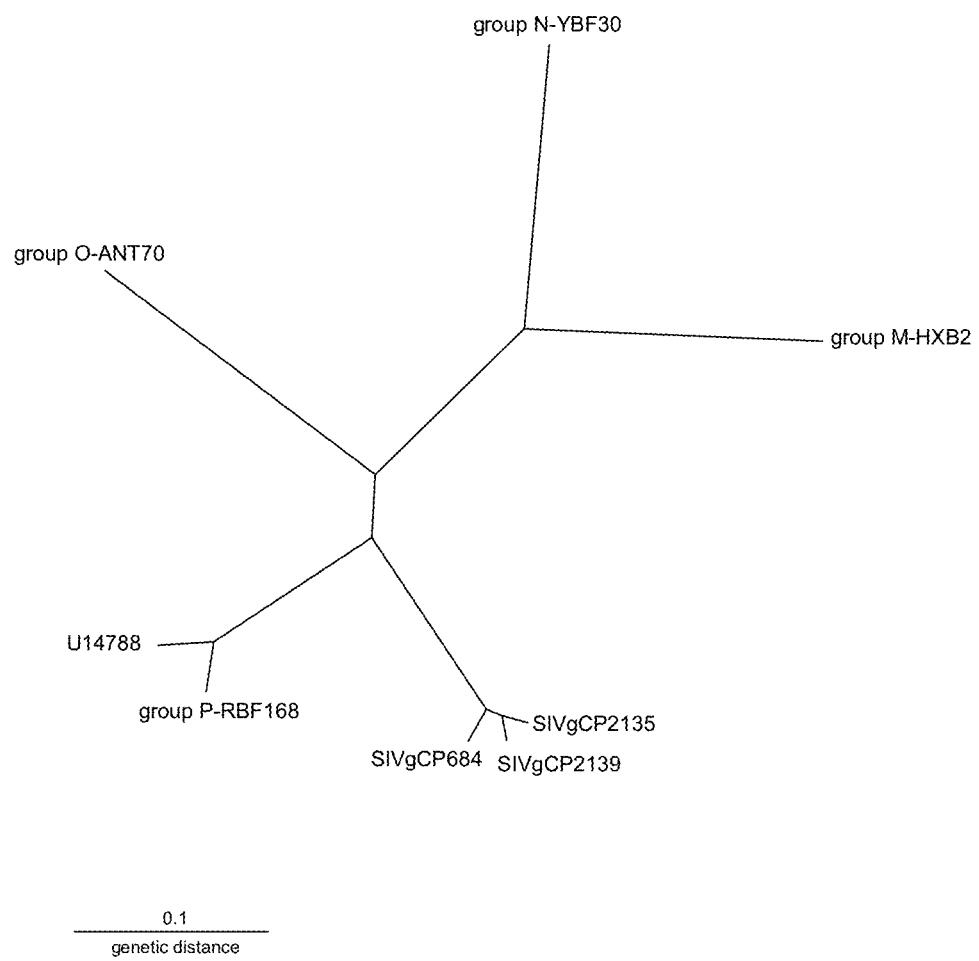
FIG. 1 is a phylogenetic tree showing each HIV-1 group.
Figure 2:
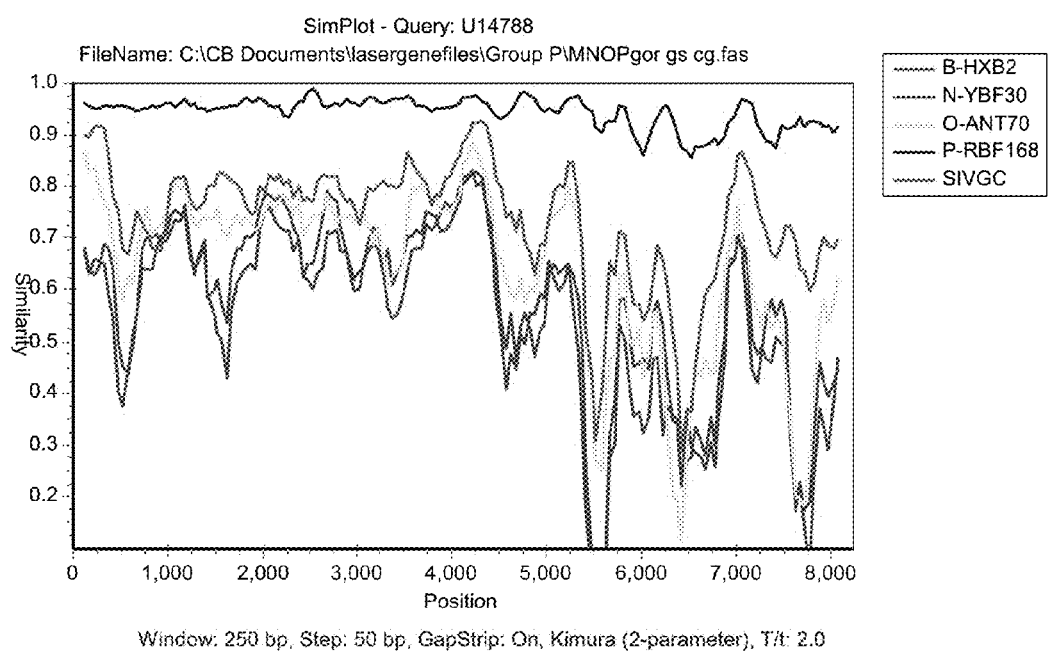
FIG. 2 is a similarity scan of 06CMU14788 in the gap-stripped nucleic acid sequence alignment with HIV-1 group
M isolate HXB2, HIV-1 group N isolate YBF30, HIV-1 group
O isolate ANT70, HIV-1 group P isolate RBF168, and the
consensus of 3 SIVgor strains.

The present invention relates to the complete nucleotide sequence of a HIV-1 Group P designated as strain 06CMU14788 (SEQ ID NO: 1) and fragments thereof, amino acids thereof, primers which are derived from HIV-1 Group P, immunogenic regions thereof, immunoassays and nucleic acid bases assays for the detection of Human Immunodeficiency Virus (HIV) that employ said HIV-1 Group P or fragments thereof and therapeutic compositions containing said HIV-1 Group P or fragments thereof.

DEFINITIONS

As used herein, the terms "antibody" and "antibodies" refer to monoclonal antibodies, multispecific antibodies, human antibodies, humanized antibodies (fully or partially humanized), animal antibodies (in one aspect, a mammal, including a non-primate (for example, a cow, pig, camel, llama, horse, goat, rabbit, sheep, hamsters, guinea pig, cat, dog, rat, mouse, etc) and a non-human primate (for example, a monkey, such as a cynomologous monkey, a chimpanzee, etc), recombinant antibodies, chimeric antibodies, single-chain Fvs (scFv), single chain antibodies, single domain antibodies, Fab fragments, F(ab')$_2$ fragments, disulfide-linked Fv (sdFv), and anti-idiotypic (anti-Id) antibodies (including, for example, anti-Id antibodies to antibodies of the present invention), and functionally active epitope-binding fragments of any of the above. In particular, antibodies include immunoglobulin molecules and immunologically active fragments of immunoglobulin molecules, namely, molecules that contain an antigen binding site.

Immunoglobulin molecules can be of any type (for example, IgG, IgE, IgM, IgD, IgA and IgY), class (for example, IgG$_1$, IgG$_2$, IgG$_3$, IgG$_4$, IgA$_1$ and IgA$_2$) or subclass.

As used herein, the term "epitope" or "epitopes" refers to sites or fragments of a polypeptide or protein having antigenic or immunogenic activity in a subject. An epitope having immunogenic activity is a site or fragment of a polypeptide or protein that elicits an antibody response in an animal. An epitope having antigenic activity is a site or fragment of a polypeptide or protein to which an antibody immunospecifically binds as determined by any method well-known to those skilled in the art, for example by immunoassays.

As used herein, the term "humanized" antibody refers to an immunoglobulin variant or fragment thereof, which is capable of binding to a predetermined antigen and which comprises framework regions having substantially the amino acid sequence of a human immunoglobulin and CDRs having substantially the amino acid sequence of a non-human immunoglobulin. Ordinarily, a humanized antibody has one or more amino acid residues introduced into it from a source that is non-human. In general, the humanized antibody will include substantially all of at least one, and typically two, variable domains (Fab, Fab', F(ab')$_2$, Fabc, Fv) in which all or substantially all of the CDR regions correspond to those of a non-human immunoglobulin and all or substantially all of the FR regions are those of a human immunoglobulin consensus sequence. The humanized antibody optimally comprises at least a portion of an immunoglobulin constant region (Fc), typically that of a human immunoglobulin. Generally, the antibody will contain both the light chain as well as at least the variable domain of a heavy chain. The humanized antibody can be selected from any class of immunoglobulins, including IgM, IgG, IgD, IgA and IgE, and any isotype, including IgG$_1$, IgG$_2$, IgG$_3$ and IgG$_4$. The humanized antibody may comprise sequences from more than one class or isotype, and selecting particular constant domains to optimize desired effector functions is within those skilled in the art.

As used herein, the phrase "immunospecifically binds to an envelope epitope", "immunospecifically binds to a fragment of the V3 loop region" "immunospecifically binds to a fragment of the gp 41 region helix-loop-helix region" and analogous terms thereof refer to peptides, polypeptides, proteins, fusion proteins and antibodies that specifically bind to the envelope protein or a fragment of the envelope protein and do not specifically bind to other peptides. A peptide, polypeptide, protein, or antibody that immunospecifically binds to the envelope protein or a fragment of the envelope protein may bind to other peptides, polypeptides, or proteins with lower binding affinity as determined by, for example, immunoassays, BIAcore, or other assays known in the art. Antibodies or antibody fragments that immunospecifically bind to the envelope protein or a fragment of the envelope protein can be identified, for example, by immunoassays, BIAcore, or other techniques known to those of skill in the art. An antibody binds immunospecifically to the envelope protein or a fragment of the envelope protein when it binds to the envelope protein or a fragment of the envelope protein with a higher binding affinity than to any cross-reactive antigen as determined using experimental techniques, such as, but not limited to, radioimmunoassays (RIA) and enzyme-linked immunosorbent assays (ELISAs) (See, for example, Paul, ed., *Fundamental Immunology*, 2nd ed., Raven Press, New York, pages 332-336 (1989) for a discussion regarding antibody specificity.).

As used herein, the term "isolated" in the context of nucleic acid molecules refers to a nucleic acid molecule which is separated from other nucleic acid molecules which are present in the natural source of the nucleic acid molecule. Moreover, an "isolated" nucleic acid molecule, such as a DNA molecule, can be substantially free of other cellular material, or culture medium when produced by recombinant techniques, or substantially free of chemical precursors or other chemicals when chemically synthesized. In one aspect, nucleic acid molecules are isolated. In another aspect, a nucleic acid molecule encoding an antigen of the invention is isolated.

As used herein, the term "stringent conditions" refers to hybridization to filter-bound DNA in 6× sodium chloride/sodium citrate (SSC) at about 45° C. followed by one or more washes in 0.2×SSC/0.1% SDS at about 50-65° C. The term "under highly stringent conditions", refers to hybridization to filter-bound nucleic acid in 6×SSC at about 45° C. followed by one or more washes in 0.1×SSC/0.2% SDS at about 68° C., or under other stringent hybridization conditions which are known to those skilled in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

As used herein, the terms "subject" and "patient" are used interchangeably. As used herein, the terms "subject" and "subjects" refer to an animal, in one aspect, a bird (for example, a duck or goose), in another aspect, a shark or whale, or in a further aspect, a mammal including, a non-primate (for example, a cow, pig, camel, llama, horse, goat, rabbit, sheep, hamsters, guinea pig, cat, dog, rat, and mouse) and a primate (for example, a monkey, such as a cynomolgous monkey, chimpanzee, and a human).

As used herein, the term "test sample" refers to a biological sample derived from serum, plasma, whole blood, lymph, CNS fluid, urine or other bodily fluids of a subject. The test sample can be prepared using routine techniques known to those skilled in the art.

As used herein, the term "therapeutically effective amount" or "pharmaceutically effective amount" means an amount of antigen, antibody or antibody portion effective, at dosages and for periods of time necessary, to achieve the desired therapeutic result. The exact dose will be ascertainable by one skilled in the art. As known in the art, adjustments based on age, body weight, sex, race, diet, time of administration, drug interaction and severity of condition may be necessary and will be ascertainable with routine experimentation by those skilled in the art. A therapeutically effective amount is also one in which the therapeutically beneficial effects outweigh any toxic or detrimental effects of the antibody or antibody fragment. A "prophylactically effective amount" refers to an amount effective, at dosages and for periods of time necessary to achieve the desired prophylactic result. Typically, since a prophylactic dose is used in subjects prior to or at an earlier stage of disease, the prophylactically effective amount will be less than the therapeutically effective amount.

II. Nucleic Acid Molecules of the Present Invention

The genome sequence for 06CMU14788 is 9238 nucleotides in length while the reported sequence for RBF168 is 8679 nucleotides. Relative to RBF168, 06CMU14788 has 8 additional nucleotides at the 5' end and 536 nucleotides at the 3' end that includes a complete nef gene and partial 3' LTR. The present invention provides an isolated complete nucleic acid of the retrovirus designated 06CMU14788 wherein the nucleic acid comprises SEQ ID NO: 1. More specifically, in one aspect, the present invention relates to an isolated nucleic acid, wherein the nucleic acid comprises SEQ ID NO: 1. In another embodiment, the present invention comprises an isolated nucleic acid which has greater than 90% homology to SEQ ID NO: 1. In another embodiment, the present invention comprises an isolated nucleic acid which has greater than 95% homology to SEQ ID NO: 1. In another embodiment, the present invention comprises an isolated nucleic acid which has greater than 99% homology to SEQ ID NO: 1. In another embodiment, the present invention consists essentially of SEQ ID NO: 1, wherein the sequence has from 1 to about 5 conservative nucleic acid substitutions. In another embodiment, the present invention consists of SEQ ID NO: 1.

In one embodiment, the present invention relates to a HIV-1 Group P gag nucleic acid as described in SEQ ID NO: 2. In another embodiment, the present invention comprises an isolated nucleic acid which has greater than 90% homology to SEQ ID NO: 2. In another embodiment, the present invention comprises an isolated nucleic acid which has greater than 95% homology to SEQ ID NO: 2. In another embodiment, the present invention comprises an isolated nucleic acid which has greater than 99% homology to SEQ ID NO: 2. In another embodiment, the present invention consists essentially of SEQ ID NO: 2, wherein the sequence has from 1 to about 5 conservative nucleic acid substitutions. In another embodiment, the present invention consists of SEQ ID NO: 2.

In another embodiment, the present invention relates to a HIV-1 Group P pol nucleic acid as described in SEQ ID NO: 3. In another embodiment, the present invention comprises an isolated nucleic acid which has greater than 90% homology to SEQ ID NO: 3. In another embodiment, the present invention comprises an isolated nucleic acid which has greater than 95% homology to SEQ ID NO: 3. In another embodiment, the present invention comprises an isolated nucleic acid which has greater than 99% homology to SEQ ID NO: 3. In another embodiment, the present invention consists essentially of SEQ ID NO: 3, wherein the sequence has from 1 to about 5 conservative nucleic acid substitutions. In another embodiment, the present invention consists of SEQ ID NO: 3.

In another embodiment, the present invention relates to a HIV-1 Group P vif nucleic acid as described in SEQ ID NO: 4. In another embodiment, the present invention comprises an isolated nucleic acid which has greater than 90% homology to SEQ ID NO: 4. In another embodiment, the present invention comprises an isolated nucleic acid which has greater than 95% homology to SEQ ID NO: 4. In another embodiment, the present invention comprises an isolated nucleic acid which has greater than 99% homology to SEQ ID NO: 4. In another embodiment, the present invention consists essentially of SEQ ID NO: 2, wherein the sequence has from 1 to about 5 conservative nucleic acid substitutions. In another embodiment, the present invention consists of SEQ ID NO: 4.

In another embodiment, the present invention relates to a HIV-1 Group P vpr nucleic acid as described in SEQ ID NO: 5. In another embodiment, the present invention comprises an isolated nucleic acid which has greater than 90% homology to SEQ ID NO: 5. In another embodiment, the present invention comprises an isolated nucleic acid which has greater than 95% homology to SEQ ID NO: 5. In another embodiment, the present invention comprises an isolated nucleic acid which has greater than 99% homology to SEQ ID NO: 5. In another embodiment, the present invention consists essentially of SEQ ID NO: 5, wherein the sequence has from 1 to about 5 conservative nucleic acid substitutions. In another embodiment, the present invention consists of SEQ ID NO: 5.

In another embodiment, the present invention relates to a HIV-1 Group P tat nucleic acid as described in SEQ ID NO: 6. In another embodiment, the present invention comprises an isolated nucleic acid which has greater than 90% homology to SEQ ID NO: 6. In another embodiment, the present invention comprises an isolated nucleic acid which has greater than 95% homology to SEQ ID NO: 6. In another embodiment, the present invention comprises an isolated nucleic acid which has greater than 99% homology to SEQ ID NO: 6. In another embodiment, the present invention consists essentially of SEQ ID NO: 6, wherein the sequence has from 1 to about 5 conservative nucleic acid substitutions. In another embodiment, the present invention consists of SEQ ID NO: 6.

In another embodiment, the present invention relates to a HIV-1 Group P rev nucleic acid as described in SEQ ID NO: 7. In another embodiment, the present invention comprises an isolated nucleic acid which has greater than 90% homology to SEQ ID NO: 7. In another embodiment, the present invention comprises an isolated nucleic acid which has greater than 95% homology to SEQ ID NO: 7. In another embodiment, the present invention comprises an isolated nucleic acid which has greater than 99% homology to SEQ ID NO: 7. In another embodiment, the present invention consists essentially of SEQ ID NO: 7, wherein the sequence has from 1 to about 5 conservative nucleic acid substitutions. In another embodiment, the present invention consists of SEQ ID NO: 7.

In another embodiment, the present invention relates to a HIV-1 Group P vpu nucleic acid as described in SEQ ID NO: 8. In another embodiment, the present invention comprises an isolated nucleic acid which has greater than 90% homology to SEQ ID NO: 8. In another embodiment, the present invention comprises an isolated nucleic acid which has greater than 95% homology to SEQ ID NO: 8. In another embodiment, the present invention comprises an isolated nucleic acid which has greater than 99% homology to SEQ ID NO: 8. In another embodiment, the present invention consists essentially of SEQ ID NO: 8, wherein the sequence has from 1 to about 5 conservative nucleic acid substitutions. In another embodiment, the present invention consists of SEQ ID NO: 8.

In another embodiment, the present invention relates to a HIV-1 Group P env nucleic acid as described in SEQ ID NO: 9. In another embodiment, the present invention comprises an isolated nucleic acid which has greater than 90% homology to SEQ ID NO: 9. In another embodiment, the present invention comprises an isolated nucleic acid which has greater than 95% homology to SEQ ID NO: 9. In another embodiment, the present invention comprises an isolated nucleic acid which has greater than 99% homology to SEQ ID NO: 9. In another embodiment, the present invention consists essentially of SEQ ID NO: 9, wherein the sequence has from 1 to about 5 conservative nucleic acid substitutions. In another embodiment, the present invention consists of SEQ ID NO: 9. In another aspect, the invention provides an isolated nucleic acid molecule encoding a HIV-1 Group P env. The present invention also provides an isolated nucleic acid molecule that comprises a nucleotide sequence that hybridizes, under stringent conditions, to the nucleic acid molecule described herein that encodes a HIV-1 Group P env.

In another embodiment, the present invention relates to a HIV-1 Group P nef nucleic acid as described in SEQ ID NO: 10. In another embodiment, the present invention comprises an isolated nucleic acid which has greater than 90% homology to SEQ ID NO: 10. In another embodiment, the present invention comprises an isolated nucleic acid which has greater than 95% homology to SEQ ID NO: 10. In another embodiment, the present invention comprises an isolated nucleic acid which has greater than 98% homology to SEQ ID NO: 10. In another embodiment, the present invention comprises an isolated nucleic acid which has greater than 99% homology to SEQ ID NO: 10. In another embodiment, the present invention consists essentially of SEQ ID NO: 10, wherein the sequence has from 1 to about 5 conservative nucleic acid substitutions. In another embodiment, the present invention consists of SEQ ID NO: 10. In another aspect, the invention provides an isolated nucleic acid molecule encoding a HIV-1 Group P nef. The present invention also provides an isolated nucleic acid molecule that comprises a nucleotide sequence that hybridizes, under stringent conditions, to the nucleic acid molecule described herein that encodes a HIV-1 Group P nef.

Conservative nucleic acid substitutions are substitutions of the disclosed nucleic acid sequences that encode for the identical polypeptide.

III. Peptides of the Present Invention

In another embodiment, the present invention relates to isolated proteins encoded by SEQ ID NO: 1. Peptides of this type which may be mentioned are those which are derived from the 06CMU14788 strain, in particular, that which is expressed by the gag gene (SEQ ID No. 2), that which is expressed by the pol gene (SEQ ID No. 3), that which is expressed by the vif gene (SEQ ID No. 4), that which is expressed by the vpr gene (SEQ ID No. 5), that which is expressed by the tat gene (SEQ ID No. 6), that which is expressed by the rev gene (SEQ ID No. 7), that which is expressed by the vpu gene (SEQ ID No. 8), that which is expressed by the env gene (SEQ ID No. 9), or one of its fragments such as a fragment of the gp120 V3 loop region, i.e. CIRPGNNTRGQVQLGVMTWYNMKHYVGDIRAAHC (SEQ ID No. 19), or CIRPGNNTRGQVQLGASTWYNMKHYVGDIRAAHC (SEQ ID No. 20), or CIRPGNNTRGQVQLGVMTWYNMKHYIGDIRAAHC (SEQ ID No. 21), or of the gp41 helix-loop-helix comprising the immundominant region, i.e. AKQLLHGIVQQQNNMLRAIEAQQELLRLSVWGIRQLRARLLAIETYLRDQQLLGLWGCSGQIXCYTNVPWNSTWT-NKNETELDGIWGNLTWQEWDKLVDNYT DTIYLEIQKAQEQQKENERKLLELDKW (SEQ ID NO: 22), wherein X can be either I or V, or RLLAIETYLRDQQLLGLWGCSGQIXCYTNVPWN (SEQ ID NO: 23); and that which is expressed by the nef gene (SEQ ID No. 10), or a fragment of these peptides which are capable of recognizing the antibodies which are produced during an infection with a HIV-1 Group P. In another embodiment, the present invention relates to a HIV-1 Group P env amino acid gp 41 region helix-loop-helix region, i.e., AKQLLHGIVQQQNNMLRAIEAQQELLRLSVWGIRQLRARLLAIETYLRDQQL LGLWGCSGQIXCYTNVPWNSTWTNKNETELDGIWGNLTWQEWDKLVDNYT DTIYLEIQKAQEQQKENERKLLELDKW as described in SEQ ID NO: 22, wherein X can be either I or V. In one embodiment, X is I. In another embodiment, X is V. In another embodiment, the present invention relates to a fragment of the HIV-1 Group P env amino acid gp 41 region helix-loop-helix region, i.e., RLLAIETYLRDQQLLGLWGCSGQIXCYTNVPWN as described in SEQ ID NO: 23. In another embodiment, the present invention relates to a fragment of the HIV-1 Group P env amino acid gp 41 region helix-loop-helix region, i.e., IYLEIQKAQEQQKENERKLLELDKW as described in SEQ ID NO: 24.

In another embodiment, the present invention relates to a HIV-1 Group P gag amino acid sequence as described in SEQ ID NO: 11. In another embodiment, the present invention relates to a HIV-1 Group P pol amino acid sequence as described in SEQ ID NO: 12. In another embodiment, the present invention relates to a HIV-1 Group P vif amino acid sequence as described in SEQ ID NO: 13. In another embodiment, the present invention relates to a HIV-1 Group P vpr amino acid sequence as described in SEQ ID NO: 14. In another embodiment, the present invention relates to a HIV-1 Group P tat amino acid sequence as described in SEQ ID NO: 15. In another embodiment, the present invention relates to a HIV-1 Group P rev amino acid sequence as described in SEQ ID NO: 16. In another embodiment, the present invention relates to a HIV-1 Group P vpu amino acid sequence as described in SEQ ID NO: 17. In another embodiment, the present invention relates to a HIV-1 Group P env amino acid sequence as described in SEQ ID NO: 18. In another embodiment, the present invention relates to a HIV-1 Group P env amino acid sequence as described in SEQ ID NO 19. In another embodiment, the present invention relates to a HIV-1 Group P env amino acid sequence as described in SEQ ID NO 20. In another embodiment, the present invention relates to a HIV-1 Group P env amino acid sequence as described in SEQ ID NO 21. In another embodiment, the present invention relates to a HIV-1 Group P env amino acid sequence as described in SEQ ID NO 22. In another embodiment, the present invention relates to a HIV-1 Group P env amino acid sequence as described in SEQ ID NO 24. In another embodiment, the present invention relates to a HIV-1 Group P env amino acid sequence as described in SEQ ID NO 23.

In another embodiment, the present invention relates to a HIV-1 Group P nef amino acid as described in SEQ ID NO: 25.

The invention also relates to the antibodies which are directed against one or more of the above-described peptides and to their use for implementing methods for the in-vitro, in particular differential, diagnosis of the infection of an individual with a virus of the HIV-1 type using methods which are known to the skilled person.

The present invention encompasses all the peptides which are capable of being recognized by antibodies which are isolated from a sample or specimen which is obtained after an infection with HIV-1 Group P.

The invention also relates to immunogenic compositions which comprise one or more translation products of the nucleotide sequences according to the invention and/or one of the peptides as defined above, obtained, in particular, by synthetic means.

In another embodiment, the present invention relates to immunogenic peptides such as a fragment of the V3 loop region, i.e. CIRPGNNTRGQVQLGVMTWYNMKHYVGDIRAAHC (SEQ ID No. 19), or CIRPGNNTRGQVQLGASTWYNMKHYVGDIRAAHC (SEQ ID No. 20), or CIRPGNNTRGQVQLGVMTWYNMKHYIGDIRAAHC (SEQ ID No. 21). In another embodiment, the immunogenic peptide fragment of SEQ ID NOs: 19-21 is 5 to 33 amino acids long. In another embodiment, the immunogenic peptide fragment is 8 to 30 amino acids long. In another embodiment, the immunogenic peptide fragment is 10 to 25 amino acids long.

In another embodiment, the present invention relates to immunogenic peptides such as a fragment of the gp 41 region helix-loop-helix region, i.e., AKQLLHGIVQQQNNMLRAIEAQQELLRLSVWGIRQLRARLLAIETYLRDQQL LGLWGCSGQIXCYTNVPWNSTWTNKNETELDGIWGNLTWQEWDKLVDNYT DTIYLEIQKAQEQQKENERKLLELDKW as described in SEQ ID NO: 22, wherein X can be either I or V. In one embodiment, X is I. In another embodiment, X is V. In another embodiment, the immunogenic peptide fragment is RLLAIETYLRDQQLLGLWGCSGQIXCYTNVPWN as described in SEQ ID NO: 23. In another embodiment, the immunogenic peptide fragment of SEQ ID NO: 23 is 5 to 31 amino acids long. In another embodiment, the immunogenic peptide fragment is 8 to 28 amino acids long. In another embodiment, the immunogenic peptide fragment is 10 to 25 amino acids long.

In another embodiment, the immunogenic peptide fragment is IYLEIQKAQEQQKENERKLLELDKW as described in SEQ ID NO: 24. In another embodiment, the immunogenic peptide fragment of SEQ ID NO: 23 is 5 to 24 amino acids long. In another embodiment, the immunogenic peptide fragment is 8 to 21 amino acids long. In another embodiment, the immunogenic peptide fragment is 10 to 19 amino acids long.

In another embodiment, peptides of SEQ ID NOs: 11 to 25 can be detectably labeled with a fluorescent label, a colorimetric label, a radio active label, or the like.

IV. Antibodies of the Present Invention

The present invention provides for an antibody that immunospecifically binds to HIV-1 Group P or a fragment thereof. The invention also relates to the antibodies which are directed against one or more of the above-described peptides and to their use for implementing methods for the in-vitro, in particular differential, diagnosis of the infection of an individual with a virus of the HIV-1 type using methods which are known to the skilled person.

In one aspect, the derivatives have conservative amino acid substitutions are made at one or more predicted non-essential amino acid residues (i.e., amino acid residues which are not critical for the antibody to immunospecifically bind to HIV-1 Group P or a fragment thereof). A “conservative amino acid substitution” is one in which the amino acid residue is replaced with the amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that exhibit enhanced binding affinity to HIV-1 Group P or a fragment thereof. Following mutagenesis, the encoded antibody can be expressed and the activity of the antibody can be determined.

V. Methods for Preparing the Peptides of the Present Invention

The peptides of the present invention can be prepared using routine techniques known to those skilled in the art. Proteins can be expressed in mammalian cells, yeast, bacteria, or other cells under the control of appropriate promoters. Cell-free translation systems also can be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, (Cold Spring Harbor, N.Y., 1989).

To express the HIV-1 Group P genes of the invention (e.g., SEQ ID NOs: 2 to 10), nucleic acid molecules encoding the peptides, as described above, are inserted into expression vectors such that the genes are operatively linked to transcriptional and translational control sequences. The nucleic acid molecule may be actual group P viral sequence or bacterial codon biased sequence that results in the same translated protein product as the native viral sequence. In this context, the term "operatively linked" is intended to mean that a HIV-1 Group P gene is ligated into a vector such that transcriptional and translational control sequences within the vector serve their intended function of regulating the transcription and translation of the antibody gene. The expression vector and expression control sequences are chosen to be compatible with the expression host cell used. The HIV-1 Group P genes are inserted into the expression vector by standard methods (for example, ligation of complementary restriction sites on the HIV-1 Group P gene fragment and vector, or blunt end ligation if no restriction sites are present). Additionally or alternatively, the recombinant expression vector can encode a signal peptide that facilitates secretion of the HIV-1 Group P from a host cell. The HIV-1 Group P gene can be cloned into the vector such that the signal peptide is linked in-frame to the amino terminus of the HIV-1 Group P gene. Additionally or alternatively, HIV-1 Group P gene can be cloned into a vector as a fusion to an unrelated protein or peptide to enhance expression and/or facilitate purification of the fusion protein.

In addition to the HIV-1 Group P genes, the recombinant expression vectors can carry regulatory sequences that control the expression of the HIV-1 Group P genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology. Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of the expression of protein desired, etc. Preferred regulatory sequences for mammalian host cell expression include viral elements that direct high levels of protein expression in mammalian cells, such as promoters and/or enhancers derived from cytomegalovirus ("CMV") (such as the CMV promoter/enhancer), Simian Virus 40 ("SV40") (such as the SV40 promoter/enhancer), adenovirus, (such as the adenovirus major late promoter ("AdMLP")) and polyoma. For further description of viral regulatory elements, and sequences thereof, see for example, U.S. Pat. No. 5,168,062 by Stinski, U.S. Pat. No. 4,510,245 by Bell et al. and U.S. Pat. No. 4,968,615 by Schaffner et al.

In addition to the HIV-1 Group P genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (See, for example, U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase ("DHFR") gene for use in dhfr-host cells with methotrexate selection/amplification and the neomycin ("neo") gene for G418 selection.

VI. Immunoassays

In another aspect, the present invention relates to immunoassays that can be used for the qualitative and/or quantitative detection of antibodies to HIV-1 group P, HIV-1 Group P protein or protein fragment in a test sample. The immunoassays of the present invention can be conducted using any format known in the art, such as, but not limited to, a sandwich format, a competitive inhibition format (including both forward or reverse competitive inhibition assays) or in a fluorescence polarization format. In yet other assay formats, the polypeptides disclosed herein may be utilized to detect the presence of antibodies specific for HIV-1 Group P-derived polypeptides in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of HIV-1 Group P-derived polypeptide antibody. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from the same source or, alternatively, a second source different from the first source. Combinations of a recombinant antigen on a solid phase and synthetic peptide in the indicator phase also are possible. Any assay format which utilizes an antigen specific for HIV-1 Group P-derived polypeptide from a first source as the capture antigen and an antigen specific for HIV-1 Group P-derived polypeptide from a second source are contemplated.

In immunoassays for the qualitative detection of HIV-1 Group P or HIV-1 Group P fragment in a test sample, at least one antibody that binds to certain epitopes of HIV-1 Group P or HIV-1 Group P fragment thereof is contacted with at least one test sample suspected of containing or that is known to contain HIV-1 Group P or HIV-1 Group P fragment to form an antibody HIV-1 Group P immune complex. The antibodies described in Section IV herein can be used in such immunoassays to form such antibody HIV-1 Group P immune complexes in at least one test sample. These immune complexes can then detected using routine techniques known to those skilled in the art. For example, the antibody of the present invention can be labeled with a detectable label to detect the presence of an antibody HIV-1 Group P complex. Alternatively, the HIV-1 Group P or HIV-1 Group P fragments in the test sample can be labeled with a detectable label and the resulting antibody HIV-1 Group P immune complexes detected using routine techniques known to those skilled in the art. Detectable labels and their attachment to antibodies are discussed in more detail infra.

Alternatively, a second antibody that binds to the HIV-1 Group P or HIV-1 Group P fragment and that contains a detectable label can be added to the test sample and used to detect the presence of the antibody HIV-1 Group P complex. Any detectable label known in the art can be used. Detectable labels and their attachment to antibodies are discussed in more detail infra.

In one embodiment, the immunoassay is a kit comprising one or more polypeptides selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25 or fragments of any of SEQ ID NOs: 11-24; and one or more antibodies which are directed against a peptide selected from the group consisting of the gag gene (SEQ ID No. 2), the pol gene (SEQ ID No. 3), vif gene (SEQ ID No. 4), vpr gene (SEQ ID No. 5), the tat gene (SEQ ID No. 6), the rev gene (SEQ ID No. 7), the vpu gene (SEQ ID No. 8), the env gene (SEQ ID No. 9); and the nef gene (SEQ ID No. 10), or fragments of any of SEQ ID Nos 2 to 10. The HIV-1 Group P peptide, fragment or analogue can be bound to a solid support, such as the solid supports discussed above in connection with the sandwich assay format. Preferably, the HIV-1 Group P peptide fragment has an amino acid sequence that contains amino acids from the env region of HIV-1 Group P.

In one embodiment, the amino acids from the env region are a fragment of the V3 loop region, i.e. CIRPGNNTRGQVQLGVMTWYNMKHYVGDIRAAHC (SEQ ID No. 19), or CIRPGNNTRGQVQLGASTWYNMKHYVGDIRAAHC (SEQ ID No. 20), or CIRPGNNTRGQVQLGVMTWYNMKHYIGDIRAAHC (SEQ ID No. 21). In another embodiment, the amino acids from the env region are 5 to 33 amino acids from SEQ ID NOs: 19-21. In another embodiment, the amino acids from the env region from SEQ ID NOs: 19-21 is 8 to 30 amino acids long. In another embodiment, the amino acids from the env region from SEQ ID NOs: 19-21 are 10 to 25 amino acids long.

In another embodiment, the HIV-1 Group P peptide fragment bound to a solid support is from the gp 41 region helix-loop-helix region, i.e., AKQLLHGIVQQQNNMLRAIEAQQELLRLSVWGIRQLRARLLAIETYLRDQQLLGLWGCSGQIXCYTNVPWNSTWTNKNETELDGIWGNLTWQEWDKLVDNYTDTIYLEIQKAQEQQKENERKLLELDKW as described in SEQ ID NO: 22, wherein X can be either I or V. In one embodiment, X is I. In another embodiment, X is V. In another embodiment, the immunogenic peptide fragment is RLLAIETYLRDQQLLGLWGCSGQIXCYTNVPWN as described in SEQ ID NO: 23. In another embodiment, the immunogenic peptide fragment of SEQ ID NO: 23 is 5 to 31 amino acids long. In another embodiment, the immunogenic peptide fragment is 8 to 28 amino acids long. In another embodiment, the immunogenic peptide fragment is 10 to 25 amino acids long.

In another embodiment, the immunogenic peptide fragment is IYLEIQKAQEQQKENERKLLELDKW as described in SEQ ID NO: 24. In another embodiment, the immunogenic peptide fragment of SEQ ID NO: 24 is 5 to 24 amino acids long. In another embodiment, the immunogenic peptide fragment is 8 to 21 amino acids long. In another embodiment, the immunogenic peptide fragment is 10 to 19 amino acids long.

In immunoassays for the quantitative detection of HIV-1 Group P, such as a sandwich type format, at least two antibodies are employed to separate and quantify HIV-1 Group P or HIV-1 Group P fragment in a test sample. More specifically, the immunoassay with at least two antibodies bind to certain epitopes of HIV-1 Group P or HIV-1 Group P fragment forming an immune complex which is referred to as a "sandwich". Generally, one or more antibodies can be used to capture the HIV-1 Group P or HIV-1 Group P fragment in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, it is preferred that both antibodies binding to their epitope are not diminished by the binding of any other antibody in the assay to its respective epitope. In other words, antibodies should be selected so that the one or more first antibodies brought into contact with a test sample suspected of containing HIV-1 Group P or HIV-1 Group P fragment do not bind to all or part of an epitope recognized by the second or subsequent antibodies, thereby interfering with the ability of the one or more second detection antibodies to bind to the HIV-1 Group P or HIV-1 Group P fragment.

In a preferred embodiment, the test sample suspected of containing HIV-1 Group P or a fragment thereof can be contacted with at least one first capture antibody (or antibodies) and at least one second detection antibodies either simultaneously or sequentially. In the sandwich assay format, a test sample suspected of containing HIV-1 Group P or a fragment thereof is first brought into contact with at least one first capture antibody that specifically binds to a particular epitope under conditions which allow the formation of a first antibody HIV-1 Group P complex. If more than one capture antibody is used, a first multiple capture antibody HIV-1 Group P complex is formed. In a sandwich assay, the antibodies, preferably, at least one capture antibody, are used in molar excess amounts of the maximum amount of HIV-1 Group P or a fragment thereof expected in the test sample. For example, from about 5 μg/mL to about 1 mg/mL of antibody per mL of microparticle coating buffer can be used.

Optionally, prior to contacting the test sample with at least one first capture antibody, the at least one first capture antibody can be bound to a solid support which facilitates the separation of the first antibody HIV-1 Group P complex from the test sample. Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind HIV-1 Group P or a fragment thereof. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing HIV-1 Group P or a fragment thereof is brought into contact with the at least one first capture antibody, the test sample is incubated in order to allow for the formation of a first capture antibody (or multiple antibody)-HIV-1 Group P complex. The incubation can be carried out at a pH of from about 4.5 to about 10.0, at a temperature of from about 2° C. to about 45° C., and for a period from at least about one (1) minute to about eighteen (18) hours, preferably from about 2-6 minutes, most preferably from about 3-4 minutes.

After formation of the first/multiple capture antibody HIV-1 Group P complex, the complex is then contacted with at least one second detection antibody (under conditions which allow for the formation of a first/multiple antibody-HIV-1 Group P-second antibody complex). If the first antibody-HIV-1 Group P complex is contacted with more than one detection antibody, then a first/multiple capture antibody HIV-1 Group P-multiple antibody detection complex is formed. As with first antibody, when at least second (and subsequent) antibody is brought into contact with the first antibody HIV-1 Group P complex, a period of incubation under conditions similar to those described above is required for the formation of the first/multiple antibody HIV-1 Group P-second/multiple antibody complex. Preferably, at least one second antibody contains a detectable label. The detectable label can be bound to at least one second antibody prior to, simultaneously with or after the formation of the first/multiple antibody HIV-1 Group P-second/multiple antibody complex. Any detectable label known in the art can be used. For example, the detectable label can be a radioactive label, such as, $^3H$, $^{125}I$, $^{35}S$, $^{14}C$, $^{32}P$, $^{33}P$ an enzymatic label, such as horseradish peroxidase, alkaline phosphatase, glucose 6-phosphate dehydrogenase, etc., a chemiluminescent label, such as, acridinium esters, luminal, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The detectable label can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The first antibody/multiple-HIV-1 Group P-second/multiple antibody complex can be, but does not have to be, separated from the remainder of the test sample prior to quantification of the label. For example, if at least first capture antibody is bound to a solid support, such as a well or a bead, separation can be accomplished by removing the fluid (from the test sample) from contact with the solid support. Alternatively, if at least first capture antibody is bound to a solid support it can be simultaneously contacted with the HIV-1 Group P-containing sample and the at least one second detection antibody to form a first (multiple) antibody HIV-1 Group P-second (multiple) antibody complex, followed by removal of the fluid (test sample) from contact with the solid support. If at least first capture antibody is not bound to a solid support, then the first antibody/multiple-HIV-1 Group P-second/multiple antibody complex does not have to be removed from the test sample for quantification of the amount of the label.

After formation of the labeled first antibody HIV-1 Group P-second antibody complex, the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of HIV-1 Group P or a fragment thereof in the test sample is determined by use of a standard curve that has been generated using serial dilutions of HIV-1 Group P or a fragment thereof of known concentration. Other than using serial dilutions of HIV-1 Group P or a fragment thereof, the standard curve can be generated gravimetrically, by mass spectroscopy, by calibrators, and by other techniques known in the art.

In a forward competitive format, an aliquot of labeled HIV-1 Group P or a fragment thereof or HIV-1 Group P analogue thereof of a known concentration is used to compete with HIV-1 Group P or a fragment thereof in a test sample for binding to an HIV-1 Group P antibody.

In a forward competition assay, an immobilized antibody (such as an antibody of the present invention) can either be sequentially or simultaneously contacted with the test sample and a HIV-1 Group P or a fragment thereof or HIV-1 Group P analogue thereof. The HIV-1 Group P or a fragment thereof or HIV-1 Group P analogue thereof can be labeled with any detectable label known to those skilled in the art, including those detectable labels discussed above in connection with the sandwich assay format. In this assay, the antibody of the present invention can be immobilized on to a solid support using the techniques discussed previously herein. Alternatively, the antibody of the present invention can be coupled to an antibody, such as an antispecies antibody, that has been immobilized on to a solid support, such as a microparticle.

The labeled HIV-1 Group P or a fragment thereof or HIV-1 Group P analogue thereof, the test sample and the antibody are incubated under conditions similar to those described above in connection with the sandwich assay format. Two different species of antibody-HIV-1 Group P complexes are then generated. Specifically, one of the antibody HIV-1 Group P complexes generated contains a detectable label while the other antibody HIV-1 Group P complex does not contain a detectable label. The antibody HIV-1 Group P complex can be, but does not have to be, separated from the remainder of the test sample prior to quantification of the detectable label. Regardless of whether the antibody HIV-1 Group P complex is separated from the remainder of the test sample, the amount of detectable label in the antibody HIV-1 Group P complex is then quantified. The concentration of HIV-1 Group P or fragment thereof in the test sample can then be determined by comparing the quantity of detectable label in the antibody HIV-1 Group P complex to a standard curve. The standard curve can be generated using serial dilutions of HIV-1 Group P or fragment thereof of known concentration, by mass spectroscopy, gravimetrically and by other techniques known in the art.

The antibody HIV-1 Group P complex can be separated from the test sample by binding the antibody to a solid support, such as the solid supports discussed above in connection with the sandwich assay format, and then removing the remainder of the test sample from contact with the solid support.

In a reverse competition assay, an immobilized HIV-1 Group P peptide or a fragment or analogue thereof can either be sequentially or simultaneously contacted with a test sample and at least one labeled antibody. Preferably, the HIV-1 Group P peptide fragment has an amino acid sequence that contains amino acids from the gag region of HIV-1 Group P.

The immobilized HIV-1 Group P peptide, fragment or analogue thereof, test sample and at least one labeled antibody are incubated under conditions similar to those described above in connection with the sandwich assay format. Two different species HIV-1 Group P-antibody complexes are then generated. Specifically, one of the HIV-1 Group P-antibody complexes generated is immobilized and contains a detectable label while the other HIV-1 Group P-antibody complex is not immobilized and contains a detectable label. The non-immobilized HIV-1 Group P-antibody complex and the remainder of the test sample are removed from the presence of the immobilized HIV-1 Group P-antibody complex through techniques known in the art, such as washing. Once the non-immobilized HIV-1 Group P antibody complex is removed, the amount of detectable label in the immobilized HIV-1 Group P-antibody complex is then quantified. The concentration of HIV-1 Group P or fragment thereof in the test sample can then be determined by comparing the quantity of detectable label in the HIV-1 Group P-complex to a standard curve. The standard curve can be generated using serial dilutions of HIV-1 Group P or fragment thereof of known concentration, by mass spectroscopy, gravimetrically and by other techniques known in the art.

In a fluorescence polarization assay, in one embodiment, an antibody or functionally active fragment thereof is first contacted with an unlabeled test sample suspected of containing HIV-1 Group P or fragment thereof to form an unlabeled HIV-1 Group P-antibody complex. The unlabeled HIV-1 Group P-antibody complex is then contacted with a fluorescently labeled HIV-1 Group P, fragment or analogue thereof. The labeled HIV-1 Group P peptide, fragment or analogue thereof competes with any unlabeled HIV-1 Group P or fragment thereof in the test sample for binding to the antibody or functionally active fragment thereof. The amount of labeled HIV-1 Group P-antibody complex formed is determined and the amount of HIV-1 Group P in the test sample determined via use of a standard curve.

Alternatively, in another embodiment, an antibody or functionally active fragment thereof is simultaneously contacted with a fluorescently labeled HIV-1 Group P, fragment or analogue thereof and an unlabeled test sample suspected of containing HIV-1 Group P or fragment thereof to form both labeled HIV-1 Group P-antibody complexes and unlabeled HIV-1 Group P-antibody complexes. The amount of labeled HIV-1 Group P-antibody complex formed is determined and the amount of HIV-1 Group P in the test sample determined via use of a standard curve. Alternatively, in yet another embodiment, an antibody or functionally active fragment thereof is first contacted with a fluorescently labeled HIV-1 Group P, fragment or analogue thereof to form a labeled HIV-1 Group P-antibody complex. The labeled HIV-1 Group P-antibody complex is then contacted with an unlabeled test sample suspected of containing HIV-1 Group P or fragment thereof. Any unlabeled HIV-1 Group P or fragment thereof in the test sample competes with the labeled HIV-1 Group P, fragment or analogue thereof for binding to the antibody or functionally active fragment thereof. The amount of labeled HIV-1 Group P-antibody complex formed is determined the amount of HIV-1 Group P in the test sample determined via use of a standard curve In another embodiment, DNA sequences produced by the polymerase chain reaction (PCR) using primers obtained from SEQ ID Nos. 1-24 are also provided by the invention. Such oligodeoxyribonucleotide or oligoribonucleotide typically have a length of at least 8 nucleotides, preferably of at least 12 nucleotides, and even more preferentially at least 20 nucleotides. In one embodiment, primers are obtained from the HIV-1 Group P genes of the invention (e.g., SEQ ID NOs: 2 to 10). Examples of conditions suitable for nucleotide amplification are well-known to those of skill in the art and include enzymes, buffers, nucleotides, incubation times and temperatures and the like. Other amplification techniques of the target nucleic acid can be advantageously employed as alternatives to PCR. Detection can be qualitative or quantitative. Qualitative or quantitative detection can also be used in selecting therapies for HIV-1 Group P infected patients.

The nucleotide sequences of the invention, can likewise be employed in other procedures of amplification of a target nucleic acid, such as: the TAS technique (Transcription-based Amplification System), described by Kwoh et al. in 1989; the 3SR technique (Self-Sustained Sequence Replication), described by Guatelli et al. in 1990; the NASBA technique (Nucleic Acid Sequence Based Amplification), described by Kievitis et al. in 1991; the SDA technique (Strand Displacement Amplification) (Walker et al., 1992); the TMA technique (Transcription Mediated Amplification).

The polynucleotides of the invention can also be employed in techniques of amplification or of modification of the nucleic acid serving as a probe, such as: the LCR technique (Ligase Chain Reaction), described by Landegren et al. in 1988 and improved by Barany et al. in 1991, which employs a thermostable ligase; the RCR technique (Repair Chain Reaction), described by Segev in 1992; the CPR technique (Cycling Probe Reaction), described by Duck et al. in 1990; the amplification technique with Q-beta replicase, described by Miele et al. in 1983 and especially improved by Chu et al. in 1986, Lizardi et al. in 1988, then by Burg et al. as well as by Stone et al. in 1996.

In the case where the target polynucleotide to be detected is possibly an RNA, for example a genomic viral RNA or an mRNA, it will be possible to use, prior to the employment of an amplification reaction with the aid of at least one primer according to the invention or to the employment of a detection procedure with the aid of at least one probe of the invention, an enzyme of reverse transcriptase type in order to obtain a cDNA from the RNA contained in the biological sample. The cDNA obtained will thus serve as a target for the primer(s) or the probe(s) employed in the amplification or detection procedure according to the invention.

The detection probe will be chosen in such a manner that it hybridizes with the target sequence or the amplicon generated from the target sequence. By way of example, such a probe will advantageously have a sequence of at least 12 nucleotides, in particular of at least 20 nucleotides, and preferably of at least 100 nucleotides. The invention also comprises the nucleotide sequences utilizable as a probe or primer according to the invention, characterized in that they are labeled with a radioactive compound or with a nonradioactive compound. The unlabeled nucleotide sequences can be used directly as probes or primers, although the sequences are generally labeled with a radioactive element or with a nonradioactive molecule (biotin, acetylaminofluorene, digoxigenin, 5-bromodeoxyuridine, fluorescein) to obtain probes which are utilizable for numerous applications.

The hybridization technique can be carried out in various manners (Matthews et al., 1988). The most general method consists in immobilizing the nucleic acid extract of cells on a support (such as nitrocellulose, nylon, polystyrene) and in incubating, under well-defined conditions, the immobilized target nucleic acid with the probe. After hybridization, the excess of probe is eliminated and the hybrid molecules formed are detected by the appropriate method (measurement of the radioactivity, of the fluorescence or of the enzymatic activity linked to the probe). The invention likewise comprises the nucleotide sequences according to the invention, characterized in that they are immobilized on a support, covalently or noncovalently.

According to another advantageous mode of employing nucleotide sequences according to the invention, the latter can be used immobilized on a support and can thus serve to capture, by specific hybridization, the target nucleic acid obtained from the biological sample to be tested. If necessary, the solid support is separated from the sample and the hybridization complex formed between said capture probe and the target nucleic acid is then detected with the aid of a second probe, a so-called detection probe, labeled with an easily detectable element.

In another embodiment, the hybridization can be carried out using quantitative real time polymerase chain reaction (real time PCR) for the simultaneous amplification and detection of target nucleic acid either with or without a solid support. Detection can be accomplished using fluorophores. In one embodiment, the fluorophore is a double stranded DNA-binding dye. In another embodiment the probe is a fluorescence resonance transfer probe (FRET), containing a fluorophore with emission wavelengths from about 400 nm to about 900 nm and a quencher with an absorbance wavelengths from about 400 nm to about 900 nm. Fluorophores and quenchers are available from commercial resource (eg. Molecular Probes, Eugene, Oreg.; Epoch Bioscience, Bothell, Wash.). Typically the probes are from about 8 to 30 bases long.

VII. Pharmaceutical Compositions and Pharmaceutical Administration

The polypeptides of the present invention can be incorporated into pharmaceutical compositions suitable for administration to a subject. For instance, the polypeptides of the present invention can be used as a vaccine for the prevention of HIV infection. Typically, the pharmaceutical composition comprises a therapeutically or pharmaceutically effective amount of an antibody or the present invention along with a pharmaceutically acceptable carrier or excipient. As used herein, "pharmaceutically acceptable carrier" or "pharmaceutically acceptable excipient" includes any and all solvents, dispersion media, coating, antibacterial and antifungal agents, isotonic and absorption delaying agents, and the like that are physiologically compatible. Examples of pharmaceutically acceptable carriers or excipients include one or more of water, saline, phosphate buffered saline, dextrose, glycerol, ethanol and the like as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody portion also may be included. Optionally, disintegrating agents can be included, such as cross-linked polyvinyl pyrrolidone, agar, alginic acid or a salt thereof, such as sodium alginate and the like. In addition to the excipients, the pharmaceutical composition can include one or more of the following, carrier proteins such as serum albumin, buffers, binding agents, sweeteners and other flavoring agents; coloring agents and polyethylene glycol.

The compositions of this invention may be in a variety of forms. They include, for example, liquid, semi-solid and solid dosage forms, such as liquid solutions (e.g. injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody or antibody fragment is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e. antibody or antibody fragment) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The polypeptides of the present invention can be administered by a variety of methods known in the art, although for many therapeutic applications, the preferred route/mode of administration is intravenous injection or infusion. As will be appreciated by those skilled in the art, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. (See, e.g. *Sustained and Controlled Release Drug Delivery Systems*, J. R. Robinson, ed., Marcel Dekker, Inc., New York, 1978).

In certain embodiments, a polypeptide of the present invention may be orally administered, for example, with an inert diluent or an assimilable edible carrier. The compound (and other ingredients if desired) may also be enclosed in a hard or soft shell gelatin capsule, compressed into tablets, buccal tablets, troches, capsules, elixiers, suspensions, syrups, wafers, and the like. To administer a polypeptide of the invention by other than parenteral administration, it may be necessary to coat the compound with, or co-administer the compound with, a material to prevent its inactivation.

Supplementary active compounds also can be incorporated into the compositions. In certain embodiments, the polypeptide is co-formulated with and/or co-administered with one or more additional therapeutic agents. Such combination therapies may advantageously utilize lower dosages of the administered therapeutic agents, thus avoiding possible toxicities or complications associated with monotherapies or alternatively, act synergistically or additively to enhance the therapeutic effect.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be tested; each unit containing a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of an polypeptide of the invention is 0.1-20 mg/kg, more preferably 0.5-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another embodiment, proteins derived from group P and the group P virus can be used for design and evaluation of antiviral drugs. The protein structure could be used for drug design; viral proteins could be used in enzymatic and/or binding assays to evaluate drug activity; virus in cell culture could be used to drug effect by measuring viral replication, infectivity, and cell receptor blockage.

Now by way of example, and not of limitation, examples of the present invention shall now be given.

EXAMPLE 1

Identification of HIV-1 Group P

To identify new strains of HIV, human specimens (plasma or serum) were screened using commercially available HIV immunoassays and any specimens that were reactive or had a signal within 80% of the cutoff value in at least one HIV immunoassay were then tested in peptide enzyme-linked immunoassays (PEIA) [ref: Yamaguchi J, et al. AIDS Res Hum Retroviruses 2004; 20:944-857) that contain peptides derived from the env gp41 immunodominant region (IDR) or gp120 V3 loop of a variety of HIV and SIV strains. To screen for HIV strains related to the newly discovered SIV gor and HIV-1 group P, an SIVgor peptide was incorporated into the IDR PEIA. Using this PEIA, we screened 90 HIV seropositive specimens that had been previously screened with IDR and V3 PEIAs that did not contain an SIVgor peptide and had been classified as potential HIV variants i.e. not classified as HIV-1 group M or group O based on antibody reactivity to peptides. Only 5 of the 90 specimens showed reactivity to the SIVgor peptide that was considered significant relative to the reactivity to the other peptides. [See Table X].

TABLE X

| | IDR PEIA Results: | | | | | | | |
|---|---|---|---|---|---|---|---|---|
| | | | | Specimen | | | | |
| IDR Peptide derived from | Negative Control | HIV-1 Group M control | HIV-1 Group O control | U14788 | U17609 | U17631 | U17849 | U17965 |
| none | 0.143 | 0.094 | 0.143 | 0.079 | 0.066 | 0.073 | 0.072 | 0.059 |
| Group M (HXB2) | 0.07 | 3.208 | 0.087 | 0.897 | 3.374 | 3.027 | 3.399 | 3.407 |
| Group O (ANT70) | 0.076 | 0.395 | 2.872 | 0.254 | 2.855 | 1.081 | 2.186 | 2.319 |

TABLE X-continued

IDR PEIA Results:

| IDR Peptide derived from | Specimen | | | | | | | |
|---|---|---|---|---|---|---|---|---|
| | Negative Control | HIV-1 Group M control | HIV-1 Group O control | U14788 | U17609 | U17631 | U17849 | U17965 |
| Group O (MVP5180) | 0.086 | 0.807 | 1.102 | 0.304 | 2.974 | 1.189 | 2.742 | 2.654 |
| SIVgor | 0.056 | 0.162 | 0.053 | 0.614 | 2.196 | 2.79 | 1.266 | 1.354 |
| SIVcpz (ANT) | 0.064 | 0.098 | 0.055 | 0.488 | 0.171 | 3.46 | 0.568 | 0.081 |
| SIVcpz (GAB) | 0.057 | 0.131 | 0.061 | 0.359 | 0.198 | 0.105 | 0.13 | 0.089 |
| Group N (YBF30) | 0.0102 | 0.148 | 0.065 | 0.911 | 0.116 | 0.321 | 0.419 | 0.396 |

RT-PCR amplification using primers to HIV-1 group M and O in env gp41 amplified a fragment from the five plasma specimens. The viral sequence obtained from 4 of the specimens belonged to HIV-1 group M. Phylogenetic analysis of the 380 basepair sequence obtained from specimen U14788 showed the viral sequence branched with group P RBF168 sequence thus indicated U14788 was infected with a group P virus. The near full-length genome, designated 06CMU14788, was PCR amplified from proviral DNA extracted from a whole blood specimen of U14788. The genome was amplified as overlapping fragments using primers that had previously been used to amplify HIV-1 group M, N, or O. The genome sequence was assembled from 8 PCR fragments that were sequenced directly and 1 PCR fragment that was cloned prior to sequencing. The genome is 9238 nucleotides in length and encodes open reading frames for the structural and regulatory genes of HIV-1.

The complete genome sequence of 06CMU14788 was aligned with sequences for group P RBF168, SIVgor strains, and reference strains for HIV-1 groups M, N, and O. Phylogenetic analysis of this alignment generated the tree shown in FIG. 1. In the tree each HIV-1 group forms a distinct branch with branch length indicating genetic distance. 06CMU14788 and RBF168 cluster together on the same branch indicating they are the same group; group P is most closely related to SIVgor strains based on the branch pattern.

Comparison of Env Gp41 HLH Region

Figure 3:
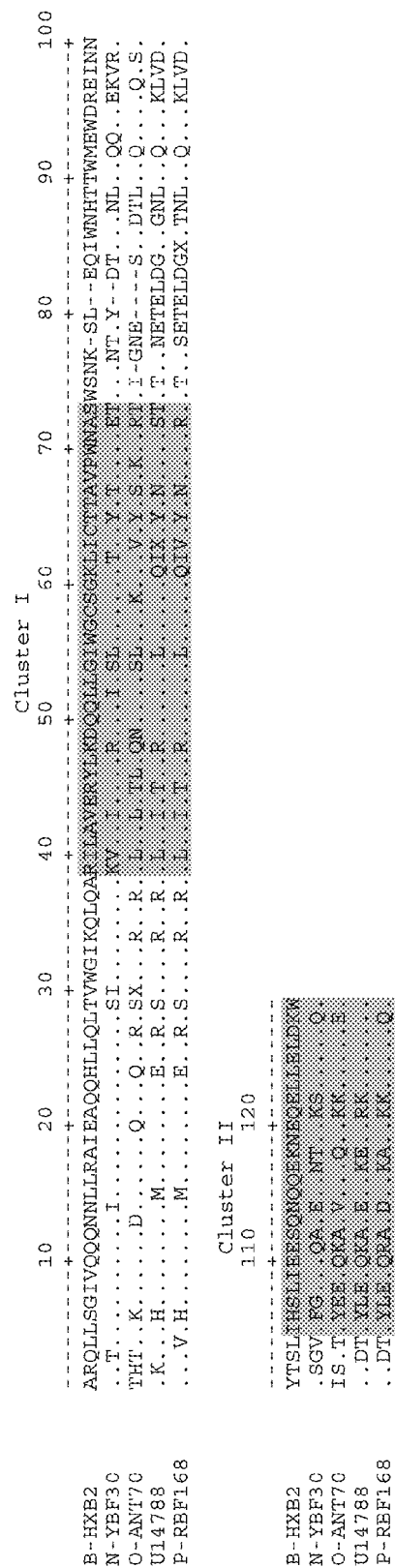
FIG. 3 is an alignment of the amino acid sequences of the
HLH regions of HIV-1 groups M, N, O, and P. Specifically,
the env gp41 helix-loop-helix region from HIV-1 group M
isolate HXB2 (SEQ ID NO: 36), HIV-1 group N isolate
YBF30 (SEQ ID NO: 37), HIV-1 group O isolate ANT70
(SEQ ID NO: 38), and HIV-1 group P isolates 06CMU14788
and RBF168 (SEQ ID NO: 39). A dash indicates identity to
06CMU14788 and a dot indicates no residue at that position.

The key epitopes for antibody detection of HIV infection lie in env gp41 helix-loop-helix (HLH) region with two key epitopes defined as Cluster I and Cluster II (see alignment in FIG. 3).

Within Cluster I, 06CMU14788 and RBF168 differ by 2-3 amino acids, and group P differs from HXB2 (group M isolate) by 11-12 amino acids. In Cluster II, 06CMU14788 and RBF168 differ by 5 amino acids, and group P differs from HXB2 by 11-12 amino acids. Group P differs from group N isolate YBF30 and group O isolate ANT70 in Cluster I by 8-9 and 11-13 amino acids respectively and in Cluster II by 7-10 and 4-6 amino acids respectively. Across the entire length of the HLH protein region, 06CMU14788 and RBF168 are 89.9% identical (13 amino acid differences). A comparison of 06CMU14788 to the representative group M, N, and O sequences shows percent identity to be 62.8, 65.1, and 66.7 respectively.

The amino acid sequence for the env gp120 V3 loop of 06CMU14788 is shown in FIG. 4, which has an alignment of the env gp120 V3 loop of 06CMU14788 and sequences obtained from 3 clones of this region of the genome that were amplified from the U14788 specimen. The tip amino acid sequences GVMTW (SEQ ID NO: 26) and GASTW (SEQ ID NO: 27) are unique to 06CMU14788; group P RBF168 has GPMTW (SEQ ID NO: 28), SIVgor strains have GPXTI where X can be either M or L (SEQ ID NO: 29), the group M consensus is GPGQASEQ ID NO: 30), consensus group N is GPAMT (SEQ ID NO: 31), and consensus group O is GPMAW_ (SEQ ID NO: 32).

Using peptides derived from group P IDR and V3 sequences in PEIAs allows unambiguous identification of HIV-1 group P infection (Table Y and Z). The IDR peptide used had the amino acid sequence RLLAIETYL-RDQQLLGLWGCSGQIVCYTNVPW (SEQ ID NO: 33) derived from 06CMU14788 and RBF168 and the V3 peptide has the sequence NTRGQVQIGPMTWYNMKFYTG (SEQ ID NO: 34) derived from RBF168.

TABLE Y

IDR PEIA Results

| IDR Peptide derived from | Specimen | | | |
|---|---|---|---|---|
| | Negative Control | HIV-1 Group M control | HIV-1 Group O control | Group P U14788 |
| Group M (HXB2) | 0.060 | 1.35 | 0.097 | 0.276 |
| Group O (ANT70) | 0.079 | 0.097 | 0.439 | 0.062 |
| Group O (MVP5180) | 0.120 | 0.216 | 0.158 | 0.107 |
| Group P | 0.088 | 0.097 | 0.055 | 0.938 |
| SIVgor | 0.053 | 0.093 | 0.061 | 0.150 |
| SIVcpz (ANT) | 0.092 | 0.146 | 0.077 | 0.095 |
| SIVcpz (GAB) | 0.049 | 0.063 | 0.05 | 0.117 |
| Group N (YBF30) | 0.084 | 0.081 | 0.048 | 0.136 |

TABLE Z

V3 PEIA Results

| V3 Peptide derived from | Specimen | | | |
|---|---|---|---|---|
| | Negative Control | HIV-1 Group M control | HIV-1 Group O control | Group P U14788 |
| none | 0.076 | 0.090 | 0.084 | 0.060 |
| Group M (HXB2) | 0.054 | 2.478 | 0.078 | 0.046 |

TABLE Z-continued

V3 PEIA Results

| V3 Peptide derived from | Specimen | | | |
|---|---|---|---|---|
| | Negative Control | HIV-1 Group M control | HIV-1 Group O control | Group P U14788 |
| Group O (ANT70) | 0.078 | 0.093 | 1.199 | 0.065 |
| Group P | 0.055 | 0.054 | 0.077 | 0.500 |
| SIVgor | 0.084 | 0.073 | 0.116 | 0.091 |
| SIVcpz (ANT) | 0.084 | 0.117 | 0.109 | 0.067 |
| SIVcpz (GAB) | 0.065 | 0.091 | 0.102 | 0.076 |
| Group N (YBF30) | 0.084 | 0.141 | 0.125 | 0.064 |

Figure 5:
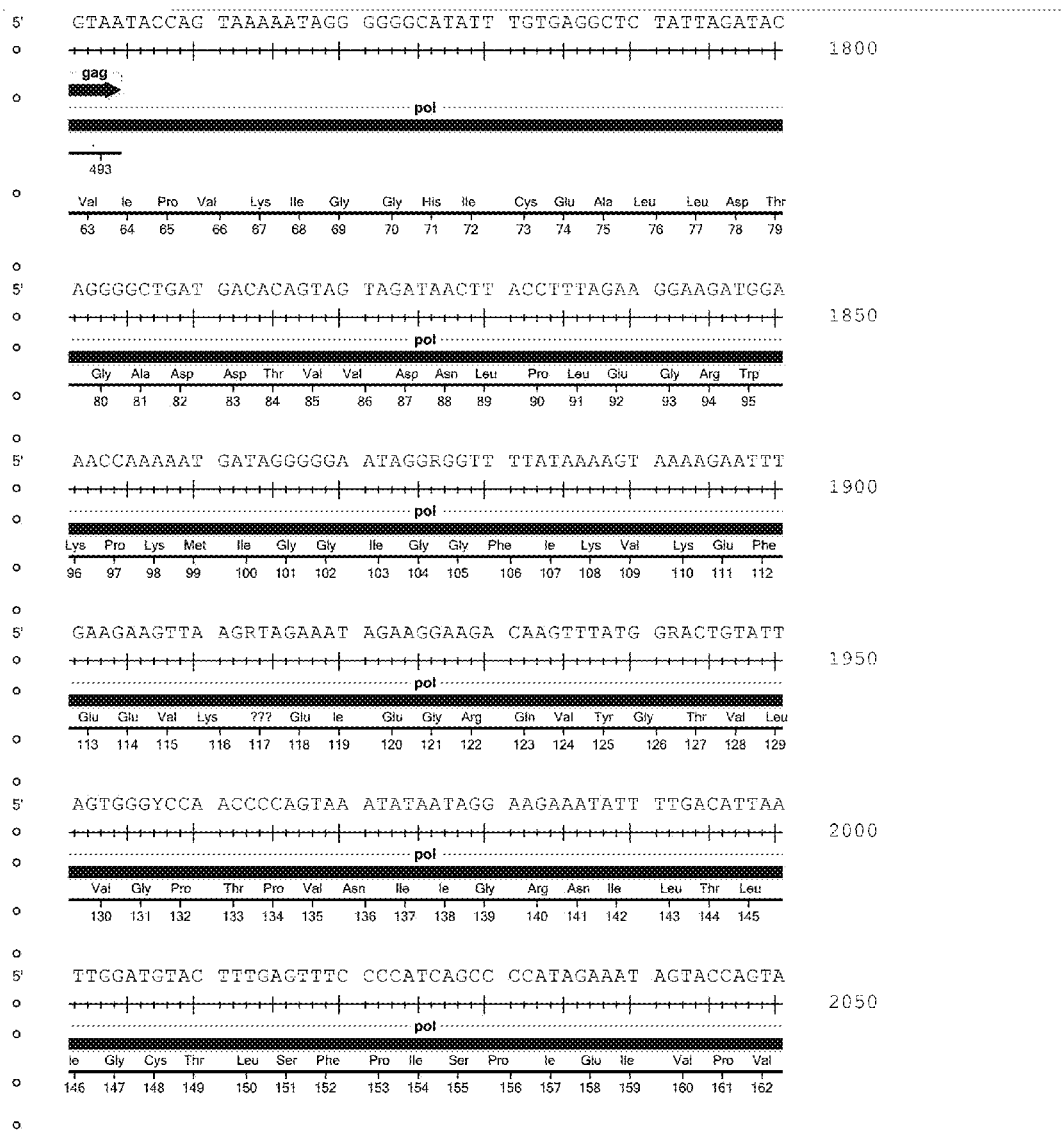
FIG. 5 is the 06CMU14788 nucleic acid sequence (SEQ ID
NO: 40) with genes mapped and translated into protein.
Figure 5:
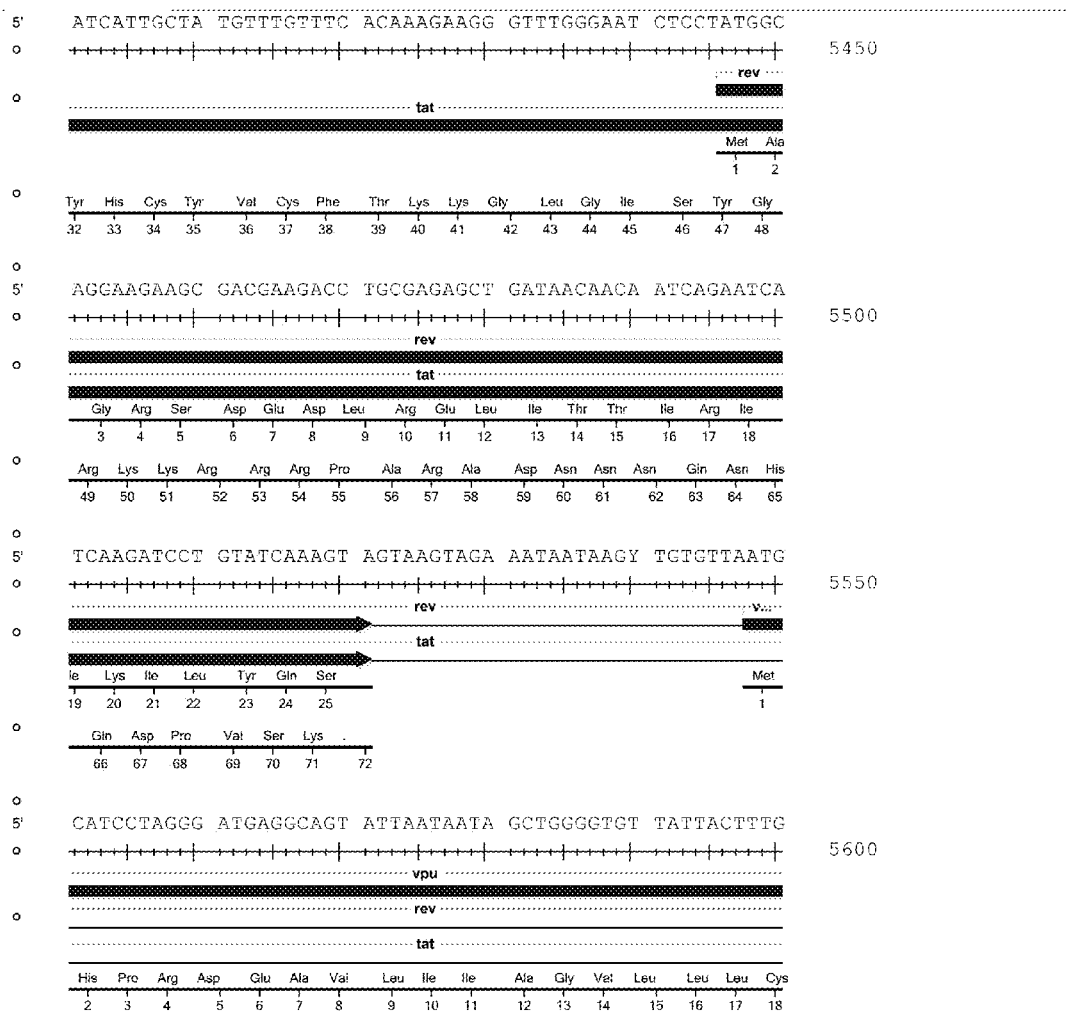
Figure 5:
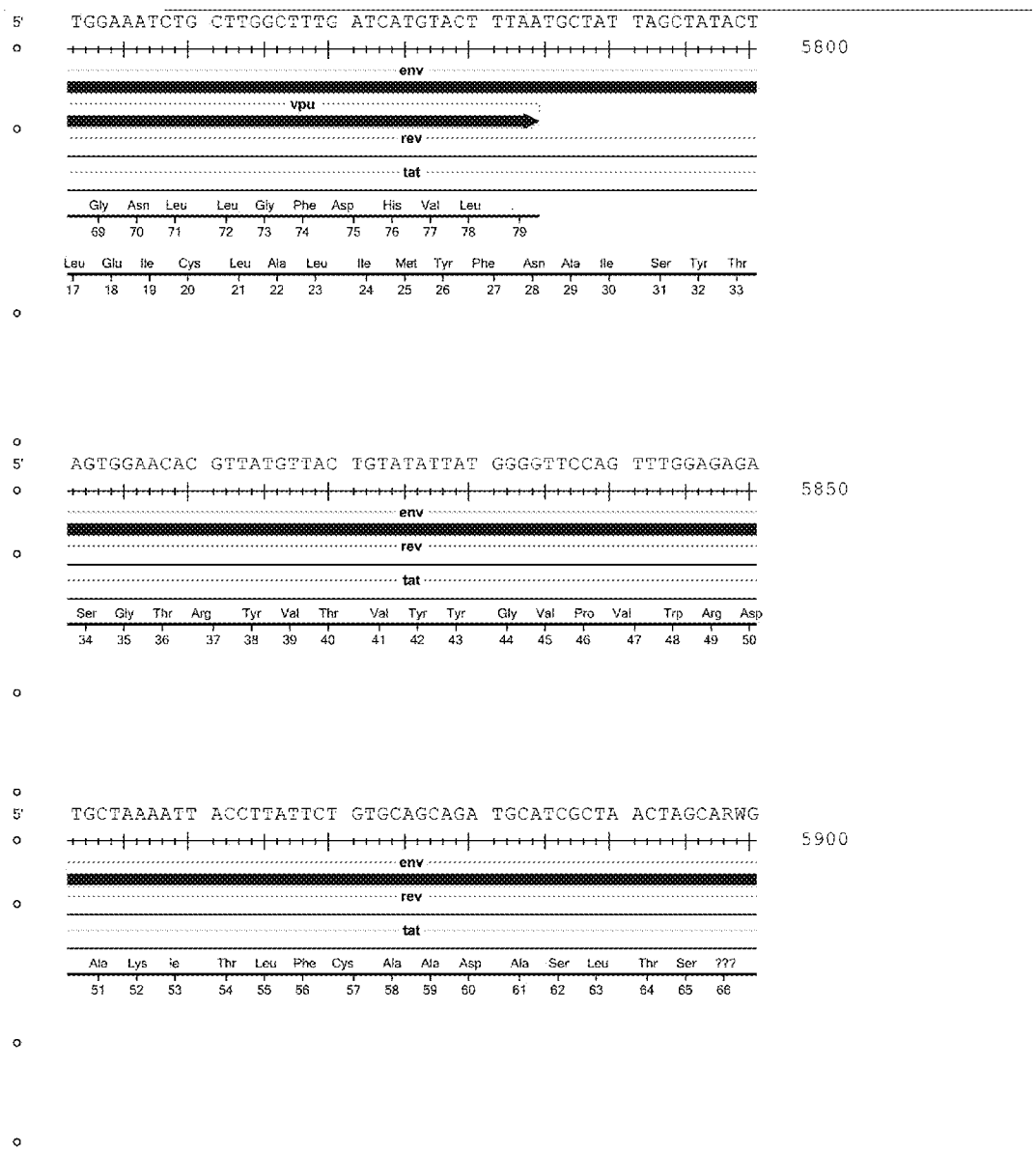
Figure 5:
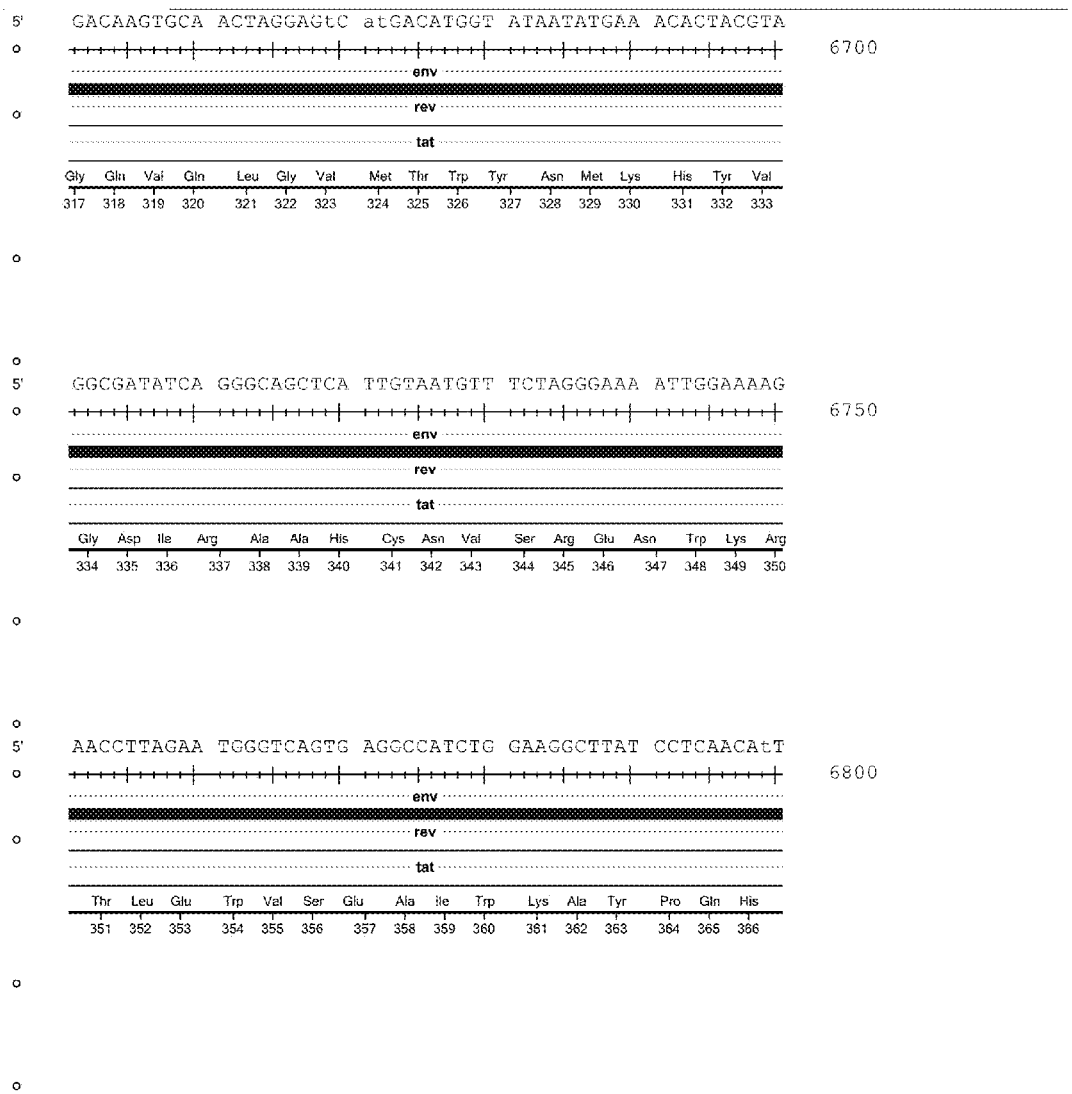
Figure 5:
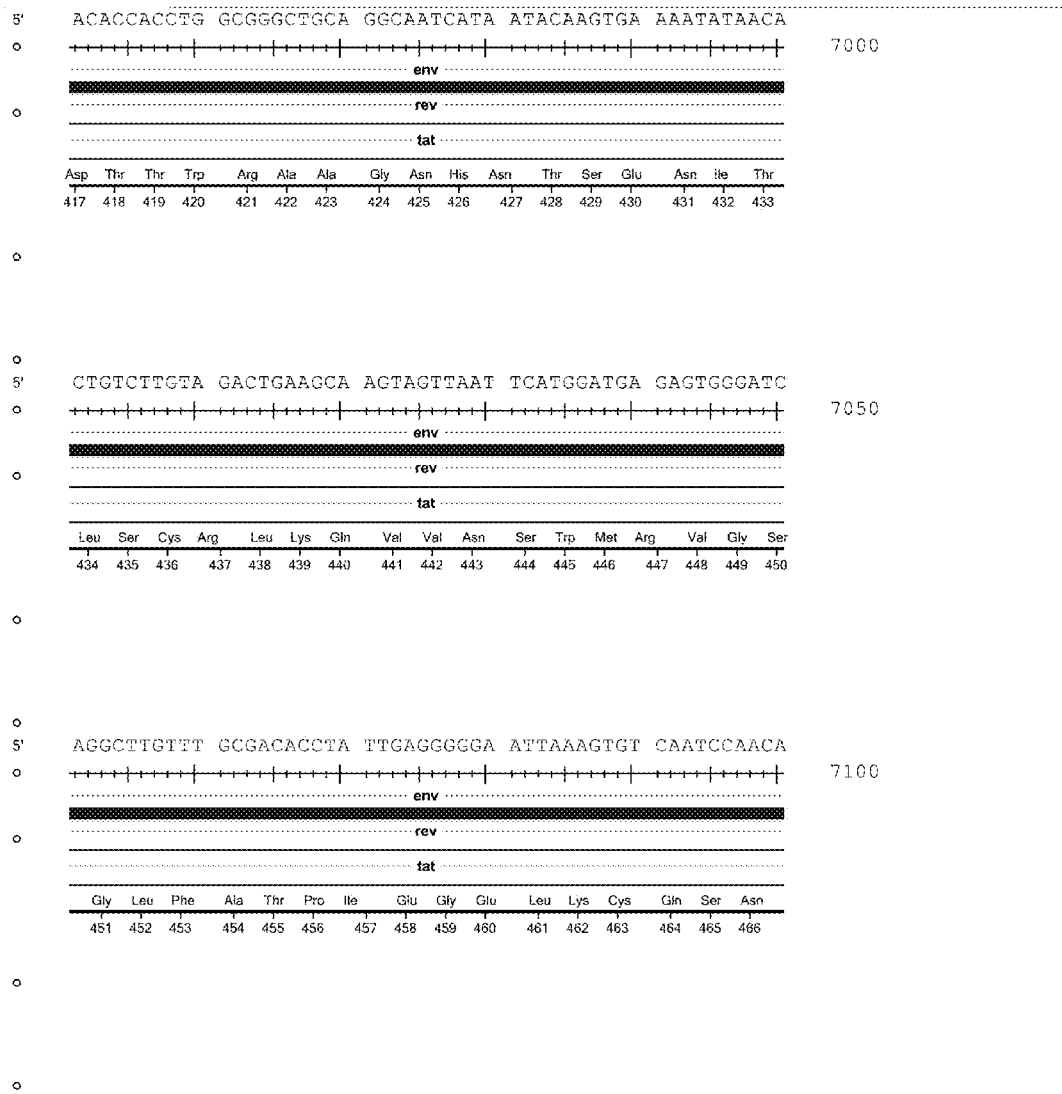
Figure 5:
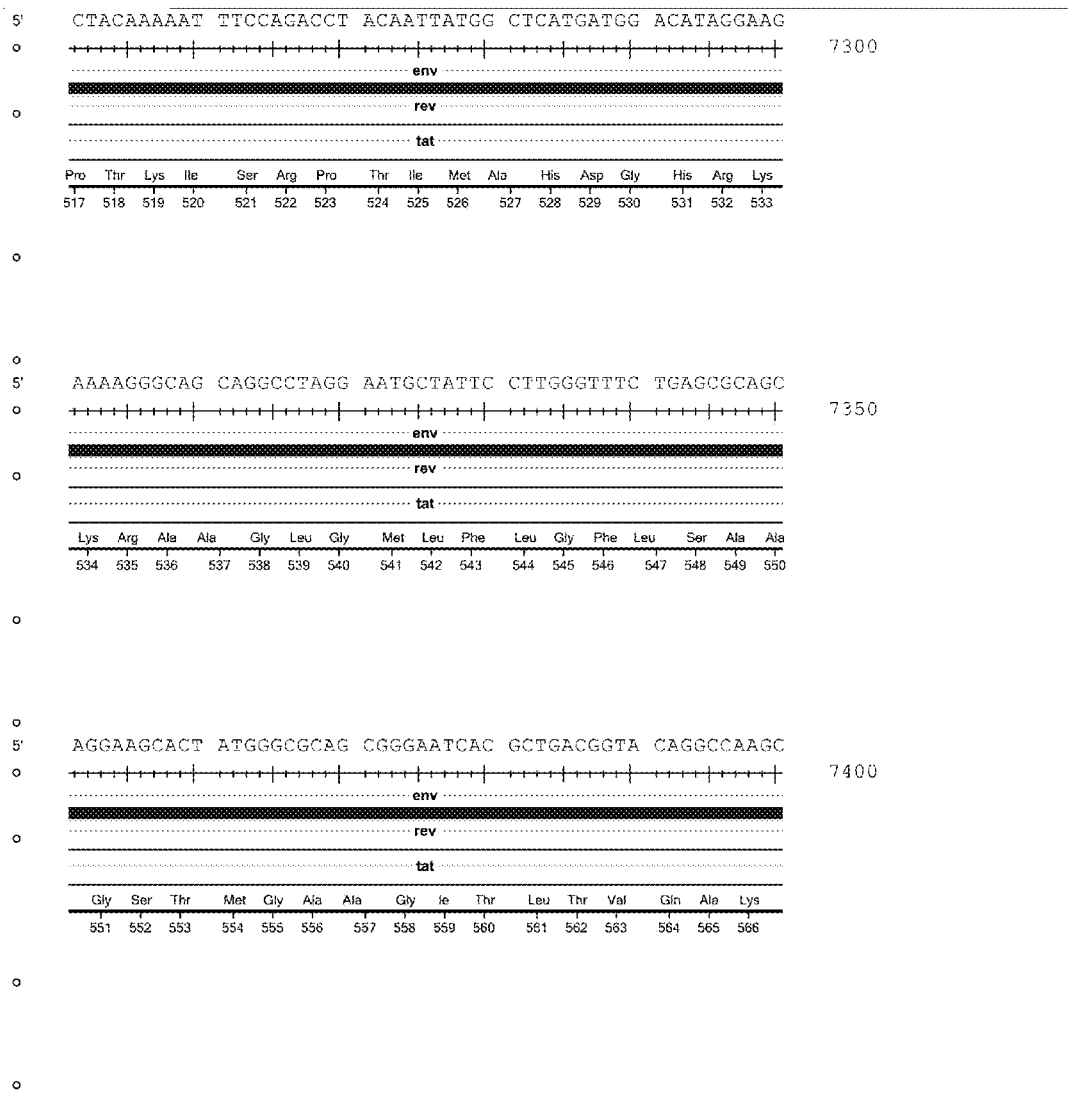
Figure 5:
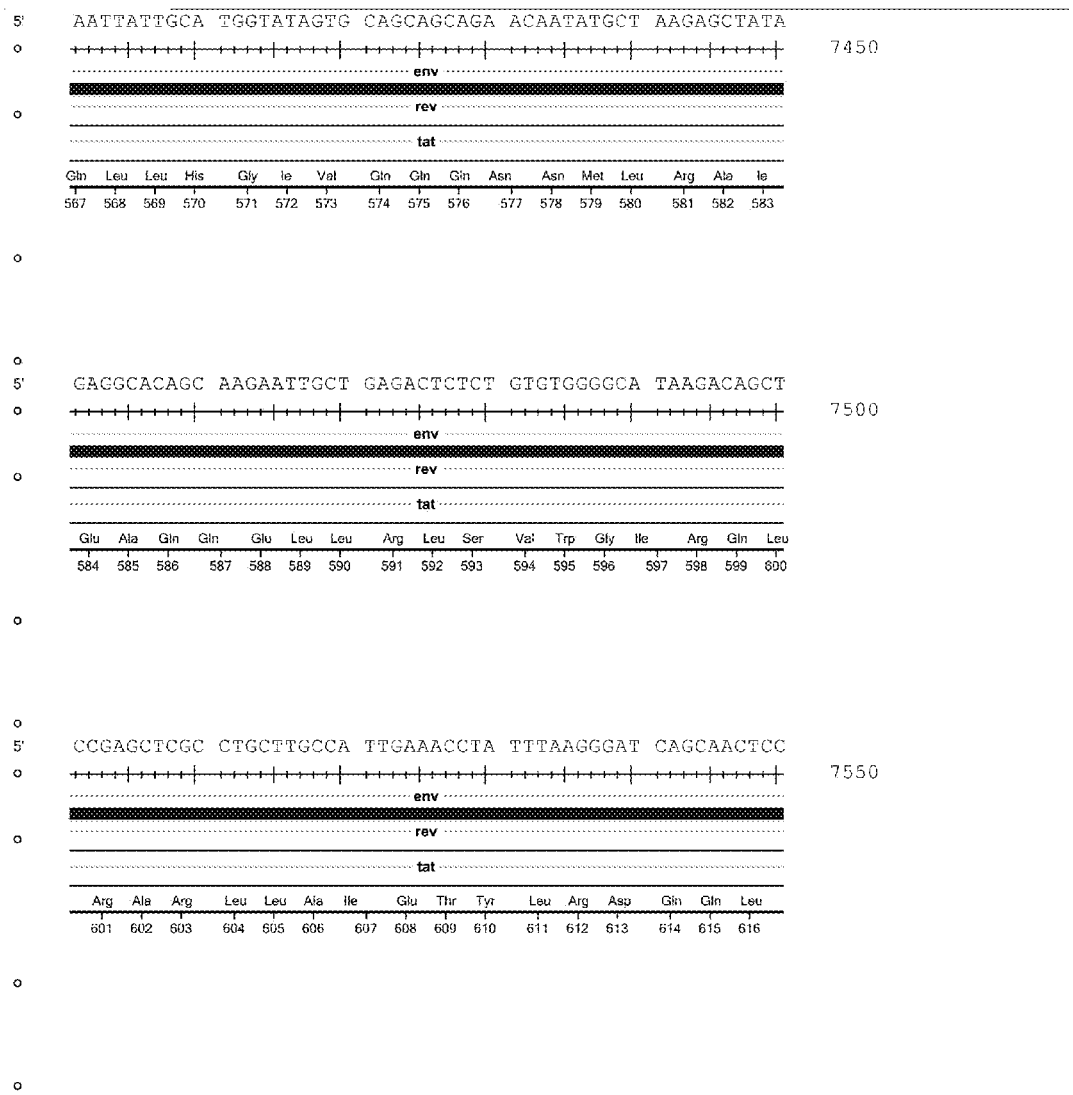
Figure 5:
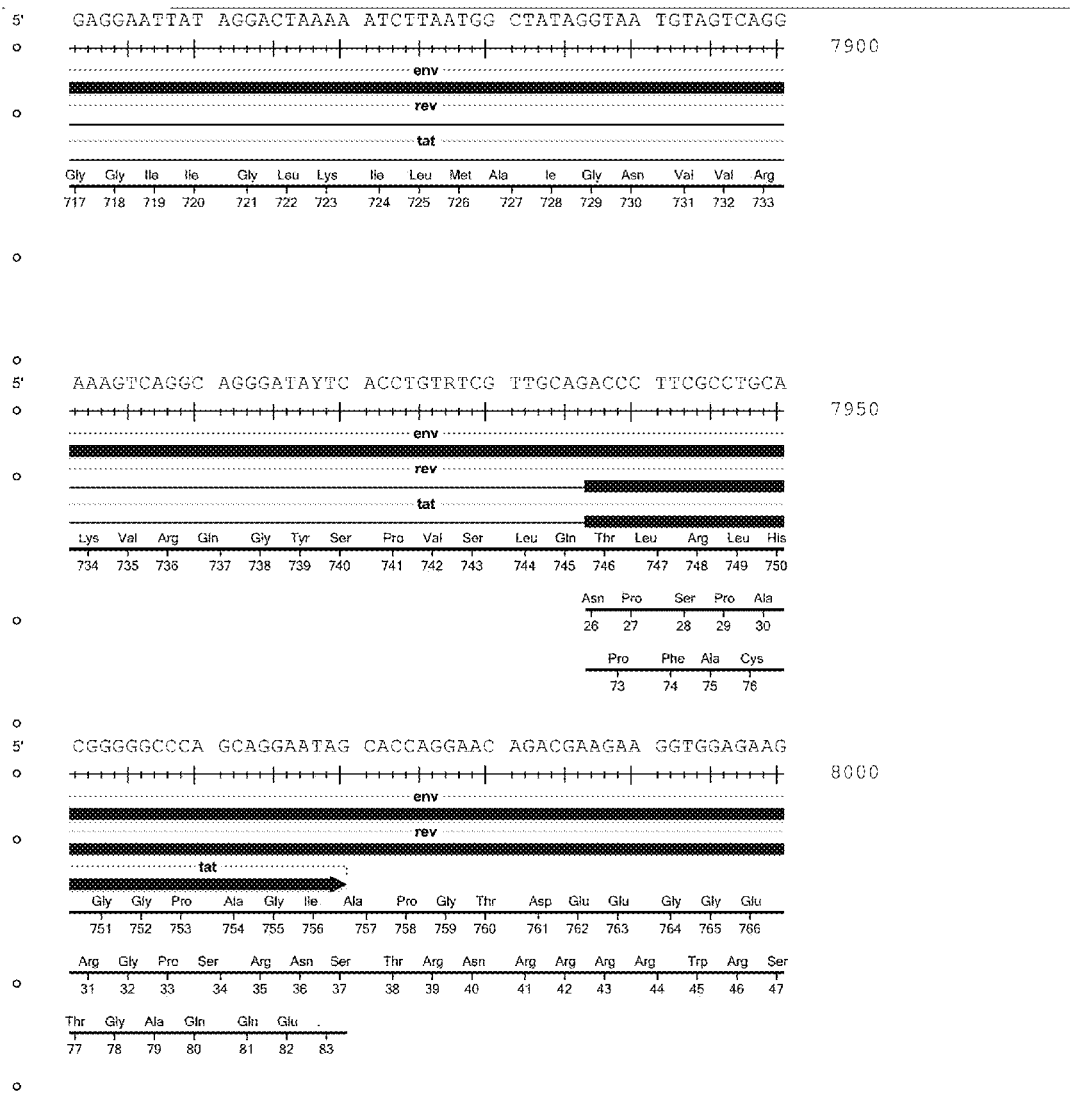
Figure 5:
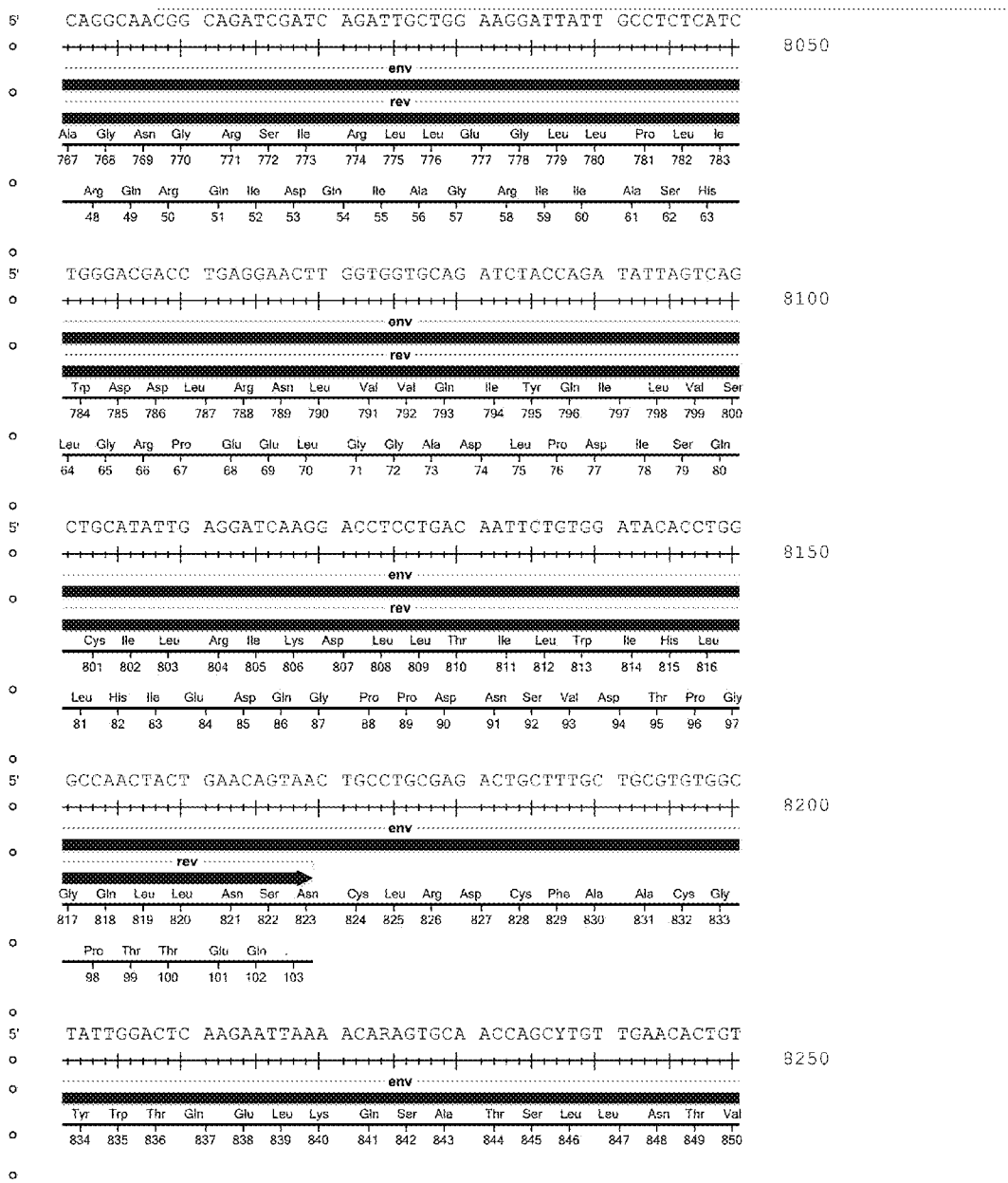

FIG. 5 is a translation of the U14788 nucleic acid sequence with genes mapped and translated. A comparison of the nucleic acid sequence of 06CMU14788 to RBF168 shows 92% identity in the genome region common to both sequences. By gene, nucleic acid sequence identity varies from 85% to 97.2% and translated amino acid sequence identity varies from 81.1% to 100%. See Table 1.

TABLE 1

Percent sequence identity* between 06CMU14788 and RBF168 viral genes

| Gene | Nucleic Acid | Protein |
|---|---|---|
| genome (region of overlap) | 92 | na |
| gag | 94.6 | 94.1 |
| pol | 94.5 | 94.8 |
| vif | 94.9 | 91.8 |
| vpr | 94.6 | 92.9 |
| vpu | 91.6 | 87.2 |
| tat | 97.2 | 100 |
| rev | 92.7 | 84.6 |
| env | 87.0 | 81.2 |
| nef (partial) | 85.0 | 81.1 |

*For sequence identity, deletions, insertions, and ambiguities were counted as differences.

EXAMPLE 2

Expression and Purification of HIV-1 Group P Recombinant Antigens

A. Design of the HIV-1 Group P rAg Constructs.

Based on homology to other HIV-1 groups, the Helix-Loop-Helix (HLH) region in env gp41 was thought to be the immune-domain region (IDR) for HIV-1 group P. An HLH amino acid comparison between HIV-1 groups M (HXB2, Genbank accession number K03455), N (YBF30, Genbank accession number AJ006022), and O (ANT70, Genbank accession number L20587) reference strains, and group P strain 06CMU14788 (Genbank accession number HQ179987) is shown in FIG. 6. The 06CMU14788 group P HLH protein has 63.5% sequence identity to the group M protein, 67.7% to group O, and 66.1% to group N based on analysis using Megalign v7.2.1 software (DNAstar Inc., Madison, Wis.).

Two HIV-1 group P rAg constructs were designed that encode the same amino acid sequence. The U14788 rAg used the native DNA sequence from 06CMU14788 and the HLH-P rAg used a synthetic DNA sequence with codon usage optimized for expression in *E. coli* (Guoy and Gautier, Nucleic Acid Res 10:7055-7074, 1982). An alignment comparing the U14788 rAg and *E. coli*-optimized HLH-P rAg sequences is shown in FIG. 6. Both constructs include an ATG codon at the 5'-end for translation start, an AAA codon spacer after the ATG start codon, six CAC codons at the 3'-end to encode a His-tag for protein purification, two stop codons, and EcoRI (GAATCC) and BamHI (GGATCC) restriction sites at the 5'- and 3'-ends, respectively, to facilitate cloning into the pKRR826 expression vector. These sequence modifications and the translated protein sequence are included in the alignment. Vector pKRR826 is a plasmid used for protein expression, and it has been described previously in Abbott patent U.S. Pat. No. 7,615,614 B2. Oligonucleotides were ordered from a commercial vendor (GenScript, Piscataway, N.J.) and the synthesized genes in vector pUC57 (Genbank accession number Y14837) were obtained.

B. Clone the DNA Fragments Encoding the rAgs into an Expression Vector.

The synthetic genes for the U14788 and HLH-P rAgs were cloned into expression vector pKRR826 using standard cloning methods (Sambrook et al., Molecular Cloning: A Laboratory Manual (Third Edition), Cold Spring Harbor Laboratory Press, 2001). The DNA fragments encoding the rAg synthetic genes were amplified from the pUC57 vectors using standard PCR (AmpliTaq DNA polymerase, Applied Biosystems, Branchburg, N.J.) and purification (ExoSAP-IT, USB Corporation, Cleveland, Ohio) reagents and manufacturers' protocols. The gene fragments and vector pKRR826 were digested with restriction enzymes EcoRI and BamHI (New England Biolabs, Ipswich, Mass.) and ligated together. The ligated DNA was transformed into DH5α *E. coli* competent cells (Invitrogen, Carlsbad, Calif.). The cells were grown on Luria Broth-agar plates containing ampicillin and 5-bromo-4-chloro-3-indolyl β-D-galactopyranoside (X-gal); ampicillin selected for colonies that had taken up the pKRR826 plasmid and the X-gal allowed for color screening to identify pKRR826 plasmids with the U14788 and HLH-P rAg genes inserted at the EcoRI and BamHI cloning sites. The plasmid DNA isolated from selected clones was sequenced to confirm the rAg constructs.

C. Express HIV-1 Group P rAgs.

Expression of U14788 and HLH-P rAg proteins was evaluated by growing cells containing each of the rAg plasmid constructs in liquid cultures at 32° C. Protein expression was induced by shifting the culture temperature from 32° C. to 42° C. Cells were harvested at various times post-induction. Cells collected at the different time points were lysed and run on a 4-12% gradient SDS/polyacrylamide gel (SDS-PAG) to evaluate rAg protein expression. FIG. 7A shows a gel stained with SimplyBlue Safestain (Invitrogen, Carlsbad, Calif.); the U14788 and HLH-P rAg constructs each express a protein with the expected molecular weight of 16 kilodaltons (kDa). FIG. 7B shows a Western blot of induction time point samples; cells were lysed in an SDS-based loading buffer and run on a 4-12% SDS-PAG and the proteins were transferred from the gel to a polyvinylidene difluoride (PVDF) membrane. Proteins containing the His-tag were detected using Mouse 6× His-tag (SEQ ID NO: 35) antibody (Abcam Plc, Cambridge, UK) as the primary antibody and alkaline phosphate-conjugated anti-Mouse IgG antibody (Invitrogen, Carlsbad, Calif.) as the secondary antibody. The Western blot confirmed that both U14788 and HLH-P rAg constructs express a protein containing the His-tag with the expected molecular weight of 16 kDa (FIG. 7B).

Samples were collected at time of induction (T0) and 1, 2, and 4 hours (T1, T2, and T4) post-induction, HLH-P rAg lanes 1-4 and U14788 rAg lanes 7-10. Cells were lysed in an SDS-based loading buffer and run on a 4-12% SDS-PAG. Proteins were visualized by staining the gel with SimplyBlue Safestain. The expected molecular weight for the U14788 and HLH-P rAgs is 16 kDa. The SeeBlue standard (lane 5) consists of 10 protein with molecular weights 4, 6, 16, 22, 36, 50, 64, 98, 148, and 250 kDa (bottom to top) (Invitrogen, Carlsbad, Calif.). The Mark 12 standard (lane 6) consists of 12 protein with molecular weights of 2.5, 3.5, 6.0, 14.4, 21.5, 31.0, 36.5, 55.4, 66.3, 97.4, 116.3, and 200 kDa (Invitrogen, Carlsbad, Calif.). Results are shown in FIG. 7A.

D. Purification of HLH-P Recombinant Antigen.

Figure 8A:
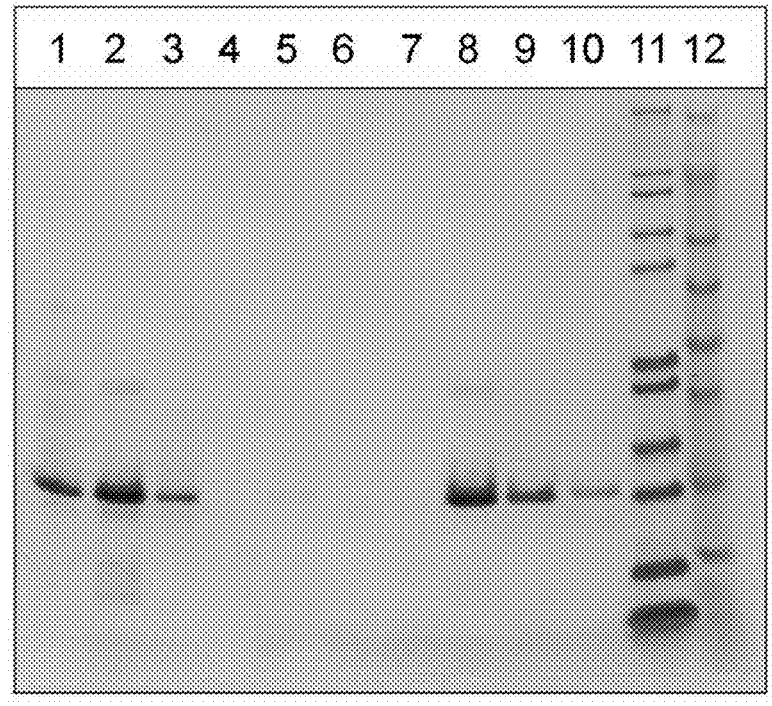
FIG. 8A. is a gel demonstrating the purification of U14788 rAg. Samples collected throughout the steps of protein purification were run on a 4-12% SDS-PAG and proteins were visualized by staining the gel with SimplyBlue Safestain. Lane 1: cell lysate; lane 2: guanidine-HCl solubilized cell pellet; lane 3: material not bound by resin during sample loading; lanes 4-7: resin washes after sample was loaded; lanes 8-9: eluted U14788 rAg; lane 10: resin stripped to remove proteins retained after elution steps; lane 11: Mark 12 standard; lane 12: See Blue standard. Molecular standards are as described for FIG. 7A.
Figure 8B:
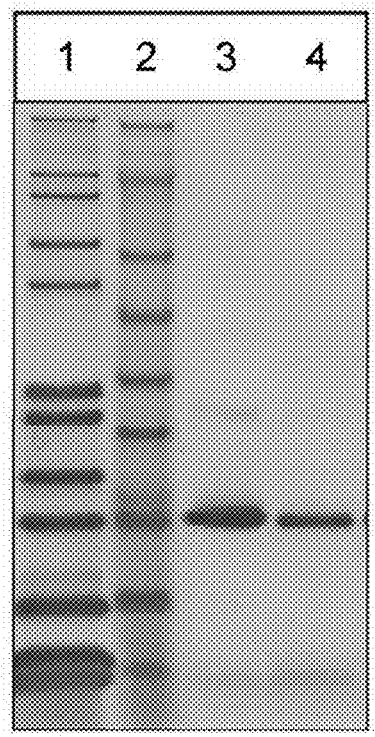
FIG. 8B. is a gel demonstrating the purification of HLH-P rAg. The same purification steps were used for HLH-P rAg as were used for U14788 rAg described in FIG. 8A. Lane 1: Mark 12 standard; lane 2: See Blue standard; lanes 3-4: eluted HLH-P rAg. Molecular standards are as described for FIG. 7A.
Figure 9:
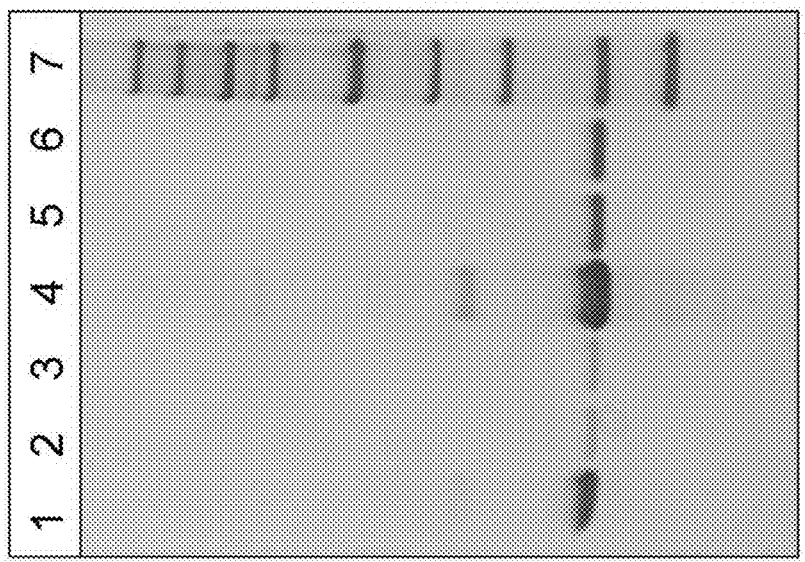
FIG. 9. is a SDS-PAG gel for determining the concentration of HLH-P rAg after purification. Proteins were visualized by staining the gel with SimplyBlue Safestain. Lane 1: 1 µg HLH-O rAg; lane 2: 0.15 µl HLH-P rAg preparation 1; lane 3: 0.16 µl HLH-P rAg preparation 2; lane 4: 4 µg HLH-O rAg; lane 5: 0.6 µl HLH-P rAg preparation 1; lane 6: 0.64 µl HLH-P rAg preparation 2; lane 7: Perfect Protein standard consisting of 9 protein bands with molecular weights of 10, 15, 25, 35, 50, 75, 100, 150, and 225 kDa (bottom to top). Each protein standard band contains 0.5 lag protein except the 50 kDa band contains 1 µg.

Cells containing the expression plasmids for U14788 and HLH-P rAgs were grown in liquid cultures and subjected to heat induction to induce expression of the rAg proteins. Several hours post-induction the cells were harvested by centrifugation. Based on previous HIV recombinant proteins expressed in the DH5α E. coli and pKRR826 expression system, the U14788 and HLH-P rAgs were expected to form insoluble protein aggregates, called inclusion bodies, within the cells. The cells were lysed and the inclusion bodies were collected by centrifugation and solubilized in a guanidine-HCl buffer. The proteins were purified using a His-Bind Purification Kit (Novagen, Gibbstown, N.J.). After purification, the guanidine-HCl was removed by dialysis and protein was stored in Tris-buffered saline with 2% SDS. FIG. 8A shows an SDS-PAG of samples collected during the protein purification steps of U14788 rAg beginning with the cell lysate through guanidine solubilization, resin binding, resin washes, and elution from the resin. FIG. 8B shows an SDS-PAG of the HLH-P rAg after elution from the resin using the same purification procedure. The U14788 and HLH-P rAg proteins behaved the same during purification; this is expected as the two rAgs have identical amino acid sequences. The protein concentration of the purified rAgs was determined by running aliquots of the final material on an SDS-PAG and comparing the protein bands to PerfectProtein protein quantitation standards, (EMD Chemicals, Inc., San Diego, Calif.) (FIG. 9).

E. Test HLH-P Recombinant Antigen for Detection of HIV Infection.

The immunologic reactivity of the HLH-P rAg was evaluated using an immuno-slot blot method (Hickman R, Vallari A, Golden A, et al., Journal of Virological Methods 72: 43-49, 1998). Recombinant proteins consisting of the amino acids of the HLH region from HIV-1 group M, group O and group P, and HIV-2 were coated onto nitrocellulose at two different protein concentrations (10 and 25 mg/mL) to create immuno-slot blot test strips. The HIV-1 group P rAg used in the immuno-slot blot was the HLH-P protein. The HIV-1 group M rAg, HLH-M, is derived from strain IIIB LAI (Genbank accession number A04321). The group O rAg, HLH-O, is derived from strain HAM112 (Abbott patent U.S. Pat. No. 7,615,614 B2). The HIV-2 rAg, HLH-2, is derived from strain D194 (Genbank accession number J04542). HIV-infected plasma specimens representing infections with HIV-1 groups M, N, O, and P (U14788) and HIV-2 were used to evaluate the ability of the HLH-P rAg to detect anti-HIV antibodies in the specimens. The results (FIG. 10) show that antibodies to HIV-1 group M, O, N and P were reactive to the HLH-P rAg and that antibodies to HIV-2 have a low level of cross reactivity to HLH-P rAg; the HIV-1 group P and O specimens had the strongest reactivity to HLH-P rAg followed by the group N specimen, group M, and then the HIV-2 specimen. The antibodies in the HIV-1 group P specimen U14788 reacted the strongest to the HLH-P rAg but also had strong reactivity to the HLH-M and HLH-O recombinant proteins and low reactivity to the HLH-2 protein (FIG. 10, lane 6). Under the conditions used in the slot blot assay, there was cross reactivity of all HIV-1 specimens with all HIV-1 recombinant proteins.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An isolated nucleic acid of an HIV-1 Group P virus, wherein the nucleic acid consists of SEQ ID NO: 1 and the isolated nucleic acid is labeled with a radioactive compound or with a nonradioactive compound.

2. The isolated nucleic acid of claim 1, wherein the nonradioactive compound comprises biotin, acetylaminofluorene, digoxigenin, 5-bromodeoxyuridine, or fluorescein.

* * * * *

SEQUENCE LISTING

```
<160> NUMBER OF SEQ ID NOS: 43

<210> SEQ ID NO 1
<211> LENGTH: 9238
<212> TYPE: DNA
<213> ORGANISM: Human immunodeficiency virus

<400> SEQUENCE: 1
taaagcttgc cttgagtgag taaagcagtg tgtgctcatc tgttcagact ctggtatcta      60
gagatccctc agagcacttt tagccgagtg aaaaatctct agcagtggcg cccgaacagg     120
```

```
gacctgaaag tgaaaccagt ttctgaaacc tccgacgcac gggctcggct cagcggagtg    180
cacctgctga gaggcgagag gaactcacgg cggtgagtac attttgtcag tggtgactga    240
ccctagggga agaggcgaag tctctagggg aggagatggg tgcgagagcg tcagtgttga    300 caggggccg attggatgca tgggaaagaa ttaggcttag accaggaggt aagaaaaaat     360
ataagctaaa acatgtagta tgggcaagca gagagctgga aagatttgca tgtaatcctg    420
ggcttatgga acagcggaa ggctgcgaaa aattattaga gcagttagaa ccagctctca     480
gaacaggctc ygatggcctg cagtctcttt ggaacaccct agtagttyta tggtgtgttc    540
acaaaagaat agagataagt gacacacagc aggccattac aaaatggaag gaggaaatgc    600
agaaaagaaa gaaaacatca gagggcagca ctggaacaag tcaaaactat cctatcgtgc    660
agaatgccca ggggcaaatg acccatatgc cgctgtcccc caggacgctg aatgcctggg    720
tgaaggcagt agaagaaaaa gccttcaacc ctgaaattat ccctatgttt atggccttgt    780
cagaaggggc tatacctgat gacatcaata ccatgcttaa tgcagtaggc ggacatcagg    840
gagcgttgca ggtgttgaaa gaggtaatta atgaagaggc tgcagaatgg gatagaacac    900
atcccgttcc agtaggacca ttaccaccag ggcagcttag agaaccaaca ggaggggata    960
ttgcaggaac cactagtacc aaacaggaac agataacctg gatgacaagg aacaatcctg   1020
taccagtagg ggacatctat agaaartgga tagtgttggg gctcaataaa gtggtaaaaa   1080
tgtactgccc cgttagcatt ctggacataa agcaggacc taaggaacca tttagagatt   1140
atgtagayag attctacaaa accctcagag cagagcaagc cagtcaggaa gtaaaaagtt   1200
ggatgacaga caccttacta gtacaaaatg ctaatccaga ttgyaagcag attttgaaag   1260
ctctgggacc aggtgccacc ttagaagaaa tgatgaatgc ctgtcaagga gtaggggac    1320 caacacataa ggccagggtc ttggcagaag ctatggcagc agctaatcaa gctagccaag   1380
aattaaaagg agggtataca acagttttta tgcagagtgg acagagaaag ccagttaagt   1440
gctttaactg tggaaaagta ggacacatag caaagaactg caaggcacct agaagaaggg   1500
grtgttggaa gtgtggacag gaaggtcatc aaatgaaaga ctgcaaatca ggaagacagg   1560 caaattttt agggaagatc tggcctccgg ggggcaagag gccaggcaac tatgtacaga   1620
aacaagtaca accgacagcc ccacctatgg aggaggagga gatgactcag aacaagcaga   1680
rggaggaaaa ggaggacgag aaagagttgt acccttagc ctccctcaaa tcactctttg    1740
ggacagacca gtaataccag taaaaatagg ggggcatatt tgtgaggctc tattagatac   1800
aggggctgat gacacagtag tagataactt accttagaa ggaagatgga aaccaaaaat    1860 gatagggga ataggrggtt ttataaaagt aaaagaattt gaagaagtta agrtagaaat    1920
agaaggaaga caagtttatg gractgtatt agtggggycca accccagtaa atataatagg   1980
aagaaatatt ttgacattaa ttggatgtac tttgagtttc cccatcagcc ccatagaaat   2040
agtaccagta aaattaaaag caggaatgga tgggcctagg gtgaagcaat ggcccttgtc   2100
aaaggaaaaa atagaagctt taagagccat ctgtcaagag atggaacagg aaggaaaaat   2160
aacaaaaatt gggcctgaaa atccatataa caccccccatt tttgcaataa aaagaaaaga  2220 tgcagcaag tggaggaaat tagtagactt cagagaacta aataaaagaa cacaagattt    2280
ctgggaagtc caattgggra tccctcatcc aggaggtctt cagaaaagra aatcagtgac   2340
catattagat gtaggrgatg cttatttctc ctgyccttta gatccagatt ttagaaaata   2400
tacagctttc actataccta gtgtaaataa tgacacacca ggacttagrt atgtgtayaa   2460
tgttctgcct cagggatgga aaggatcacc agccatttty cagcattcaa tgactaagat   2520
```

```
cttagaaccc tttagraaga gtaatccaga agtagaaatc taycaataca tggatgatyt    2580
atatgtaggg tcagatytgc ctttgtctga acatagacag cgggtagaga aactyaggga    2640
rcacctctat gtatgggggt tcacaactcc tgacaaaaar catcaaaagg agcctccttt    2700
cctctggatg ggatatgagc tccatcctga caagtggack gtgcaaccca tcaaattacc    2760
agaaaaggaa agttggacag taatgacat tcagaagcta gtaggaaagt taaattgggc     2820
tagtcaaatt tatccaggaa ttagggtaaa agagttatgy aaactaatta gaggaactaa    2880
rtccttaaca gaagtagttg cytttactag agaagcagaa ttagaactag aggaaaataa    2940
agaaattta aaagaaccag tgcatggagt ttattaccaa ccagaaaagg aattaatagt     3000
agacatacag aaacagggg cgggacaatg gacttatcag gtattccagg aagaacataa     3060
aaacttgaaa acagggaaat atgccaggca aaaggctacc cacaccaatg atataaggca    3120
actggcagar gtaatacaga aggtatcaca agaaagcata gtgatatggg gaaaactacc    3180
caagtttaga ctaccagtaa atagaaatgt gtgggagact tggtggtcag actattggca    3240
agccacctgg atacctgagt gggaatttgt tagcacaccc cctcttatta agctctggta    3300
tcagctagaa aaagacccca taccaggaac agaaaccttt tatgtagatg ggcagcaaa     3360
cagagagacc aagttaggya aagctggata tgtaacagat aggggtaggc agaagataat    3420
caaactagaa garacaacta atcaaaargc agaattagaa gcagtgttgt tagccttaaa    3480
agaatcagga gaacaggcta acatagtaac agactcccaa tatgtgttag grattatctc    3540
agcaactcca gatcaaagtg actccccyt agtgcaaaaa ataatagaag aaatgacaaa     3600
aaaggaaaag gtatacctrt catgggtacc agcacacaaa ggcataggg gtaatgaraa     3660
yatagayaaa ttagtcagya argacattag aagagtgtta ttcttggaag gcatagacca    3720
agcacaggag gatcatgaaa atatcacag taattggaga gccctagcta gtgartttgg     3780
ccttccacca atagtggcaa aagagattat yaacaattgc cctaaatgtc atgtaaaagg    3840
ggaagccatg catggacagg tagactgcag tccaggaatt tggcaactgg actgtaccca    3900
catggargga aaaattatcc tcgtggcagt ccatgtrgcc agtggcttca tggaagcaga    3960
agtaattcca gtagaaacag gacaagaagc tgcatacttt gtgctcaaat tggcatcaag    4020
atggcctgta aaagtaatac acacagacaa tgggcctaac tttactagcg ctgcagtaaa    4080
agcagcctgt tggtggctta atataactca tgagtttggg atacctaca atccccaaag    4140
tcagggagta gtggaatcaa tgaataaga attaaagaaa attatacatc aggtacgaga    4200
tcaagctgag cacttaaaga cagcagttca aatggcagta tttgtccaca attttaaaag    4260
aaaaggggg attgggggt acactgctgg agacaggatc atagatattc tggctacaca    4320
ratacaaaca acagaattac aaaaacaaat tttaaaatt caaaattttc aggtctatta    4380
cagagacagc agagaccct tttggaaagg accagcgaca ctcctgtgga aaggtgaagg    4440
ggcagtagtc atacaagaca aaggagatat taaggtagtc cctaggagaa aagcaaaaat    4500
aattagaaat tatggaaaac agatggcagg tgatgattgt gtggcagata cccagagaga    4560
aagtgaaagc ctggaacagt ctggttaaat atcacaaata taggtctaaa aagacaagaa    4620
agtggtttta taggcatcat tatgagacaa cccatcctag gattagttca gcagtttata    4680
ttccagtagg aacagcaacc attattgtga ctacytattg ggggctcatg cctggggaaa    4740
gagaagaaca attaggacat ggagcaagtg tggagtggag acaaggtaaa tacaccacac    4800
agatagatcc agaacagca gataggctaa ttcatctcca ctactttcaa tgttttcag    4860
attcggctgt gaggagggca atactagggg acagggtatt gaayamatgt gaatactcag    4920
```

```
caggacatag tcaggtaggc tccttgcagt atttagcctt aaaagtggta gtagggaagg    4980
taaaraggaa gccaccoctc cctagtgtcc agatattgac acaagacata tggagcaacc    5040
cccagaggac caagggccrc caagagagcc attcaatgag tggatgctac aaaccttaga    5100
ggaactcaag gaggaagcag taagacactt ccctaggcct tggttacact cattaggaca    5160
gtatatctat aatacctatg gggacacctg ggagggagta actgcaatta ttaggatcct    5220
acaacaatta atytttatcc attatagaat tggatgccaa catagtagaa taggtatctt    5280
gacaccctct cgaagaggaa ggagacatgg acccagtaga tcctgatctg cctccatggc    5340
aacagccagg gagtcagccc tcaagcccat gtaacaattg ctactgcaaa gcctgctgct    5400
atcattgcta tgtttgtttc acaaagaagg gtttgggaat ctcctatggc aggaagaagc    5460
gacgaagacc tgcgagagct gataacaaca atcagaatca tcaagatcct gtatcaaagt    5520
agtaagtaga aataataagy tgtgttaatg catcctaggg atgaggcagt attaataata    5580
gctggggtgt tattactttg ctgtatagta gyttgggggga aggtcctyct attagtgcta    5640
aaagaaagag aaagrgataa gtttgtrcaa aggctagcaa ggtggagaga agggcaagaa    5700
gatgaggggt atgaaagtaa tgaagaagaa gaagaacagc ttagggaact tggaaatctg    5760
cttggctttg atcatgtact ttaatgctat tagctatact agtggaacac gttatgttac    5820
tgtatattat ggggttccag tttggagaga tgctaaaatt accttattct gtgcagcaga    5880
tgcatcgcta actagcarwg agcagcataa tatttgggcc acccaggcct gtgtgcccac    5940
agaccctaga ccaatagagg tcaggataga taatgtaaca gagtcttta atatttggga    6000 caattatatg gtgacacaaa tgcaggaaga catcattagc ttatgggatc agagccttaa    6060
accttgtgta aaattgacag ttctatgtgt tactatgrat tgtagcgact gcagcacggt    6120
tgactgtact aataactcct ccagggttaa taacagcacc gacagcacca acaccagcaa    6180
aaccaatcca ttagaattat ttcagtgcag ttttaataca accacaatag taaaagataa    6240
acagcagaca cagcaagcac tcttttatag agcagaccta acaaaattgg ataatgacaa    6300
tagtacatat agattaatta attgcaacac cactaccatt acacaggcat gcccaaaagt    6360
gaactttgag ccgctaccca tacagtattg tgcaccagca gggtatgcac taatgaaatg    6420
caatcagaca ggatttaatg gtacaggacc ttgtaataag acagttataa cacactgtac    6480
acatggaatt aagccaacag tgtcaacaca attaatactc aatggaactc tagcaaaggg    6540 agagcccta gtaattactc agaatgtgtc agatacagga aaagtcatca tagtaaaatt    6600
aaatgagagt gtgtcactca cctgtataag accaggtaat aacacaagag gacaagtgca    6660
actaggagtc atgacatggt ataatatgaa acactacgta ggcgatatca gggcagctca    6720
ttgtaatgtt tctagggaaa attggaaaag aaccttagaa tgggtcagtg aggccatctg    6780
gaaggcttat cctcaacatt ccaaccatac atccaaacac aaccatacat tgtttttaa    6840 aaacagtaca gggggagacc cagaggtttc ttcgctgcac ttcagttgtc atggggaatt    6900 ctttattgt aacaccagca gcctgtttaa ctttagttat acttggaatg acaccacctg    6960
gcgggctgca ggcaatcata atacaagtga aaatataaca ctgtcttgta gactgaagca    7020
agtagttaat tcatggatga gagtgggatc aggcttgttt gcgacaccta ttgaggggga    7080
attaaagtgt caatccaaca ttacaggttt aatgttagaa agagaactac cttacaatga    7140
cagcagcaag aacaccactt taagtcctat aggggagac atgacaaata tctggagaag    7200
tgagttatat ccctacaaag tagttcaagt aaaagctctg gccgtggcac ctacaaaaat    7260
ttccagacct acaattatgg ctcatgatgg acataggaag aaaagggcag caggcctagg    7320
```

```
aatgctattc cttgggtttc tgagcgcagc aggaagcact atgggcgcag cgggaatcac    7380
gctgacggta caggccaagc aattattgca tggtatagtg cagcagcaga caatatgct     7440 aagagctata gaggcacagc aagaattgct gagactctct gtgtggggca taagacagct    7500
ccgagctcgc ctgcttgcca ttgaaaccta tttaagggat cagcaactcc taggactgtg    7560
gggatgctca ggacaaatar tatgttatac taatgtgcca tggaatagta cctggaccaa    7620
caaaaatgaa acagaattag atggcatttg ggtaatcta acatggcagg agtgggacaa     7680
actggtggat aattacactg acacaattta cttggaaata cagaaagcac aagagcagca    7740
gaaggaaaat gaagaaaagc tattagaatt agacaaatgg gcacaattgt ggagctggat    7800
ggacataaca aaatggttgt ggtacataaa aattttcatt atgatagtag gaggaattat    7860
aggactaaaa atcttaatgg ctataggtaa tgtagtcagg aaagtcaggc agggataytc    7920
acctgtrtcg ttgcagaccc ttcgcctgca cggggccca gcaggaatag caccaggaac     7980
agacgaagaa ggtggagaag caggcaacgg cagatcgatc agattgctgg aaggattatt    8040
gcctctcatc tgggacgacc tgaggaactt ggtggtgcag atctaccaga tattagtcag    8100
ctgcatattg aggatcaagg acctcctgac aattctgtgg atacacctgg gccaactact    8160
gaacagtaac tgcctgcgag actgctttgc tgcgtgtggc tattggactc aagaattaaa    8220
acaragtgca accagcytgt tgaacactgt tgctatatca gttgcaaatt ggactgatca    8280
agtaatagca gtagggcaac aaataggaag aggcttcttg aacataccaa gaaggttaag    8340
acaagggcta gaaagaagct tactgtaaaa tggggaatgc atggaagaaa agtagcttag    8400
tgggctggcc agcagtcagg gaaaaaataa agcagactac cccgactacc cctgacccga    8460
ctaccccagt aacacctgca cccggggttg gggaaatttc caaagaatta gcacaaggaa    8520
aaggaatacc cagtaaattt agttcaaaga acaatgcagc atttggcttc ttggatgctc    8580
atgaggaaga agaagtaggr ttcccagtca ggcctcaagt acccttaaga tgcatgacat    8640
acaaggcagc atttgacctc agcttctttt taaaagaaaa gggaggactg gatgggttag    8700
tttactcacc tgagagagca gagatcctag atctctggat ctatcacact cagggattct    8760
tccctgactg gcagaattac actccagggc caggagaaag atatcccctg acctttgggt    8820
ggctgtttaa actagtacca gtctctgagg tagaagctga ggaaatggga gataagcagg    8880
agaaagctaa gctgctacat ccagcctgca cttatgggtt ttcagatcct cataaggaga    8940
tcctagtgtg gaagtttgac agctcacttg gaagagaaca tgttgcctta caaaagcacc    9000
cggaactgtt tattaaagac taaattgctg acgccacgta gctgctaaag ctgctgacac    9060
tgcagggact ttccggggac ggaaagtccc gagggcggaa caaggggagg agcaggggag    9120
tggtttcacc ctcagagctg catataagca gctgcttcac gcttgtactg ggtctctgtg    9180
acagaccaga ttagagcctg ggagctctct ggtctaagca gaacccactg gttaaaaa     9238
```

<210> SEQ ID NO 2
<211> LENGTH: 1476
<212> TYPE: DNA
<213> ORGANISM: Human immunodeficiency virus
<400> SEQUENCE: 2

```
atgggtgcga gagcgtcagt gttgacaggg ggccgattgg atgcatggga agaattagg       60 cttagaccag gaggtaagaa aaaatataag ctaaaacatg tagtatgggc aagcagagag     120
ctggaaagat ttgcatgtaa tcctgggctt atggaaacag cggaaggctg cgaaaaatta     180
ttagagcagt tagaaccagc tctcagaaca ggctcygatg gcctgcagtc tctttggaac     240
```

```
accctagtag ttytatggtg tgttcacaaa agaatagaga taagtgacac acagcaggcc      300
attacaaaat ggaaggagga aatgcagaaa agaaagaaaa catcagaggg cagcactgga      360
acaagtcaaa actatcctat cgtgcagaat gcccagggc aaatgaccca tatgccgctg       420
tcccccagga cgctgaatgc ctgggtgaag gcagtagaag aaaaagcctt caaccctgaa      480
attatcccta tgtttatggc cttgtcagaa ggggctatac ctgatgacat caataccatg      540
cttaatgcag taggcggaca tcagggagcg ttgcaggtgt tgaaagaggt aattaatgaa      600
gaggctgcag aatgggatag aacacatccc gttccagtag gaccattacc accagggcag      660
cttagagaac aacaggagg ggatattgca ggaaccacta gtaccaaaca ggaacagata       720
acctggatga caaggaacaa tcctgtacca gtaggggaca tctatagaaa rtggatagtg      780
ttggggctca ataaagtggt aaaaatgtac tgccccgtta gcattctgga cataaagcag      840
ggacctaagg aaccatttag agattatgta gayagattct acaaaaccct cagagcagag     900
caagccagtc aggaagtaaa aagttggatg acagacacct tactagtaca aaatgctaat      960
ccagattgya agcagatttt gaaagctctg ggaccaggtg ccaccttaga agaaatgatg     1020
aatgcctgtc aaggagtagg gggaccaaca cataaggcca gggtcttggc agaagctatg     1080
gcagcagcta atcaagctag ccaagaatta aaggagggt atacaacagt ttttatgcag      1140
agtggacaga gaaagccagt taagtgcttt aactgtggaa agtaggaca catagcaaag      1200 aactgcaagg cacctagaag aagggrtgt tggaagtgtg acaggaagg tcatcaaatg      1260 aaagactgca aatcaggaag acaggcaaat ttttaggga agatctggcc tccgggggc      1320 aagaggccag gcaactatgt acagaaacaa gtacaaccga cagcccacc tatggaggag     1380 gaggagatga ctcagaacaa gcagarggag gaaaaggagg acgagaaaga gttgtaccct     1440
ttagcctccc tcaaatcact ctttgggaca gaccag                              1476
```

<210> SEQ ID NO 3
<211> LENGTH: 3021
<212> TYPE: DNA
<213> ORGANISM: Human immunodeficiency virus

<400> SEQUENCE: 3

```
tttttttaggg aagatctggc ctccgggggg caagaggcca ggcaactatg tacagaaaca      60
agtacaaccg acagccccac ctatggagga ggaggagatg actcagaaca agcagargga     120
ggaaaaggag gacgagaaag agttgtaccc tttagcctcc ctcaaatcac tctttgggac     180
agaccagtaa taccagtaaa aatagggggg catatttgtg aggctctatt agatacaggg     240
gctgatgaca cagtagtaga taacttacct ttagaaggaa gatggaaacc aaaaatgata     300
gggggaatag grggttttat aaaagtaaaa gaatttgaag aagttaagrt agaaatagaa     360
ggaagacaag tttatgggrac tgtattagtg ggyccaaccc cagtaaatat aataggaaga     420
aatattttga cattaattgg atgtactttg agtttcccca tcagccccat agaaatagta     480
ccagtaaaat taaagcagg aatggatggg cctagggtga agcaatggcc cttgtcaaag     540
gaaaaaatag aagctttaag agccatctgt caagagatgg aacaggaagg aaaaataaca     600
aaaattgggc ctgaaaatcc atataacacc cccattttg caataaaaaa gaaagatggc     660
agcaagtgga ggaaattagt agacttcaga gaactaaata aagaacaca gatttctgg      720 gaagtccaat tgggrratccc tcatccagga ggtcttcaga aagraaatc agtgaccata     780 ttagatgtag grgatgctta tttctcctgy cctttagatc cagattttag aaaatataca     840
gctttcacta tacctagtgt aaataatgac acaccaggac ttagrtatgt gtayaatgtt     900
```

```
ctgcctcagg gatggaaggg atcaccagcc attttycagc attcaatgac taagatctta      960
gaaccctta graagagtaa tccagaagta gaaatctayc aatacatgga tgatytatat      1020
gtagggtcag atytgccttt gtctgaacat agacagcggg tagagaaact yagggarcac    1080
ctctatgtat gggggttcac aactcctgac aaaaarcatc aaaaggagcc tcctttcctc    1140
tggatgggat atgagctcca tcctgacaag tggackgtgc aacccatcaa attaccagaa    1200
aaggaaagtt ggacagtaaa tgacattcag aagctagtag gaaagttaaa ttgggctagt    1260
caaatttatc caggaattag ggtaaaagag ttatgyaaac taattagagg aactaartcc    1320
ttaacagaag tagttgcytt tactagaaa gcagaattag aactgagga aaataaagaa      1380
attttaaaag aaccagtgca tggagtttat taccaaccag aaaaggaatt aatagtagac    1440
atacagaaac aggggcggg acaatggact tatcaggtat tccaggaaga acataaaaac    1500
ttgaaaacag ggaaatatgc caggcaaaag gctacccaca ccaatgatat aaggcaactg    1560
gcagargtaa tacagaaggt atcacaagaa agcatagtga tatggggaaa actacccaag    1620
tttagactac cagtaaatag aaatgtgtgg gagacttggt ggtcagacta ttggcaagcc    1680
acctggatac ctgagtggga atttgttagc caccccctc ttattaagct ctggtatcag    1740
ctagaaaaag accccatacc aggaacagaa acctttatg tagatggggc agcaaacaga    1800
gagaccaagt taggyaaagc tggatatgta acagataggg taggcagaa gataatcaaa    1860
ctagaagara caactaatca aaargcagaa ttagaagcag tgttgttagc cttaaaagaa    1920
tcaggagaac aggctaacat agtaacagac tcccaatatg tgttaggrat tatctcagca    1980
actccagatc aaagtgactc ccccytagtg caaaaaataa tagaagaaat gacaaaaaag    2040
gaaaaggtat acctrtcatg ggtaccagca cacaaaggca taggggtaa tgaraayata    2100
gayaaattag tcagyaarga cattagaaga gtgttattct tggaaggcat agaccaagca    2160
caggaggatc atgaaaaata tcacagtaat tggagagccc tagctagtga rtttggcctt    2220
ccaccaatag tggcaaaaga gattatyaac aattgcccta atgtcatgt aaaagggaa    2280
gccatgcatg gacaggtaga ctgcagtcca ggaatttggc aactggactg tacccacatg    2340
garggaaaaa ttatcctcgt ggcagtccat gtrgccagtg gcttcatgga agcagaagta    2400
attccagtag aaacaggaca agaagctgca tactttgtgc tcaaattggc atcaagatgg    2460
cctgtaaaag taatacacac agacaatggg cctaacttta ctagcgctgc agtaaaagca    2520
gcctgttggt ggcttaatat aactcatgag tttgggatac cctacaatcc ccaaagtcag    2580
ggagtagtgg aatcaatgaa taaagaatta agaaaatta tacatcaggt acgagatcaa    2640
gctgagcact taaagacagc agttcaaatg gcagtatttg tccacaattt taaaagaaaa    2700
gggggattg gggggtacac tgctggagac aggatcatag atattctggc tacacarata    2760
caaacaacag aattacaaaa acaaatttta aaattcaaa attttcaggt ctattacaga    2820
gacagcagag accctatttg gaaaggacca gcgacactcc tgtggaaagg tgaaggggca    2880
gtagtcatac aagacaaagg agatattaag gtagtcccta ggagaaaagc aaaaataatt    2940
agaaattatg gaaaacagat ggcaggtgat gattgtgtgg cagatacca gagagaaagt    3000
gaaagcctgg aacagtctgg t                                             3021
```

<210> SEQ ID NO 4
<211> LENGTH: 585
<212> TYPE: DNA
<213> ORGANISM: Human immunodeficiency virus

<400> SEQUENCE: 4

```
atggaaaaca gatggcaggt gatgattgtg tggcagatac ccagagagaa agtgaaagcc      60
tggaacagtc tggttaaata tcacaaatat aggtctaaaa agacaagaaa gtggttttat     120
aggcatcatt atgagacaac ccatcctagg attagttcag cagtttatat ccagtagga     180 acagcaacca ttattgtgac tacytattgg gggctcatgc ctggggaaag agaagaacaa     240
ttaggacatg gagcaagtgt ggagtggaga caaggtaaat acaccacaca gatagatcca     300
gaaacagcag ataggctaat tcatctccac tactttcaat gtttttcaga ttcggctgtg     360
aggagggcaa tactagggga cagggtattg aayamatgtg aatactcagc aggacatagt     420
caggtaggct ccttgcagta tttagcctta aaagtggtag tagggaaggt aaaraggaag     480
ccacccctcc ctagtgtcca gatattgaca caagacatat ggagcaaccc ccagaggacc     540
aagggccrcc aagagagcca ttcaatgagt ggatgctaca aacct                    585
```

<210> SEQ ID NO 5
<211> LENGTH: 294
<212> TYPE: DNA
<213> ORGANISM: Human immunodeficiency virus

<400> SEQUENCE: 5

```
atggagcaac ccccagagga ccaagggccr ccaagagagc cattcaatga gtggatgcta      60
caaaccttag aggaactcaa ggaggaagca gtaagacact cccctaggcc ttggttacac     120
tcattaggac agtatatcta ataccttat ggggacacct gggagggagt aactgcaatt     180
attaggatcc tacaacaatt aatytttatc cattatagaa ttggatgcca acatagtaga     240
ataggtatct tgacaccctc tcgaagagga aggagacatg gacccagtag atcc           294
```

<210> SEQ ID NO 6
<211> LENGTH: 213
<212> TYPE: DNA
<213> ORGANISM: Human immunodeficiency virus

<400> SEQUENCE: 6

```
atggacccag tagatcctga tctgcctcca tggcaacagc cagggagtca gccctcaagc      60
ccatgtaaca attgctactg caaagcctgc tgctatcatt gctatgtttg tttcacaaag     120
aagggtttgg gaatctccta tggcaggaag aagcgacgaa gacctgcgag agctgataac     180
aacaatcaga atcatcaaga tcctgtatca aag                                 213
```

<210> SEQ ID NO 7
<211> LENGTH: 306
<212> TYPE: DNA
<213> ORGANISM: Human immunodeficiency virus

<400> SEQUENCE: 7

```
atggcaggaa gaagcgacga agacctgcga gagctgataa caacaatcag aatcatcaag      60
atcctgtatc aaagtaaccc ttcgcctgca cgggggccca gcaggaatag caccaggaac     120
agacgaagaa ggtggagaag caggcaacgg cagatcgatc agattgctgg aaggattatt     180
gcctctcatc tgggacgacc tgaggaactt ggtggtgcag atctaccaga tattagtcag     240
ctgcatattg aggatcaagg acctcctgac aattctgtgg atacacctgg gccaactact     300
gaacag                                                               306
```

```
<210> SEQ ID NO 8
<211> LENGTH: 234
<212> TYPE: DNA
<213> ORGANISM: Human immunodeficiency virus

<400> SEQUENCE: 8
atgcatccta gggatgaggc agtattaata atagctgggg tgttattact ttgctgtata      60
gtagyttggg ggaaggtcct yctattagtg ctaaaagaaa gagaaagrga taagtttgtr     120
caaaggctag caaggtggag agaagggcaa gaagatgagg gtatgaaag taatgaagaa      180 gaagaagaac agcttaggga acttggaaat ctgcttggct ttgatcatgt actt           234

<210> SEQ ID NO 9
<211> LENGTH: 2664
<212> TYPE: DNA
<213> ORGANISM: Human immunodeficiency virus

<400> SEQUENCE: 9 atgagggta tgaaagtaat gaagaagaag aagaacagct tagggaactt ggaaatctgc       60
ttggctttga tcatgtactt taatgctatt agctatacta gtggaacacg ttatgttact     120
gtatattatg gggttccagt ttggagagat gctaaaatta ccttattctg tgcagcagat     180
gcatcgctaa ctagcarwga gcagcataat atttgggcca cccaggcctg tgtgcccaca     240
gaccctagac aatagaggt caggatagat aatgtaacag agtctttaa tatttgggac       300 aattatatgg tgacacaaat gcaggaagac atcattagct tatgggatca gagccttaaa     360
ccttgtgtaa aattgacagt tctatgtgtt actatgratt gtagcgactg cagcacggtt     420
gactgtacta ataactcctc cagggttaat aacagcaccg acagcaccaa caccagcaaa     480
accaatccat tagaattatt tcagtgcagt tttaatacaa ccacaatagt aaaagataaa     540
cagcagacac agcaagcact ctttatatag gcagacctaa caaaattgga taatgacaat     600
agtacatata gattaattaa ttgcaacacc actaccatta cacaggcatg cccaaaagtg     660
aactttgagc cgctacccat acagtattgt gcaccagcag ggtatgcact aatgaaatgc     720
aatcagacag gatttaatgg tacaggacct tgtaataaga cagttataac acactgtaca     780
catggaatta agccaacagt gtcaacacaa ttaatactca atggaactct agcaaaggga     840
gagcccttag taattactca gaatgtgtca gatacaggaa aagtcatcat agtaaaatta     900
aatgagagtg tgtcactcac ctgtataaga ccaggtaata acacaagagg acaagtgcaa     960
ctaggagtca tgacatggta taatatgaaa cactacgtag gcgatatcag ggcagctcat    1020
tgtaatgttt ctagggaaaa ttggaaaaga accttagaat gggtcagtga ggccatctgg    1080
aaggcttatc ctcaacattc caaccataca tccaaacaca accatacatt tgttttaaa    1140 aacagtacag ggggagaccc agaggttct tcgctgcact tcagttgtca tggggaattc     1200
ttttattgta acaccagcag cctgtttaac tttagttata cttggaatga caccacctgg    1260
cgggctgcag caatcataa tacaagtgaa aatataacac tgtcttgtag actgaagcaa    1320
gtagttaatt catggatgag agtgggatca ggcttgtttg cgacacctat tgaggggaa     1380 ttaaagtgtc aatccaacat tacaggtta atgttagaaa gagaactacc ttacaatgac    1440
agcagcaaga acaccacttt aagtcctata gggggagaca tgacaaatat ctggagaagt    1500
gagttatatc cctacaaagt agttcaagta aaagctctgg ccgtggcacc tacaaaaatt    1560
tccagaccta caattatggc tcatgatgga cataggaaga aagggcagc aggcctagga      1620 atgctattcc ttgggtttct gagcgcagca ggaagcacta tgggcgcagc gggaatcacg    1680
```

-continued

```
ctgacggtac aggccaagca attattgcat ggtatagtgc agcagcagaa caatatgcta    1740
agagctatag aggcacagca agaattgctg agactctctg tgtggggcat aagacagctc    1800
cgagctcgcc tgcttgccat tgaaacctat ttaagggatc agcaactcct aggactgtgg    1860
ggatgctcag gacaaatart atgttatact aatgtgccat ggaatagtac ctggaccaac    1920
aaaaatgaaa cagaattaga tggcatttgg ggtaatctaa catggcagga gtgggacaaa    1980
ctggtggata attcactga cacaatttac ttggaaatac agaaagcaca agagcagcag    2040
aaggaaaatg aaagaaagct attagaatta gacaaatggg cacaattgtg gagctggatg    2100
gacataacaa aatggttgtg gtacataaaa attttcatta tgatagtagg aggaattata    2160
ggactaaaaa tcttaatggc tataggtaat gtagtcagga aagtcaggca gggatartca    2220
cctgtrtcgt tgcagaccct tcgcctgcac gggggcccag caggaatagc accaggaaca    2280
gacgaagaag gtggagaagc aggcaacggc agatcgatca gattgctgga aggattattg    2340
cctctcatct gggacgacct gaggaacttg gtggtgcaga tctaccagat attagtcagc    2400
tgcatattga ggatcaagga cctcctgaca attctgtgga tacacctggg ccaactactg    2460
aacagtaact gcctgcgaga ctgctttgct gcgtgtggct attggactca agaattaaaa    2520
caragtgcaa ccagcytgtt gaacactgtt gctatatcag ttgcaaattg gactgatcaa    2580
gtaatagcag tagggcaaca aataggaaga ggcttcttga acataccaag aaggttaaga    2640
caagggctag aaagaagctt actg                                           2664
```

<210> SEQ ID NO 10
<211> LENGTH: 651
<212> TYPE: DNA
<213> ORGANISM: Human immunodeficiency virus

<400> SEQUENCE: 10

```
atggggaatg catggaagaa agtagctta gtgggctggc cagcagtcag ggaaaaaata      60
aagcagacta ccccgactac ccctgacccg actaccccag taacacctgc acccggggtt    120
ggggaaattt ccaaagaatt agcacaagga aaggaatac ccagtaaatt tagttcaaag     180
aacaatgcag cattggcctt cttggatgct catgaggaag aagaagtagg rttcccagtc    240
aggcctcaag tacccttaag atgcatgaca tacaaggcag catttgacct cagcttcttt    300
ttaaaagaaa agggaggact ggatgggtta gtttactcac tgagagagc agagatccta    360 gatctctgga tctatcacac tcagggattc ttccctgact ggcagaatta cactccaggg    420
ccaggagaaa gatatcccct gacctttggg tggctgttta actagtacc agtctctgag    480 gtagaagctg aggaaatggg agataagcag gagaaagcta agctgctaca tccagcctgc    540
acttatgggt tttcagatcc tcataaggag atcctagtgt ggaagtttga cagctcactt    600
ggaagagaac atgttgcctt acaaaagcac ccggaactgt ttattaaaga c             651
```

<210> SEQ ID NO 11
<211> LENGTH: 492
<212> TYPE: PRT
<213> ORGANISM: Human immunodeficiency virus
<220> FEATURE:
<221> NAME/KEY: MOD_RES
<222> LOCATION: (469)..(469)
<223> OTHER INFORMATION: Lys or Arg

<400> SEQUENCE: 11

```
Met Gly Ala Arg Ala Ser Val Leu Thr Gly Gly Arg Leu Asp Ala Trp
1               5                   10                  15

Glu Arg Ile Arg Leu Arg Pro Gly Gly Lys Lys Tyr Lys Leu Lys
            20                  25                  30

His Val Val Trp Ala Ser Arg Glu Leu Glu Arg Phe Ala Cys Asn Pro
            35                  40                  45

Gly Leu Met Glu Thr Ala Glu Gly Cys Glu Lys Leu Leu Glu Gln Leu
        50                  55                  60

Glu Pro Ala Leu Arg Thr Gly Ser Asp Gly Leu Gln Ser Leu Trp Asn
65                  70                  75                  80

Thr Leu Val Val Leu Trp Cys Val His Lys Arg Ile Glu Ile Ser Asp
                85                  90                  95

Thr Gln Gln Ala Ile Thr Lys Trp Lys Glu Glu Met Gln Lys Arg Lys
            100                 105                 110

Lys Thr Ser Glu Gly Ser Thr Gly Thr Ser Gln Asn Tyr Pro Ile Val
            115                 120                 125

Gln Asn Ala Gln Gly Gln Met Thr His Met Pro Leu Ser Pro Arg Thr
        130                 135                 140

Leu Asn Ala Trp Val Lys Ala Val Glu Glu Lys Ala Phe Asn Pro Glu
145                 150                 155                 160

Ile Ile Pro Met Phe Met Ala Leu Ser Glu Gly Ala Ile Pro Asp Asp
                165                 170                 175

Ile Asn Thr Met Leu Asn Ala Val Gly Gly His Gln Gly Ala Leu Gln
            180                 185                 190

Val Leu Lys Glu Val Ile Asn Glu Glu Ala Ala Glu Trp Asp Arg Thr
        195                 200                 205

His Pro Val Pro Val Gly Pro Leu Pro Pro Gly Gln Leu Arg Glu Pro
210                 215                 220

Thr Gly Gly Asp Ile Ala Gly Thr Thr Ser Thr Lys Gln Glu Gln Ile
225                 230                 235                 240

Thr Trp Met Thr Arg Asn Asn Pro Val Pro Val Gly Asp Ile Tyr Arg
                245                 250                 255

Lys Trp Ile Val Leu Gly Leu Asn Lys Val Val Lys Met Tyr Cys Pro
            260                 265                 270

Val Ser Ile Leu Asp Ile Lys Gln Gly Pro Lys Glu Pro Phe Arg Asp
        275                 280                 285

Tyr Val Asp Arg Phe Tyr Lys Thr Leu Arg Ala Glu Gln Ala Ser Gln
        290                 295                 300

Glu Val Lys Ser Trp Met Thr Asp Thr Leu Leu Val Gln Asn Ala Asn
305                 310                 315                 320

Pro Asp Cys Lys Gln Ile Leu Lys Ala Leu Gly Pro Gly Ala Thr Leu
                325                 330                 335

Glu Glu Met Met Asn Ala Cys Gln Gly Val Gly Gly Pro Thr His Lys
            340                 345                 350

Ala Arg Val Leu Ala Glu Ala Met Ala Ala Asn Gln Ala Ser Gln
        355                 360                 365

Glu Leu Lys Gly Gly Tyr Thr Thr Val Phe Met Gln Ser Gly Gln Arg
370                 375                 380

Lys Pro Val Lys Cys Phe Asn Cys Gly Lys Val Gly His Ile Ala Lys
385                 390                 395                 400

Asn Cys Lys Ala Pro Arg Arg Gly Cys Trp Lys Cys Gly Gln Glu
            405                 410                 415
```

```
Gly His Gln Met Lys Asp Cys Lys Ser Gly Arg Gln Ala Asn Phe Leu
            420                 425                 430

Gly Lys Ile Trp Pro Pro Gly Lys Arg Pro Gly Asn Tyr Val Gln
        435                 440                 445

Lys Gln Val Gln Pro Thr Ala Pro Pro Met Glu Glu Glu Met Thr
450                 455                 460

Gln Asn Lys Gln Xaa Glu Gln Lys Glu Asp Glu Lys Glu Leu Tyr Pro
465                 470                 475                 480

Leu Ala Ser Leu Lys Ser Leu Phe Gly Thr Asp Gln
                485                 490

<210> SEQ ID NO 12
<211> LENGTH: 1007
<212> TYPE: PRT
<213> ORGANISM: Human immunodeficiency virus
<220> FEATURE:
<221> NAME/KEY: MOD_RES
<222> LOCATION: (117)..(117)
<223> OTHER INFORMATION: Ile or Val

<400> SEQUENCE: 12

Phe Phe Arg Glu Asp Leu Ala Ser Gly Gly Gln Glu Ala Arg Gln Leu
1               5                   10                  15

Cys Thr Glu Thr Ser Thr Thr Asp Ser Pro Thr Tyr Gly Gly Gly
            20                  25                  30

Asp Asp Ser Glu Gln Ala Glu Gly Gly Lys Gly Arg Glu Arg Val
        35                  40                  45

Val Pro Phe Ser Leu Pro Gln Ile Thr Leu Trp Asp Arg Pro Val Ile
50                  55                  60

Pro Val Lys Ile Gly Gly His Ile Cys Glu Ala Leu Leu Asp Thr Gly
65                  70                  75                  80

Ala Asp Asp Thr Val Val Asp Asn Leu Pro Leu Glu Gly Arg Trp Lys
                85                  90                  95

Pro Lys Met Ile Gly Gly Ile Gly Gly Phe Ile Lys Val Lys Glu Phe
            100                 105                 110

Glu Glu Val Lys Xaa Glu Ile Glu Gly Arg Gln Val Tyr Gly Thr Val
        115                 120                 125

Leu Val Gly Pro Thr Pro Val Asn Ile Ile Gly Arg Asn Ile Leu Thr
130                 135                 140

Leu Ile Gly Cys Thr Leu Ser Phe Pro Ile Ser Pro Ile Glu Ile Val
145                 150                 155                 160

Pro Val Lys Leu Lys Ala Gly Met Asp Gly Pro Arg Val Lys Gln Trp
                165                 170                 175

Pro Leu Ser Lys Glu Lys Ile Glu Ala Leu Arg Ala Ile Cys Gln Glu
            180                 185                 190

Met Glu Gln Glu Gly Lys Ile Thr Lys Ile Gly Pro Glu Asn Pro Tyr
        195                 200                 205

Asn Thr Pro Ile Phe Ala Ile Lys Lys Lys Asp Gly Ser Lys Trp Arg
210                 215                 220

Lys Leu Val Asp Phe Arg Glu Leu Asn Lys Arg Thr Gln Asp Phe Trp
225                 230                 235                 240

Glu Val Gln Leu Gly Ile Pro His Pro Gly Gly Leu Gln Lys Arg Lys
                245                 250                 255

Ser Val Thr Ile Leu Asp Val Gly Asp Ala Tyr Phe Ser Cys Pro Leu
            260                 265                 270
```

```
Asp Pro Asp Phe Arg Lys Tyr Thr Ala Phe Thr Ile Pro Ser Val Asn
            275                 280                 285

Asn Asp Thr Pro Gly Leu Arg Tyr Val Tyr Asn Val Leu Pro Gln Gly
        290                 295                 300

Trp Lys Gly Ser Pro Ala Ile Phe Gln His Ser Met Thr Lys Ile Leu
305                 310                 315                 320

Glu Pro Phe Arg Lys Ser Asn Pro Glu Val Glu Ile Tyr Gln Tyr Met
                325                 330                 335

Asp Asp Leu Tyr Val Gly Ser Asp Leu Pro Leu Ser Glu His Arg Gln
            340                 345                 350

Arg Val Glu Lys Leu Arg Glu His Leu Tyr Val Trp Gly Phe Thr Thr
        355                 360                 365

Pro Asp Lys Lys His Gln Lys Glu Pro Pro Phe Leu Trp Met Gly Tyr
    370                 375                 380

Glu Leu His Pro Asp Lys Trp Thr Val Gln Pro Ile Lys Leu Pro Glu
385                 390                 395                 400

Lys Glu Ser Trp Thr Val Asn Asp Ile Gln Lys Leu Val Gly Lys Leu
                405                 410                 415

Asn Trp Ala Ser Gln Ile Tyr Pro Gly Ile Arg Val Lys Glu Leu Cys
            420                 425                 430

Lys Leu Ile Arg Gly Thr Lys Ser Leu Thr Glu Val Val Ala Phe Thr
        435                 440                 445

Arg Glu Ala Glu Leu Glu Leu Glu Glu Asn Lys Glu Ile Leu Lys Glu
    450                 455                 460

Pro Val His Gly Val Tyr Tyr Gln Pro Glu Lys Glu Leu Ile Val Asp
465                 470                 475                 480

Ile Gln Lys Gln Gly Ala Gly Gln Trp Thr Tyr Gln Val Phe Gln Glu
                485                 490                 495

Glu His Lys Asn Leu Lys Thr Gly Lys Tyr Ala Arg Gln Lys Ala Thr
            500                 505                 510

His Thr Asn Asp Ile Arg Gln Leu Ala Glu Val Ile Gln Lys Val Ser
        515                 520                 525

Gln Glu Ser Ile Val Ile Trp Gly Lys Leu Pro Lys Phe Arg Leu Pro
    530                 535                 540

Val Asn Arg Asn Val Trp Glu Thr Trp Trp Ser Asp Tyr Trp Gln Ala
545                 550                 555                 560

Thr Trp Ile Pro Glu Trp Glu Phe Val Ser Thr Pro Pro Leu Ile Lys
                565                 570                 575

Leu Trp Tyr Gln Leu Glu Lys Asp Pro Ile Pro Gly Thr Glu Thr Phe
            580                 585                 590

Tyr Val Asp Gly Ala Ala Asn Arg Glu Thr Lys Leu Gly Lys Ala Gly
        595                 600                 605

Tyr Val Thr Asp Arg Gly Arg Gln Lys Ile Ile Lys Leu Glu Glu Thr
    610                 615                 620

Thr Asn Gln Lys Ala Glu Leu Glu Ala Val Leu Leu Ala Leu Lys Glu
625                 630                 635                 640

Ser Gly Glu Gln Ala Asn Ile Val Thr Asp Ser Gln Tyr Val Leu Gly
                645                 650                 655

Ile Ile Ser Ala Thr Pro Asp Gln Ser Asp Ser Pro Leu Val Gln Lys
            660                 665                 670

Ile Ile Glu Glu Met Thr Lys Lys Glu Lys Val Tyr Leu Ser Trp Val
        675                 680                 685
```

```
Pro Ala His Lys Gly Ile Gly Gly Asn Glu Asn Ile Asp Lys Leu Val
        690                 695                 700
Ser Lys Asp Ile Arg Arg Val Leu Phe Leu Glu Gly Ile Asp Gln Ala
705                 710                 715                 720
Gln Glu Asp His Glu Lys Tyr His Ser Asn Trp Arg Ala Leu Ala Ser
                725                 730                 735
Glu Phe Gly Leu Pro Pro Ile Val Ala Lys Glu Ile Ile Asn Asn Cys
            740                 745                 750
Pro Lys Cys His Val Lys Gly Glu Ala Met His Gly Gln Val Asp Cys
        755                 760                 765
Ser Pro Gly Ile Trp Gln Leu Asp Cys Thr His Met Glu Gly Lys Ile
770                 775                 780
Ile Leu Val Ala Val His Val Ala Ser Gly Phe Met Glu Ala Glu Val
785                 790                 795                 800
Ile Pro Val Glu Thr Gly Gln Glu Ala Ala Tyr Phe Val Leu Lys Leu
                805                 810                 815
Ala Ser Arg Trp Pro Val Lys Val Ile His Thr Asp Asn Gly Pro Asn
            820                 825                 830
Phe Thr Ser Ala Ala Val Lys Ala Ala Cys Trp Trp Leu Asn Ile Thr
        835                 840                 845
His Glu Phe Gly Ile Pro Tyr Asn Pro Gln Ser Gln Gly Val Val Glu
850                 855                 860
Ser Met Asn Lys Glu Leu Lys Lys Ile Ile His Gln Val Arg Asp Gln
865                 870                 875                 880
Ala Glu His Leu Lys Thr Ala Val Gln Met Ala Val Phe Val His Asn
                885                 890                 895
Phe Lys Arg Lys Gly Gly Ile Gly Gly Tyr Thr Ala Gly Asp Arg Ile
            900                 905                 910
Ile Asp Ile Leu Ala Thr Gln Ile Gln Thr Thr Glu Leu Gln Lys Gln
        915                 920                 925
Ile Leu Lys Ile Gln Asn Phe Gln Val Tyr Tyr Arg Asp Ser Arg Asp
930                 935                 940
Pro Ile Trp Lys Gly Pro Ala Thr Leu Leu Trp Lys Gly Glu Gly Ala
945                 950                 955                 960
Val Val Ile Gln Asp Lys Gly Asp Ile Lys Val Val Pro Arg Arg Lys
                965                 970                 975
Ala Lys Ile Ile Arg Asn Tyr Gly Lys Gln Met Ala Gly Asp Asp Cys
            980                 985                 990
Val Ala Asp Thr Gln Arg Glu Ser  Glu Ser Leu Glu Gln  Ser Gly
        995                 1000                1005

<210> SEQ ID NO 13
<211> LENGTH: 195
<212> TYPE: PRT
<213> ORGANISM: Human immunodeficiency virus
<220> FEATURE:
<221> NAME/KEY: MOD_RES
<222> LOCATION: (132)..(132)
<223> OTHER INFORMATION: Thr or Lys
<220> FEATURE:
<221> NAME/KEY: MOD_RES
<222> LOCATION: (183)..(183)
<223> OTHER INFORMATION: His or Arg
```

```
<400> SEQUENCE: 13

Met Glu Asn Arg Trp Gln Val Met Ile Val Trp Gln Ile Pro Arg Glu
1               5                   10                  15

Lys Val Lys Ala Trp Asn Ser Leu Val Lys Tyr His Lys Tyr Arg Ser
            20                  25                  30

Lys Lys Thr Arg Lys Trp Phe Tyr Arg His His Tyr Glu Thr Thr His
        35                  40                  45

Pro Arg Ile Ser Ser Ala Val Tyr Ile Pro Val Gly Thr Ala Thr Ile
    50                  55                  60

Ile Val Thr Thr Tyr Trp Gly Leu Met Pro Gly Glu Arg Glu Gln
65                  70                  75                  80

Leu Gly His Gly Ala Ser Val Glu Trp Arg Gln Gly Lys Tyr Thr Thr
                85                  90                  95

Gln Ile Asp Pro Glu Thr Ala Asp Arg Leu Ile His Leu His Tyr Phe
            100                 105                 110

Gln Cys Phe Ser Asp Ser Ala Val Arg Arg Ala Ile Leu Gly Asp Arg
        115                 120                 125

Val Leu Asn Xaa Cys Glu Tyr Ser Ala Gly His Ser Gln Val Gly Ser
    130                 135                 140

Leu Gln Tyr Leu Ala Leu Lys Val Val Gly Lys Val Lys Arg Lys
145                 150                 155                 160

Pro Pro Leu Pro Ser Val Gln Ile Leu Thr Gln Asp Ile Trp Ser Asn
                165                 170                 175

Pro Gln Arg Thr Lys Gly Xaa Gln Glu Ser His Ser Met Ser Gly Cys
            180                 185                 190

Tyr Lys Pro
        195

<210> SEQ ID NO 14
<211> LENGTH: 98
<212> TYPE: PRT
<213> ORGANISM: Human immunodeficiency virus

<400> SEQUENCE: 14

Met Glu Gln Pro Pro Glu Asp Gln Gly Pro Pro Arg Glu Pro Phe Asn
1               5                   10                  15

Glu Trp Met Leu Gln Thr Leu Glu Glu Leu Lys Glu Glu Ala Val Arg
            20                  25                  30

His Phe Pro Arg Pro Trp Leu His Ser Leu Gly Gln Tyr Ile Tyr Asn
        35                  40                  45

Thr Tyr Gly Asp Thr Trp Glu Gly Val Thr Ala Ile Ile Arg Ile Leu
    50                  55                  60

Gln Gln Leu Ile Phe Ile His Tyr Arg Ile Gly Cys Gln His Ser Arg
65                  70                  75                  80

Ile Gly Ile Leu Thr Pro Ser Arg Arg Gly Arg His Gly Pro Ser
                85                  90                  95

Arg Ser

<210> SEQ ID NO 15
<211> LENGTH: 71
<212> TYPE: PRT
<213> ORGANISM: Human immunodeficiency virus
```

```
<400> SEQUENCE: 15

Met Asp Pro Val Asp Pro Asp Leu Pro Pro Trp Gln Gln Pro Gly Ser
1               5                   10                  15

Gln Pro Ser Ser Pro Cys Asn Asn Cys Tyr Cys Lys Ala Cys Cys Tyr
            20                  25                  30

His Cys Tyr Val Cys Phe Thr Lys Lys Gly Leu Gly Ile Ser Tyr Gly
            35                  40                  45

Arg Lys Lys Arg Arg Arg Pro Ala Arg Ala Asp Asn Asn Asn Gln Asn
        50                  55                  60

His Gln Asp Pro Val Ser Lys
65                  70

<210> SEQ ID NO 16
<211> LENGTH: 102
<212> TYPE: PRT
<213> ORGANISM: Human immunodeficiency virus

<400> SEQUENCE: 16

Met Ala Gly Arg Ser Asp Glu Asp Leu Arg Glu Leu Ile Thr Thr Ile
1               5                   10                  15

Arg Ile Ile Lys Ile Leu Tyr Gln Ser Asn Pro Ser Pro Ala Arg Gly
            20                  25                  30

Pro Ser Arg Asn Ser Thr Arg Asn Arg Arg Arg Trp Arg Ser Arg
            35                  40                  45

Gln Arg Gln Ile Asp Gln Ile Ala Gly Arg Ile Ile Ala Ser His Leu
        50                  55                  60

Gly Arg Pro Glu Glu Leu Gly Gly Ala Asp Leu Pro Asp Ile Ser Gln
65                  70                  75                  80

Leu His Ile Glu Asp Gln Gly Pro Pro Asp Asn Ser Val Asp Thr Pro
                85                  90                  95

Gly Pro Thr Thr Glu Gln
            100

<210> SEQ ID NO 17
<211> LENGTH: 78
<212> TYPE: PRT
<213> ORGANISM: Human immunodeficiency virus
<220> FEATURE:
<221> NAME/KEY: MOD_RES
<222> LOCATION: (22)..(22)
<223> OTHER INFORMATION: Val or Ala

<400> SEQUENCE: 17

Met His Pro Arg Asp Glu Ala Val Leu Ile Ile Ala Gly Val Leu Leu
1               5                   10                  15

Leu Cys Cys Ile Val Xaa Trp Gly Lys Val Leu Leu Val Leu Leu Lys
            20                  25                  30

Glu Arg Glu Arg Asp Lys Phe Val Gln Arg Leu Ala Arg Trp Arg Glu
            35                  40                  45

Gly Gln Glu Asp Glu Gly Tyr Glu Ser Asn Glu Glu Glu Glu Gln
        50                  55                  60

Leu Arg Glu Leu Gly Asn Leu Leu Gly Phe Asp His Val Leu
65                  70                  75

<210> SEQ ID NO 18
<211> LENGTH: 888
<212> TYPE: PRT
<213> ORGANISM: Human immunodeficiency virus
```

```
<220> FEATURE:
<221> NAME/KEY: MOD_RES
<222> LOCATION: (66)..(66)
<223> OTHER INFORMATION: Ser, Arg, Asn or Lys
<220> FEATURE:
<221> NAME/KEY: MOD_RES
<222> LOCATION: (133)..(133)
<223> OTHER INFORMATION: Asp or Asn
<220> FEATURE:
<221> NAME/KEY: MOD_RES
<222> LOCATION: (627)..(627)
<223> OTHER INFORMATION: Ile or Val

<400> SEQUENCE: 18

Met Arg Gly Met Lys Val Met Lys Lys Lys Asn Ser Leu Gly Asn
1               5                   10                  15

Leu Glu Ile Cys Leu Ala Leu Ile Met Tyr Phe Asn Ala Ile Ser Tyr
            20                  25                  30

Thr Ser Gly Thr Arg Tyr Val Thr Val Tyr Tyr Gly Val Pro Val Trp
        35                  40                  45

Arg Asp Ala Lys Ile Thr Leu Phe Cys Ala Ala Asp Ala Ser Leu Thr
    50                  55                  60

Ser Xaa Glu Gln His Asn Ile Trp Ala Thr Gln Ala Cys Val Pro Thr
65                  70                  75                  80

Asp Pro Arg Pro Ile Glu Val Arg Ile Asp Asn Val Thr Glu Ser Phe
                85                  90                  95

Asn Ile Trp Asp Asn Tyr Met Val Thr Gln Met Gln Glu Asp Ile Ile
            100                 105                 110

Ser Leu Trp Asp Gln Ser Leu Lys Pro Cys Val Lys Leu Thr Val Leu
        115                 120                 125

Cys Val Thr Met Xaa Cys Ser Asp Cys Ser Thr Val Asp Cys Thr Asn
    130                 135                 140

Asn Ser Ser Arg Val Asn Asn Ser Thr Asp Ser Thr Asn Thr Ser Lys
145                 150                 155                 160

Thr Asn Pro Leu Glu Leu Phe Gln Cys Ser Phe Asn Thr Thr Thr Ile
                165                 170                 175

Val Lys Asp Lys Gln Gln Thr Gln Ala Leu Phe Tyr Arg Ala Asp
            180                 185                 190

Leu Thr Lys Leu Asp Asn Asp Asn Ser Thr Tyr Arg Leu Ile Asn Cys
        195                 200                 205

Asn Thr Thr Thr Ile Thr Gln Ala Cys Pro Lys Val Asn Phe Glu Pro
    210                 215                 220

Leu Pro Ile Gln Tyr Cys Ala Pro Ala Gly Tyr Ala Leu Met Lys Cys
225                 230                 235                 240

Asn Gln Thr Gly Phe Asn Gly Thr Gly Pro Cys Asn Lys Thr Val Ile
                245                 250                 255

Thr His Cys Thr His Gly Ile Lys Pro Thr Val Ser Thr Gln Leu Ile
            260                 265                 270

Leu Asn Gly Thr Leu Ala Lys Gly Glu Pro Leu Val Ile Thr Gln Asn
        275                 280                 285

Val Ser Asp Thr Gly Lys Val Ile Ile Val Lys Leu Asn Glu Ser Val
    290                 295                 300

Ser Leu Thr Cys Ile Arg Pro Gly Asn Asn Thr Arg Gly Gln Val Gln
305                 310                 315                 320

Leu Gly Val Met Thr Trp Tyr Asn Met Lys His Tyr Val Gly Asp Ile
                325                 330                 335
```

```
Arg Ala Ala His Cys Asn Val Ser Arg Glu Asn Trp Lys Arg Thr Leu
            340                 345                 350
Glu Trp Val Ser Glu Ala Ile Trp Lys Ala Tyr Pro Gln His Ser Asn
        355                 360                 365
His Thr Ser Lys His Asn His Thr Phe Val Phe Lys Asn Ser Thr Gly
    370                 375                 380
Gly Asp Pro Glu Val Ser Ser Leu His Phe Ser Cys His Gly Glu Phe
385                 390                 395                 400
Phe Tyr Cys Asn Thr Ser Ser Leu Phe Asn Phe Ser Tyr Thr Trp Asn
                405                 410                 415
Asp Thr Thr Trp Arg Ala Ala Gly Asn His Asn Thr Ser Glu Asn Ile
            420                 425                 430
Thr Leu Ser Cys Arg Leu Lys Gln Val Val Asn Ser Trp Met Arg Val
        435                 440                 445
Gly Ser Gly Leu Phe Ala Thr Pro Ile Glu Gly Glu Leu Lys Cys Gln
    450                 455                 460
Ser Asn Ile Thr Gly Leu Met Leu Glu Arg Glu Leu Pro Tyr Asn Asp
465                 470                 475                 480
Ser Ser Lys Asn Thr Thr Leu Ser Pro Ile Gly Gly Asp Met Thr Asn
                485                 490                 495
Ile Trp Arg Ser Glu Leu Tyr Pro Tyr Lys Val Val Gln Val Lys Ala
            500                 505                 510
Leu Ala Val Ala Pro Thr Lys Ile Ser Arg Pro Thr Ile Met Ala His
        515                 520                 525
Asp Gly His Arg Lys Lys Arg Ala Ala Gly Leu Gly Met Leu Phe Leu
    530                 535                 540
Gly Phe Leu Ser Ala Ala Gly Ser Thr Met Gly Ala Ala Gly Ile Thr
545                 550                 555                 560
Leu Thr Val Gln Ala Lys Gln Leu Leu His Gly Ile Val Gln Gln Gln
                565                 570                 575
Asn Asn Met Leu Arg Ala Ile Glu Ala Gln Gln Glu Leu Leu Arg Leu
            580                 585                 590
Ser Val Trp Gly Ile Arg Gln Leu Arg Ala Arg Leu Leu Ala Ile Glu
        595                 600                 605
Thr Tyr Leu Arg Asp Gln Gln Leu Leu Gly Leu Trp Gly Cys Ser Gly
    610                 615                 620
Gln Ile Xaa Cys Tyr Thr Asn Val Pro Trp Asn Ser Thr Trp Thr Asn
625                 630                 635                 640
Lys Asn Glu Thr Glu Leu Asp Gly Ile Trp Gly Asn Leu Thr Trp Gln
                645                 650                 655
Glu Trp Asp Lys Leu Val Asp Asn Tyr Thr Asp Thr Ile Tyr Leu Glu
            660                 665                 670
Ile Gln Lys Ala Gln Glu Gln Gln Lys Glu Asn Glu Arg Lys Leu Leu
        675                 680                 685
Glu Leu Asp Lys Trp Ala Gln Leu Trp Ser Trp Met Asp Ile Thr Lys
    690                 695                 700
Trp Leu Trp Tyr Ile Lys Ile Phe Ile Met Ile Val Gly Gly Ile Ile
705                 710                 715                 720
Gly Leu Lys Ile Leu Met Ala Ile Gly Asn Val Val Arg Lys Val Arg
                725                 730                 735
Gln Gly Tyr Ser Pro Val Ser Leu Gln Thr Leu Arg Leu His Gly Gly
            740                 745                 750
```

-continued

```
Pro Ala Gly Ile Ala Pro Gly Thr Asp Glu Glu Gly Glu Ala Gly
            755                 760                 765

Asn Gly Arg Ser Ile Arg Leu Leu Glu Gly Leu Leu Pro Leu Ile Trp
        770                 775                 780

Asp Asp Leu Arg Asn Leu Val Val Gln Ile Tyr Gln Ile Leu Val Ser
785                 790                 795                 800

Cys Ile Leu Arg Ile Lys Asp Leu Leu Thr Ile Leu Trp Ile His Leu
            805                 810                 815

Gly Gln Leu Leu Asn Ser Asn Cys Leu Arg Asp Cys Phe Ala Ala Cys
            820                 825                 830

Gly Tyr Trp Thr Gln Glu Leu Lys Gln Ser Ala Thr Ser Leu Leu Asn
            835                 840                 845

Thr Val Ala Ile Ser Val Ala Asn Trp Thr Asp Gln Val Ile Ala Val
        850                 855                 860

Gly Gln Gln Ile Gly Arg Gly Phe Leu Asn Ile Pro Arg Arg Leu Arg
865                 870                 875                 880

Gln Gly Leu Glu Arg Ser Leu Leu
                885

<210> SEQ ID NO 19
<211> LENGTH: 34
<212> TYPE: PRT
<213> ORGANISM: Human immunodeficiency virus

<400> SEQUENCE: 19

Cys Ile Arg Pro Gly Asn Asn Thr Arg Gly Gln Val Gln Leu Gly Val
1               5                   10                  15

Met Thr Trp Tyr Asn Met Lys His Tyr Val Gly Asp Ile Arg Ala Ala
            20                  25                  30

His Cys

<210> SEQ ID NO 20
<211> LENGTH: 34
<212> TYPE: PRT
<213> ORGANISM: Human immunodeficiency virus

<400> SEQUENCE: 20

Cys Ile Arg Pro Gly Asn Asn Thr Arg Gly Gln Val Gln Leu Gly Ala
1               5                   10                  15

Ser Thr Trp Tyr Asn Met Lys His Tyr Val Gly Asp Ile Arg Ala Ala
            20                  25                  30

His Cys

<210> SEQ ID NO 21
<211> LENGTH: 34
<212> TYPE: PRT
<213> ORGANISM: Human immunodeficiency virus

<400> SEQUENCE: 21

Cys Ile Arg Pro Gly Asn Asn Thr Arg Gly Gln Val Gln Leu Gly Val
1               5                   10                  15

Met Thr Trp Tyr Asn Met Lys His Tyr Ile Gly Asp Ile Arg Ala Ala
            20                  25                  30

His Cys
```

```
<210> SEQ ID NO 22
<211> LENGTH: 129
<212> TYPE: PRT
<213> ORGANISM: Human immunodeficiency virus
<220> FEATURE:
<221> NAME/KEY: MOD_RES
<222> LOCATION: (63)..(63)
<223> OTHER INFORMATION: Val or Ile

<400> SEQUENCE: 22

Ala Lys Gln Leu Leu His Gly Ile Val Gln Gln Gln Asn Asn Met Leu
1               5                   10                  15

Arg Ala Ile Glu Ala Gln Gln Glu Leu Leu Arg Leu Ser Val Trp Gly
            20                  25                  30

Ile Arg Gln Leu Arg Ala Arg Leu Leu Ala Ile Glu Thr Tyr Leu Arg
        35                  40                  45

Asp Gln Gln Leu Leu Gly Leu Trp Gly Cys Ser Gly Gln Ile Xaa Cys
    50                  55                  60

Tyr Thr Asn Val Pro Trp Asn Ser Thr Trp Thr Asn Lys Asn Glu Thr
65                  70                  75                  80

Glu Leu Asp Gly Ile Trp Gly Asn Leu Thr Trp Gln Glu Trp Asp Lys
                85                  90                  95

Leu Val Asp Asn Tyr Thr Asp Thr Ile Tyr Leu Glu Ile Gln Lys Ala
            100                 105                 110

Gln Glu Gln Gln Lys Glu Asn Glu Arg Lys Leu Leu Glu Leu Asp Lys
        115                 120                 125

Trp

<210> SEQ ID NO 23
<211> LENGTH: 33
<212> TYPE: PRT
<213> ORGANISM: Human immunodeficiency virus
<220> FEATURE:
<221> NAME/KEY: MOD_RES
<222> LOCATION: (25)..(25)
<223> OTHER INFORMATION: Val or Ile

<400> SEQUENCE: 23

Arg Leu Leu Ala Ile Glu Thr Tyr Leu Arg Asp Gln Gln Leu Leu Gly
1               5                   10                  15

Leu Trp Gly Cys Ser Gly Gln Ile Xaa Cys Tyr Thr Asn Val Pro Trp
            20                  25                  30

Asn

<210> SEQ ID NO 24
<211> LENGTH: 25
<212> TYPE: PRT
<213> ORGANISM: Human immunodeficiency virus

<400> SEQUENCE: 24

Ile Tyr Leu Glu Ile Gln Lys Ala Gln Glu Gln Gln Lys Glu Asn Glu
1               5                   10                  15

Arg Lys Leu Leu Glu Leu Asp Lys Trp
            20                  25

<210> SEQ ID NO 25
<211> LENGTH: 217
<212> TYPE: PRT
<213> ORGANISM: Human immunodeficiency virus
```

<400> SEQUENCE: 25

Met Gly Asn Ala Trp Lys Lys Ser Ser Leu Val Gly Trp Pro Ala Val
1               5                   10                  15

Arg Glu Lys Ile Lys Gln Thr Thr Pro Thr Thr Pro Asp Pro Thr Thr
                20                  25                  30

Pro Val Thr Pro Ala Pro Gly Val Gly Glu Ile Ser Lys Glu Leu Ala
            35                  40                  45

Gln Gly Lys Gly Ile Pro Ser Lys Phe Ser Ser Lys Asn Asn Ala Ala
    50                  55                  60

Leu Ala Phe Leu Asp Ala His Glu Glu Glu Val Gly Phe Pro Val
65              70                  75                  80

Arg Pro Gln Val Pro Leu Arg Cys Met Thr Tyr Lys Ala Ala Phe Asp
                85                  90                  95

Leu Ser Phe Phe Leu Lys Glu Lys Gly Gly Leu Asp Gly Leu Val Tyr
            100                 105                 110

Ser Pro Glu Arg Ala Glu Ile Leu Asp Leu Trp Ile Tyr His Thr Gln
            115                 120                 125

Gly Phe Phe Pro Asp Trp Gln Asn Tyr Thr Pro Gly Pro Gly Glu Arg
130                 135                 140

Tyr Pro Leu Thr Phe Gly Trp Leu Phe Lys Leu Val Pro Val Ser Glu
145                 150                 155                 160

Val Glu Ala Glu Glu Met Gly Asp Lys Gln Lys Ala Lys Leu Leu
                165                 170                 175

His Pro Ala Cys Thr Tyr Gly Phe Ser Asp Pro His Lys Glu Ile Leu
            180                 185                 190

Val Trp Lys Phe Asp Ser Ser Leu Gly Arg Glu His Val Ala Leu Gln
            195                 200                 205

Lys His Pro Glu Leu Phe Ile Lys Asp
    210                 215

<210> SEQ ID NO 26
<211> LENGTH: 5
<212> TYPE: PRT
<213> ORGANISM: Human immunodeficiency virus

<400> SEQUENCE: 26

Gly Val Met Thr Trp
1               5

<210> SEQ ID NO 27
<211> LENGTH: 5
<212> TYPE: PRT
<213> ORGANISM: Human immunodeficiency virus

<400> SEQUENCE: 27

Gly Ala Ser Thr Trp
1               5

<210> SEQ ID NO 28
<211> LENGTH: 5
<212> TYPE: PRT
<213> ORGANISM: Human immunodeficiency virus

<400> SEQUENCE: 28

Gly Pro Met Thr Trp
1               5

<210> SEQ ID NO 29
<211> LENGTH: 5
<212> TYPE: PRT
<213> ORGANISM: Human immunodeficiency virus
<220> FEATURE:
<221> NAME/KEY: MOD_RES
<222> LOCATION: (3)..(3)
<223> OTHER INFORMATION: Met or Leu

<400> SEQUENCE: 29

Gly Pro Xaa Thr Ile
1               5

<210> SEQ ID NO 30
<211> LENGTH: 5
<212> TYPE: PRT
<213> ORGANISM: Human immunodeficiency virus

<400> SEQUENCE: 30

Gly Pro Gly Gln Ala
1               5

<210> SEQ ID NO 31
<211> LENGTH: 5
<212> TYPE: PRT
<213> ORGANISM: Human immunodeficiency virus

<400> SEQUENCE: 31

Gly Pro Ala Met Thr
1               5

<210> SEQ ID NO 32
<211> LENGTH: 5
<212> TYPE: PRT
<213> ORGANISM: Human immunodeficiency virus

<400> SEQUENCE: 32

Gly Pro Met Ala Trp
1               5

<210> SEQ ID NO 33
<211> LENGTH: 32
<212> TYPE: PRT
<213> ORGANISM: Human immunodeficiency virus

<400> SEQUENCE: 33

Arg Leu Leu Ala Ile Glu Thr Tyr Leu Arg Asp Gln Gln Leu Leu Gly
1               5                   10                  15

Leu Trp Gly Cys Ser Gly Gln Ile Val Cys Tyr Thr Asn Val Pro Trp
            20                  25                  30

<210> SEQ ID NO 34
<211> LENGTH: 21
<212> TYPE: PRT
<213> ORGANISM: Human immunodeficiency virus

<400> SEQUENCE: 34

Asn Thr Arg Gly Gln Val Gln Ile Gly Pro Met Thr Trp Tyr Asn Met
1               5                   10                  15

Lys Phe Tyr Thr Gly
            20

```
<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 35

His His His His His His
1               5

<210> SEQ ID NO 36
<211> LENGTH: 126
<212> TYPE: PRT
<213> ORGANISM: Human immunodeficiency virus

<400> SEQUENCE: 36

Ala Arg Gln Leu Leu Ser Gly Ile Val Gln Gln Asn Asn Leu Leu
1               5                   10                  15

Arg Ala Ile Glu Ala Gln Gln His Leu Leu Gln Leu Thr Val Trp Gly
            20                  25                  30

Ile Lys Gln Leu Gln Ala Arg Ile Leu Ala Val Glu Arg Tyr Leu Lys
        35                  40                  45

Asp Gln Gln Leu Leu Gly Ile Trp Gly Cys Ser Gly Lys Leu Ile Cys
    50                  55                  60

Thr Thr Ala Val Pro Trp Asn Ala Ser Trp Ser Asn Lys Ser Leu Glu
65                  70                  75                  80

Gln Ile Trp Asn His Thr Thr Trp Met Glu Trp Asp Arg Glu Ile Asn
                85                  90                  95

Asn Tyr Thr Ser Leu Ile His Ser Leu Ile Glu Glu Ser Gln Asn Gln
            100                 105                 110

Gln Glu Lys Asn Glu Gln Glu Leu Leu Glu Leu Asp Lys Trp
        115                 120                 125

<210> SEQ ID NO 37
<211> LENGTH: 127
<212> TYPE: PRT
<213> ORGANISM: Human immunodeficiency virus

<400> SEQUENCE: 37

Ala Arg Thr Leu Leu Ser Gly Ile Val Gln Gln Gln Asn Ile Leu Leu
1               5                   10                  15

Arg Ala Ile Glu Ala Gln Gln His Leu Leu Gln Leu Ser Ile Trp Gly
            20                  25                  30

Ile Lys Gln Leu Gln Ala Lys Val Leu Ala Ile Glu Arg Tyr Leu Arg
        35                  40                  45

Asp Gln Gln Ile Leu Ser Leu Trp Gly Cys Ser Gly Lys Thr Ile Cys
    50                  55                  60

Tyr Thr Thr Val Pro Trp Asn Glu Thr Trp Ser Asn Thr Ser Tyr
65                  70                  75                  80

Asp Thr Ile Trp Asn Asn Leu Thr Trp Gln Gln Trp Asp Glu Lys Val
                85                  90                  95

Arg Asn Tyr Ser Gly Val Ile Phe Gly Leu Ile Glu Gln Ala Gln Glu
            100                 105                 110

Gln Gln Asn Thr Asn Glu Lys Ser Leu Leu Glu Leu Asp Gln Trp
        115                 120                 125
```

```
<210> SEQ ID NO 38
<211> LENGTH: 124
<212> TYPE: PRT
<213> ORGANISM: Human immunodeficiency virus
<220> FEATURE:
<221> NAME/KEY: MOD_RES
<222> LOCATION: (30)..(30)
<223> OTHER INFORMATION: Any amino acid

<400> SEQUENCE: 38

Thr His Thr Leu Leu Lys Gly Ile Val Gln Gln Gln Asp Asn Leu Leu
1               5                   10                  15

Arg Ala Ile Gln Ala Gln Gln Gln Leu Leu Arg Leu Ser Xaa Trp Gly
            20                  25                  30

Ile Arg Gln Leu Arg Ala Arg Leu Leu Ala Leu Glu Thr Leu Leu Gln
        35                  40                  45

Asn Gln Gln Leu Leu Ser Leu Trp Gly Cys Lys Gly Lys Leu Val Cys
    50                  55                  60

Tyr Thr Ser Val Lys Trp Asn Arg Thr Trp Ile Gly Asn Glu Ser Ile
65                  70                  75                  80

Trp Asp Thr Leu Thr Trp Gln Glu Trp Asp Arg Gln Ile Ser Asn Ile
                85                  90                  95

Ser Ser Thr Ile Tyr Glu Glu Ile Gln Lys Ala Gln Val Gln Gln Glu
            100                 105                 110

Gln Asn Glu Lys Lys Leu Leu Glu Leu Asp Glu Trp
        115                 120

<210> SEQ ID NO 39
<211> LENGTH: 129
<212> TYPE: PRT
<213> ORGANISM: Human immunodeficiency virus
<220> FEATURE:
<221> NAME/KEY: MOD_RES
<222> LOCATION: (85)..(85)
<223> OTHER INFORMATION: Any amino acid

<400> SEQUENCE: 39

Ala Arg Gln Val Leu His Gly Ile Val Gln Gln Gln Asn Asn Met Leu
1               5                   10                  15

Arg Ala Ile Glu Ala Gln Gln Glu Leu Leu Arg Leu Ser Val Trp Gly
            20                  25                  30

Ile Arg Gln Leu Arg Ala Arg Leu Leu Ala Ile Glu Thr Tyr Leu Arg
        35                  40                  45

Asp Gln Gln Leu Leu Gly Leu Trp Gly Cys Ser Gly Lys Ile Val Cys
    50                  55                  60

Tyr Thr Asn Val Pro Trp Asn Arg Ser Trp Thr Asn Lys Ser Glu Thr
65                  70                  75                  80

Glu Leu Asp Gly Xaa Trp Thr Asn Leu Thr Trp Gln Glu Trp Asp Lys
                85                  90                  95

Leu Val Asp Asn Tyr Thr Asp Thr Ile Tyr Leu Glu Ile Gln Arg Ala
            100                 105                 110

Gln Asp Gln Gln Lys Ala Asn Glu Lys Lys Leu Leu Glu Leu Asp Gln
        115                 120                 125

Trp

<210> SEQ ID NO 40
<211> LENGTH: 9238
<212> TYPE: DNA
<213> ORGANISM: Human immunodeficiency virus
```

```
<400> SEQUENCE: 40
taaagcttgc cttgagtgag taaagcagtg tgtgctcatc tgttcagact ctggtatcta      60
gagatccctc agagcacttt tagccgagtg aaaaatctct agcagtggcg cccgaacagg     120
gacctgaaag tgaaaccagt ttctgaaacc tccgacgcac gggctcggct cagcggagtg     180
cacctgctga gaggcgagag gaactcacgg cggtgagtac attttgtcag tggtgactga     240
ccctagggga agaggcgaag tctctagggg aggagatggg tgcgagagcg tcagtgttga     300 caggggggccg attggatgca tgggaaagaa ttaggcttag accaggaggt aagaaaaaat     360
ataagctaaa acatgtagta tgggcaagca gagagctgga aagatttgca tgtaatcctg     420
ggcttatgga aacagcggaa ggctgcgaaa aattattaga gcagttagaa ccagctctca     480
gaacaggctc ygatggcctg cagtctcttt ggaacaccct agtagttyta tggtgtgttc     540
acaaaagaat agagataagt gacacacagc aggccattac aaaatggaag gaggaaatgc     600
agaaaagaaa gaaacatca gagggcagca ctgaacaag tcaaaactat cctatcgtgc      660
agaatgccca ggggcaaatg acccatatgc cgctgtcccc caggacgctg aatgcctggg     720
tgaaggcagt agaagaaaaa gccttcaacc ctgaaattat ccctatgttt atggccttgt     780 cagaagggggc tatacctgat gacatcaata ccatgcttaa tgcagtaggc ggacatcagg    840
gagcgttgca ggtgttgaaa gaggtaatta atgaagaggc tgcagaatgg gatagaacac     900 atccccgttcc agtaggacca ttaccaccag ggcagcttag agaaccaaca ggaggggata    960
ttgcaggaac cactagtacc aaacaggaac agataacctg gatgacaagg aacaatcctg    1020
taccagtagg ggacatctat agaaartgga tagtgttggg gctcaataaa gtggtaaaaa    1080
tgtactgccc cgttagcatt ctggacataa agcagggacc taaggaacca tttagagatt    1140
atgtagayag attctacaaa accctcgag cagagcaagc cagtcaggaa gtaaaaagtt     1200
ggatgacaga caccttacta gtacaaaatg ctaatccaga ttgyaagcag attttgaaag    1260
ctctgggacc aggtgccacc ttagaagaaa tgatgaatgc ctgtcaagga gtagggggac    1320
caacacataa ggccagggtc ttggcagaag ctatggcagc agctaatcaa gctagccaag    1380
aattaaaagg agggtataca acagttttta tgcagagtgg acagaaaag ccagttaagt     1440 gctttaactg tggaaaagta ggacacatag caaagaactg caaggcacct agaagaaggg    1500
grtgttggaa gtgtggacag gaaggtcatc aaatgaaaga ctgcaaatca ggaagacagg    1560 caaattttttt agggaagatc tggcctccgg ggggcaagag gccaggcaac tatgtacaga    1620
aacaagtaca accgacagcc ccacctatgg aggaggagga gatgactcag aacaagcaga    1680
rggaggaaaa ggaggacgag aaagagttgt acccctttagc ctccctcaaa tcactctttg    1740
ggacagacca gtaataccag taaaaatagg ggggcatatt tgtgaggctc tattagatac    1800
aggggctgat gacacagtag tagataactt acctttagaa ggaagatgga aaccaaaaat    1860 gatagggga ataggrggtt ttataaaagt aaaagaattt gaagaagtta agrtagaaat    1920
agaaggaaga caagtttatg gractgtatt agtggggycca accccagtaa atataatagg    1980
aagaaatatt ttgacattaa ttggatgtac tttgagtttc cccatcagcc ccatagaaat    2040
agtaccagta aaattaaaag caggaatgga tgggcctagg gtgaagcaat ggcccttgtc    2100
aaaggaaaaa atagaagctt taagagccat ctgtcaagag atggaacagg aaggaaaaat    2160
aacaaaaatt gggcctgaaa atccatataa caccccccatt tttgcaataa aaagaaaga    2220 tggcagcaag tggaggaaat tagtagactt cagagaacta aataaaagaa cacaagattt    2280
ctgggaagtc caattgggra tccctcatcc aggaggtctt cagaaaagra aatcagtgac    2340
```

```
catattagat gtaggrgatg cttatttctc ctgyccttta gatccagatt ttagaaaata    2400
tacagctttc actataccta gtgtaaataa tgacacacca ggacttagrt atgtgtayaa    2460
tgttctgcct cagggatgga agggatcacc agccattty cagcattcaa tgactaagat    2520
cttagaaccc tttagraaga gtaatccaga agtagaaatc taycaataca tggatgatyt    2580
atatgtaggg tcagatytgc ctttgtctga acatagacag cgggtagaga aactyaggga    2640
rcacctctat gtatgggggt tcacaactcc tgacaaaaar catcaaaagg agcctccttt    2700
cctctggatg ggatatgagc tccatcctga caagtggack gtgcaaccca tcaaattacc    2760
agaaaaggaa agttggacag taatgacat tcagaagcta gtaggaaagt taaattgggc    2820
tagtcaaatt tatccaggaa ttagggtaaa agagttatgy aaactaatta gaggaactaa    2880
rtccttaaca gaagtagttg cytttactag agaagcagaa ttagaactag aggaaaataa    2940 agaaattta aaagaaccag tgcatggagt ttattaccaa ccagaaaagg aattaatagt    3000
agacatacag aaacaggggg cgggacaatg gacttatcag gtattccagg aagaacataa    3060
aaacttgaaa acagggaaat atgccaggca aaaggctacc cacaccaatg atataaggca    3120
actggcagar gtaatacaga aggtatcaca agaaagcata gtgatatggg gaaaactacc    3180
caagtttaga ctaccagtaa atagaaatgt gtgggagact tggtggtcag actattggca    3240
agccacctgg atacctgagt gggaatttgt tagcacaccc cctcttatta agctctggta    3300
tcagctagaa aaagaccca taccaggaac agaaaccttt tatgtagatg gggcagcaaa    3360
cagagagacc aagttaggya aagctggata tgtaacagat aggggtaggc agaagataat    3420
caaactagaa garacaacta atcaaaargc agaattagaa gcagtgttgt tagccttaaa    3480
agaatcagga gaacaggcta acatagtaac agactcccaa tatgtgttag grattatctc    3540
agcaactcca gatcaaagtg actcccccyt agtgcaaaaa ataatagaag aaatgacaaa    3600
aaaggaaaag gtatacctrt catgggtacc agcacacaaa ggcataggg gtaatgaraa    3660 yatagayaaa ttagtcagya argacattag aagagtgtta ttcttggaag gcatagacca    3720
agcacaggag gatcatgaaa aatatcacag taattggaga gccctagcta gtgartttgg    3780
ccttccacca atagtggcaa aagagattat yaacaattgc cctaaatgtc atgtaaaagg    3840
ggaagccatg catggacagg tagactgcag tccaggaatt tggcaactgg actgtaccca    3900
catggargga aaaattatcc tcgtggcagt ccatgtrgcc agtggcttca tggaagcaga    3960
agtaattcca gtagaaacag gacaagaagc tgcatacttt gtgctcaaat ggcatcaag    4020 atggcctgta aaagtaatac acacagacaa tgggcctaac tttactagcg ctgcagtaaa    4080
agcagcctgt tggtggctta atataactca tgagtttggg atacctacaa atccccaaag    4140
tcagggagta gtggaatcaa tgaataaaga attaagaaaa attatacatc aggtacgaga    4200
tcaagctgag cacttaaaga cagcagttca aatggcagta tttgtccaca attttaaaag    4260 aaaaggggg attgggggt acactgctgg agacaggatc atagatattc tggctacaca    4320
ratacaaaca acagaattac aaaaacaaat tttaaaaatt caaaatttc aggtctatta    4380 cagagacagc agagaccta tttggaaagg accagcgaca ctcctgtgga aaggtgaagg    4440
ggcagtagtc atacaagaca aaggagatat taggtagtc cctaggagaa agcaaaaat    4500 aattagaaat tatggaaaac agatggcagg tgatgattgt gtgcagata cccagagaga    4560 aagtgaaagc ctggaacagt ctggttaaat atcacaaata taggtctaaa aagacaagaa    4620
agtggtttta taggcatcat tatgagacaa cccatcctag gattagttca gcagtttata    4680
ttccagtagg aacagcaacc attattgtga ctacytattg ggggctcatg cctggggaaa    4740
```

```
gagaagaaca attaggacat ggagcaagtg tggagtggag acaaggtaaa tacaccacac    4800
agatagatcc agaaacagca gataggctaa ttcatctcca ctactttcaa tgtttttcag    4860
attcggctgt gaggagggca atactagggg acagggtatt gaayamatgt gaatactcag    4920
caggacatag tcaggtaggc tccttgcagt atttagcctt aaaagtggta gtagggaagg    4980
taaaraggaa gccacccctc cctagtgtcc agatattgac acaagacata tggagcaacc    5040
cccagaggac caagggccrc caagagagcc attcaatgag tggatgctac aaaccttaga    5100
ggaactcaag gaggaagcag taagacactt ccctaggcct tggttacact cattaggaca    5160
gtatatctat aatacctatg gggacacctg ggagggagta actgcaatta ttaggatcct    5220
acaacaatta atytttatcc attatagaat tggatgccaa catagtagaa taggtatctt    5280
gacaccctct cgaagaggaa ggagacatgg acccagtaga tcctgatctg cctccatggc    5340
aacagccagg gagtcagccc tcaagcccat gtaacaattg ctactgcaaa gcctgctgct    5400
atcattgcta tgtttgtttc acaaagaagg gtttgggaat ctcctatggc aggaagaagc    5460
gacgaagacc tgcgagagct gataacaaca atcagaatca tcaagatcct gtatcaaagt    5520
agtaagtaga aataataagy tgtgttaatg catcctaggg atgaggcagt attaataata    5580
gctggggtgt tattactttg ctgtatagta gyttggggga aggtcctyct attagtgcta    5640
aaagaaagag aaagrgataa gtttgtrcaa aggctagcaa ggtggagaga agggcaagaa    5700
gatgaggggt atgaaagtaa tgaagaagaa gaagaacagc ttagggaact tggaaatctg    5760
cttggctttg atcatgtact ttaatgctat tagctatact agtggaacac gttatgttac    5820
tgtatattat ggggttccag tttgagagaa tgctaaaatt accttattct gtgcagcaga    5880
tgcatcgcta actagcarwg agcagcataa tatttgggcc acccaggcct gtgtgcccac    5940
agaccctaga ccaatagagg tcaggataga taatgtaaca gagtctttta atatttggga    6000
caattatatg gtgacacaaa tgcaggaaga catcattagc ttatgggatc agagccttaa    6060
accttgtgta aaattgacag ttctatgtgt tactatgrat tgtagcgact gcagcacggt    6120
tgactgtact aataactcct ccagggttaa taacagcacc gacagcacca acaccagcaa    6180
aaccaatcca ttagaattat ttcagtgcag ttttaataca accacaatag taaaagataa    6240
acagcagaca cagcaagcac tcttttatag agcagaccta acaaaattgg ataatgacaa    6300
tagtacatat agattaatta attgcaacac cactaccatt acacaggcat gcccaaaagt    6360
gaactttgag ccgctaccca tacagtattg tgcaccagca gggtatgcac taatgaaatg    6420
caatcagaca ggatttaatg gtacaggacc ttgtaataag acagttataa cacactgtac    6480
acatggaatt aagccaacag tgtcaacaca attaatactc aatggaactc tagcaaaggg    6540
agagccctta gtaattactc agaatgtgtc agatacagga aaagtcatca tagtaaaatt    6600
aaatgagagt gtgtcactca cctgtataag accaggtaat aacacaagag acaagtgca    6660 actaggagtc atgacatggt ataatatgaa acactacgta ggcgatatca ggcagctca    6720 ttgtaatgtt tctagggaaa attggaaaag aaccttagaa tgggtcagtg aggccatctg    6780
gaaggcttat cctcaacatt ccaaccatac atccaaacac aaccatacat tgttttttaa    6840
aaacagtaca gggggagacc cagaggtttc ttcgctgcac ttcagttgtc atggggaatt    6900 ctttattgt aacaccagca gcctgtttaa ctttagttat acttggaatg acaccacctg    6960
gcgggctgca ggcaatcata atacaagtga aaatataaca ctgtcttgta gactgaagca    7020
agtagttaat tcatgatga gagtgggatc aggcttgttt gcgacaccta ttgagggga    7080 attaaagtgt caatccaaca ttacaggttt aatgttagaa agagaactac cttacaatga    7140
```

-continued

```
cagcagcaag aacaccactt taagtcctat aggggagac  atgacaaata tctggagaag    7200
tgagttatat ccctacaaag tagttcaagt aaaagctctg gccgtggcac ctacaaaaat    7260
ttccagacct acaattatgg ctcatgatgg acataggaag aaaagggcag caggcctagg    7320
aatgctattc cttgggtttc tgagcgcagc aggaagcact atgggcgcag cgggaatcac    7380
gctgacggta caggccaagc aattattgca tggtatagtg cagcagcaga acaatatgct    7440
aagagctata gaggcacagc aagaattgct gagactctct gtgtgggca  taagacagct    7500
ccgagctcgc ctgcttgcca ttgaaaccta tttaagggat cagcaactcc taggactgtg    7560
gggatgctca ggacaaatar tatgttatac taatgtgcca tggaatagta cctggaccaa    7620
caaaaatgaa acagaattag atggcatttg ggtaatcta  acatggcagg agtgggacaa    7680
actggtggat aattacactg acacaattta cttggaaata cagaaagcac aagagcagca    7740
gaaggaaaat gaaagaaagc tattagaatt agacaaatgg gcacaattgt ggagctggat    7800
ggacataaca aaatggttgt ggtacataaa aattttcatt atgatagtag gaggaattat    7860
aggactaaaa atcttaatgg ctataggtaa tgtagtcagg aaagtcaggc agggataytc    7920
acctgtrtcg ttgcagaccc ttcgcctgca cggggcccca gcaggaatag caccaggaac    7980
agacgaagaa ggtggagaag caggcaacgg cagatcgatc agattgctgg aaggattatt    8040
gcctctcatc tgggacgacc tgaggaactt ggtggtgcag atctaccaga tattagtcag    8100
ctgcatattg aggatcaagg acctcctgac aattctgtgg atacacctgg ccaactact    8160
gaacagtaac tgcctgcgag actgctttgc tgcgtgtggc tattggactc aagaattaaa    8220
acaragtgca accagcytgt tgaacactgt tgctatatca gttgcaaatt ggactgatca    8280
agtaatagca gtagggcaac aaataggaag aggcttcttg aacataccaa gaaggttaag    8340
acaagggcta gaaagaagct tactgtaaaa tggggaatgc atggaagaaa agtagcttag    8400
tgggctggcc agcagtcagg gaaaaaataa agcagactac cccgactacc cctgacccga    8460
ctaccccagt aacacctgca cccggggttg gggaaatttc caagaattaa gcacaaggaa    8520
aaggaatacc cagtaaattt agttcaaaga acaatgcagc attggccttc ttggatgctc    8580
atgaggaaga agaagtaggr ttcccagtca ggcctcaagt acccttaaga tgcatgacat    8640
acaaggcagc atttgacctc agcttctttt taaaagaaaa gggaggactg gatgggttag    8700
tttactcacc tgagagagca gagatcctag atctctggat ctatcacact cagggattct    8760
tccctgactg gcagaattac actccagggc caggagaaag atatcccctg acctttgggt    8820
ggctgtttaa actagtacca gtctctgagg tagaagctga ggaaatggga gataagcagg    8880
agaaagctaa gctgctacat ccagcctgca cttatgggtt ttcagatcct cataaggaga    8940
tcctagtgtg gaagtttgac agctcacttg aagagaaca  tgttgcctta caaaagcacc    9000
cggaactgtt tattaaagac taaattgctg acgccacgta gctgctaaag ctgctgacac    9060
tgcagggact ttccggggac ggaaagtccc gagggcggaa caaggggagg agcaggggag    9120
tggtttcacc ctcagagctg catataagca gctgcttcac gcttgtactg ggtctctgtg    9180
acagaccaga ttagagcctg ggagctctct ggtctaagca gaacccactg gttaaaaa      9238
```

<210> SEQ ID NO 41
<211> LENGTH: 432
<212> TYPE: DNA
<213> ORGANISM: Human immunodeficiency virus

<400> SEQUENCE: 41

```
gaattccatg aaagccaagc aattattgca tggtatagtg cagcagcaga acaatatgct    60
aagagctata gaggcacagc aagaattgct gagactctct gtgtgggca taagacagct    120
ccgagctcgc ctgcttgcca ttgaaaccta tttaagggat cagcaactcc taggactgtg   180
gggatgctca ggacaaatag tatgttatac taatgtgcca tggaatagta cctggaccaa   240
caaaaatgaa acagaattag atggcatttg gggtaatcta acatggcagg agtgggacaa   300
actggtggat aattacactg acacaattta cttggaaata cagaaagcac aagagcagca   360
gaaggaaaat gaagaaagc tattagaatt agacaaatgg gagcaccacc accaccacca    420
ctaataggat cc                                                       432
```

<210> SEQ ID NO 42
<211> LENGTH: 432
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
gaattccatg aaagcaaaac agcttctgca tggtatcgtt cagcagcaga acaacatgct    60
gcgtgctatc gaagctcagc aggaactgct gcgtctgtct gtttggggta tccgtcagct   120
tcgtgctcgt ctgctggcta tcgaaaccta cctgcgtgac cagcagctgc tgggtctgtg   180
gggttgctct ggtcagatcg tttgctacac taacgttccg tggaactcta cttggactaa   240
caaaaacgaa actgaactgg acggtatctg gggtaacctg acttggcagg aatgggacaa   300
actggtggac aactacacag acacaatcta cttggaaatc caaaaagcac aggaacagca   360
gaaagaaaac gaacgtaaac ttctcgaact ggacaaatgg gagcaccacc accaccacca   420
ctaataggat cc                                                       432
```

<210> SEQ ID NO 43
<211> LENGTH: 138
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Met Lys Ala Lys Gln Leu Leu His Gly Ile Val Gln Gln Asn Asn
1               5                   10                  15

Met Leu Arg Ala Ile Glu Ala Gln Gln Glu Leu Leu Arg Leu Ser Val
                20                  25                  30

Trp Gly Ile Arg Gln Leu Arg Ala Arg Leu Leu Ala Ile Glu Thr Tyr
            35                  40                  45

Leu Arg Asp Gln Gln Leu Leu Gly Leu Trp Gly Cys Ser Gly Gln Ile
        50                  55                  60

Val Cys Tyr Thr Asn Val Pro Trp Asn Ser Thr Trp Thr Asn Lys Asn
65                  70                  75                  80

Glu Thr Glu Leu Asp Gly Ile Trp Gly Asn Leu Thr Trp Gln Glu Trp
                85                  90                  95

Asp Lys Leu Val Asp Asn Tyr Thr Asp Thr Ile Tyr Leu Glu Ile Gln
                100                 105                 110
```

-continued

```
Lys Ala Gln Glu Gln Gln Lys Glu Asn Glu Arg Lys Leu Leu Glu Leu
        115                 120                 125

Asp Lys Trp Glu His His His His His His
    130                 135
```